United States Patent
Gao et al.

[11] Patent Number: 6,028,208
[45] Date of Patent: Feb. 22, 2000

[54] VITAMIN $D_3$ DERIVATIVE AND TREATING AGENT FOR INFLAMMATORY RESPIRATORY DISEASE USING SAME

[75] Inventors: Qingzhi Gao; Kenji Manabe; Minoru Furuya; Manabu Chokki; Hiroaki Mitsuhashi; Seiichi Ishizuka; Tadashi Kishimoto, all of Hino; Masayasu Tabe, Iwakuni; Yasuji Sakuma; Atsuo Hazato, both of Tokyo, all of Japan; Hiroko Tanaka, Palo Alto, Calif.

[73] Assignee: Teijin Limited, Osaka, Japan

[21] Appl. No.: 09/242,665

[22] PCT Filed: Jun. 24, 1998

[86] PCT No.: PCT/JP98/02813

§ 371 Date: Feb. 22, 1999

§ 102(e) Date: Feb. 22, 1999

[87] PCT Pub. No.: WO98/58909

PCT Pub. Date: Dec. 30, 1998

[30] Foreign Application Priority Data

Jun. 25, 1997 [JP] Japan .................................... 9-168803

[51] Int. Cl.[7] .......................... C07C 401/00; A61K 31/59
[52] U.S. Cl. .......................... 552/653; 552/653; 514/178; 514/167
[58] Field of Search .............. 552/653; 514/167

[56] References Cited

U.S. PATENT DOCUMENTS

| | | | |
|---|---|---|---|
| 4,851,401 | 7/1989 | DeLuca et al. | 514/167 |
| 5,397,775 | 3/1995 | DeLuca et al. | 514/167 |
| 5,478,955 | 12/1995 | DeLuca et al. | 552/505 |
| 5,585,368 | 12/1996 | Steinmeyer et al. | 514/167 |

FOREIGN PATENT DOCUMENTS

| | | |
|---|---|---|
| 3-504377 | 9/1991 | Japan . |
| 8-53411 | 2/1996 | Japan . |

Primary Examiner—Jose' G. Dees
Assistant Examiner—Sabiha N. Qazi
Attorney, Agent, or Firm—Sughrue, Mion, Zinn, Macpeak & Seas, PLLC

[57] ABSTRACT

Provided are vitamin $D_3$ derivatives expressed by the following general formula [1]

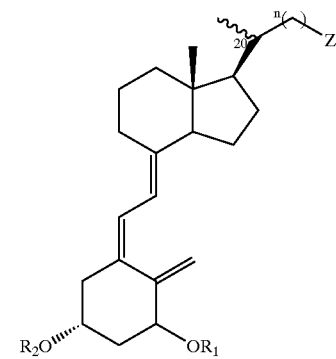

[1]

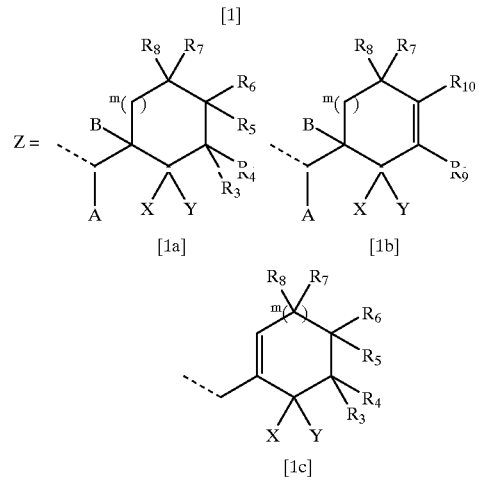

[wherein, $R_1$ and $R_2$ are each a hydrogen atom, a trialkylsilyl group, an acetyl group, a methoxymethyl group, or a tetrahydropyranyl group; $R_3$ and $R_4$ are each a hydrogen atom, a hydroxyl group, an acyloxy group, an alkyloxy group, an alkylthio group or an alkyl group which is optionally substituted; $R_5$, $R_6$, $R_7$ and $R_8$ are each a hydrogen atom, a hydroxyl group, an alkyl group or an acyloxy group; $R_9$ is a hydrogen atom, a hydroxyl group, an alkyl group or an alkylthio group; $R_{10}$ is a hydrogen atom, an alkyl group or an alkyloxy group; A and B are each a hydrogen atom, a hydroxyl group, or together express a single bond; X and Y express a carbonyl oxygen, or one of them is a hydrogen atom and the other is a hydroxyl group or an acyloxy group; n is an integer of 0 to 2; m is an integer of 0 to 2], and a method for manufacturing the derivatives.

The compounds can be sued as active ingredients of treating agents for inflammatory respiratory diseases, malignant tumors, rheumatoid arthritis, osteoporosis, diabetes mellitus, hypertension, alopecia, acne, psoriasis and dermatitis.

23 Claims, 3 Drawing Sheets

VITAMIN D₃ DERIVATIVE AND TREATING AGENT FOR INFLAMMATORY RESPIRATORY DISEASE USING SAME

TECHNICAL FIELD

The present invention relates to vitamin $D_3$ derivatives useful as pharmaceutical products or pharmaceutically permissible solvates thereof, treating agents using same, pharmaceutical compositions containing same, and a method for manufacturing same. More particularly, the invention relates to 1 α-hydroxyvitamin $D_3$ derivatives having neutrophilic infiltration-suppressing activity, the growth suppression and differentiation induction of malignant tumor cells, etc., or pharmaceutically permissible solvates thereof, treating agents for inflammatory respiratory diseases, malignant tumors, etc., containing same as active ingredients, pharmaceutical compositions containing same and a method for manufacturing same.

BACKGROUND ART

An active vitamin $D_3$ derivative has calcium absorption-stimulating activity in the small intestine, and activity such as the control of bone resorption and osteogenesis in the bones, and it is used as a treating agent for diseases caused by various kinds of calcium metabolism disorders. In recent years, immunoregulatory activity, cell proliferation inhibitory activity and cell differentiation inducing activity have been found besides these activities. For example, applications to a treating agent for rheumatoid arthritis (Japanese Unexamined Patent Publication No. 56-26820), an antiallergic agent (Japanese Un-examined Patent Publication No. 63-107928, English Patent Publica-tion No. 2260904(GB 2260904-A)), a treating agent for psoriasis (Japanese Unexamined Patent Publication No. 3-68009), a treating agent for diseases attributable to thromboxane $A_2$ production (Japanese Unexamined Patent Publication No. 5-294834), a treating agent for eczema and dermatitis (Japanese Unexamined Patent Publication No. 7-291868), etc., are being studied.

On the other hand, respiratory tract infection is a disease which is established when pathogens invade getting over infection preventing mechanisms of the respiratory tract, and the treatment is mainly based on the improvement of respiratory tract clearance by using a bronchodilator, an expectorant, etc. But, in the case of acute exacerbation with infection, the main treatment is a strong antibacterial treatment against phlogogenic bacteria. However, most underlying diseases constantly becomes worse when acute exacerbation is repeated. Further, present treatments, which depends on antibacterial agents in the extreme, are under reconsideration owing to the emergence of resistant bacteria such as MRSA.

Recently, the usefulness of a low-dose long administration of erythromycin for a chronic lower airway infectious disease has been reported, and it is attracting attention. A chronic lower airway infectious disease is a generic name for bacterial infections observed in chronic bronchitis, diffuse panbronchiolitis, bronchiectasis, etc., (sometimes, it includes bronchial asthma, chronic pulmonary emphysema, pulmonary tuberculosis sequela, etc., accompanied by infection). Although these are different in the name of disease, it is known that all of the diseases take common morbid states such as purulent sputum in large amount, fatigue dyspnea and hypoxemia. Regarding the working mechanism of erythromycin, it is understood that erythromycin's function does not depend simply on its antibacterial activity, namely, erythromycin acts not on bacteria themselves but rather on inflammatory cells which accumulate on the airway accompanied by the bacteria, especially acts on neutrophils. That is, neutrophils infiltrate into tissues by the various kinds of stimulation caused by the infection to release protease as well as active oxygen, and these substances cause epithelium damage, the trouble of ciliary movement and mucosa hypersecretion to exert a bad influence upon respiratory physiological effect, and erythromycin acts on these processes. Based on such consideration, a medicine, which suppresses the pulmonary tissue infiltration of neutrophils or suppresses the activity of neutrophils, can be useful as a treating agent for inflammatory dyspnea, for example, chronic lower airway infectious disease.

Further, regarding the effect on malignant tumor cells, it has been reported that an active vitamin $D_3$ derivative has various physiological activities such as proliferation suppression, differentiation induction and regulatory effect on immunological function. For example, it has been reported that an active vitamin derivative $D_3$ exhibits proliferation suppressing effect or differentiation inducing effect on leukemic cells (Cancer Treatment Reports, 69, 1399–1407 (1985), and Cancer Res., 43, 5862–5867 (1983)), colon cancer cells (Gut, 33, 1660–1663 (1992), and Jpn. J. Cancer Res., 88, 1052–1062 (1997)), mammary tumor cells (Cancer Res., 53, 2534–2537 (1993), prostatic cancer cells (Endocrinology, 132, 1952–1960 (1993)), etc. In addition, regarding the occurrence of human colon cancer, there is a report on the correlation between the rate of the occurrence and the uptake of vitamin $D_3$ (Lancet, 1, 307–309 (1985)).

Treatments of malignant tumors are important problems at therapy sites, and a number of treating agents for malignant tumors have been developed. However, most of the mechanisms of action of these treating agents are based on cell functional disorders, and serious side effects are often accompanied. Further, there is no effective treating agent for some kinds of malignant tumors. On these circumstances, the development of a treating agent for malignant tumor which exhibits a therapeutic effect based on a mechanism of action different from those of conventional treating agents and has little side effect is eagerly waited for.

Although therapeutic effects of vitamins Ds, especially active vitamin $D_3$ and its derivatives on malignant tumors have been studied up to now (for example, Japanese Unexamined Patent Publication No. 57-149224), sufficient therapeutic effect has not been attained due to the fact that hypercalcemia, which is considered attributable to a characteristic physiological action of vitamins Ds, causes serious side effects in actual human therapy. For developing these compounds as treating agents for malignant tumors, it is therefore assumed to be effective to use compounds which do not induce hypercalcemia while keeping proliferation suppressing effect and differentiation inducing effect of vitamins Ds on the malignant tumors.

DISCLOSURE OF THE INVENTION

It is an object of the present invention to provide new vitamin $D_3$ derivatives effective as treating agents for inflammatory respiratory diseases, which have suppressing effect on neutrophilic infiltration without inducing hypercalcemia.

Another object of the present invention is to provide new vitamin $D_3$ derivatives effective as treating agents for malignant tumors, which have growth-suppressing and differentiation-inducing effects on malignant tumor cells without inducing hypercalcemia.

Still another object of the present invention is to provide therapeutic methods for treating inflammatory respiratory diseases by using these vitamin $D_3$ derivatives as active ingredients.

Yet another object of the present invention is to provide therapeutic methods for treating malignant tumors by using these vitamin $D_3$ derivatives as active ingredients.

A further object of the present invention is to provide pharmaceutical compositions composed of these vitamin $D_3$ derivatives as active ingredients.

A still further object of the present invention is to provide a method for producing these vitamin $D_3$ derivatives.

According to the present invention, the above objects of the present invention are achieved by vitamin $D_3$ derivatives expressed by the following general formula [1]:

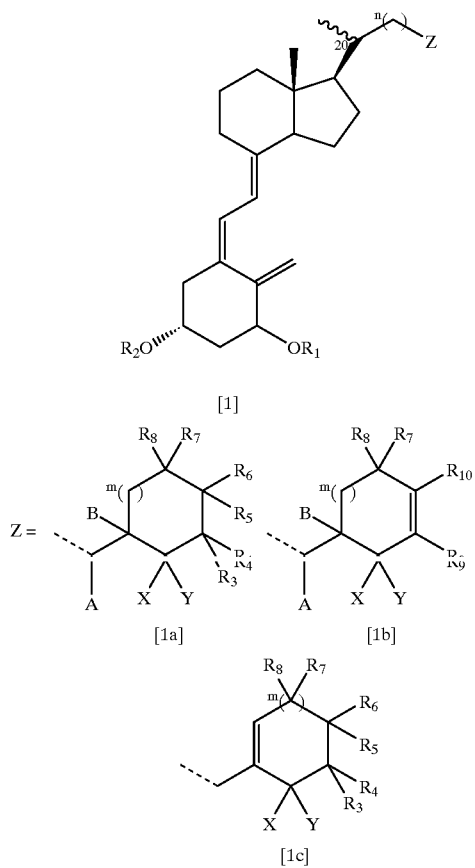

[wherein, Z is 1a, 1b or 1c; $R_1$ and $R_2$ are identical to or different from each other, and are each a hydrogen atom, a tri($C_1$–$C_7$ alkyl)silyl group, an acetyl group, a methoxymethyl group, or a tetrahydropyranyl group; $R_3$ and $R_4$ are identical to or different from each other, and are each a hydrogen atom, a hydroxyl group, a $C_2$–$C_8$ acyloxy group, a $C_1$–$C_7$ alkyloxy group, a $C_1$–$C_6$ alkylthio group or a $C_1$–$C_7$ alkyl group which is optionally substituted with a hydroxyl group, a $C_2$–$C_8$ acyloxy group or a $C_1$–$C_7$ alkyloxy group; $R_5$, $R_6$, $R_7$ and $R_8$ are identical to or different from each other, and are each a hydrogen atom, a hydroxyl group, a $C_1$–$C_7$ alkyl group or a $C_2$–$C_8$ acyloxy group; $R_9$ is a hydrogen atom, a hydroxyl group, a $C_1$–$C_7$ alkyl group or a $C_1$–$C_6$ alkylthio group; $R_{10}$ is a hydrogen atom, a $C_1$–$C_7$ alkyl group or a $C_1$–$C_7$ alkyloxy group; A and B are identical to or different from each other, and are each a hydrogen atom, a hydroxyl group, or together express a single bond and express a double bond in cooperation with the single bond already shown in the formula (later, this may be expressed "A and B together express a double bond as a whole"); X and Y together express a carbonyl group in cooperation with the carbon atom to which they are bonded, one of them is a hydrogen atom and the other is a hydroxyl group, or one of them is a hydrogen atom and the other is a $C_2$–$C_8$ acyloxy group; n is an integer of 0 to 2; m is an integer of 0 to 2], or pharmaceutically permissible solvates thereof.

The configuration of the carbon atom at the 20-position in the above formula [1] may be (S)-configuration or (R)-configuration. When a carbon atom to which $R_3$ and $R_4$, $R_5$ and $R_6$, $R_7$ and $R_8$, X and Y, or A and B are bonded becomes an asymmetric center, the configuration of the carbon atom may be (S)-configuration or (R)-configuration. Further, when A and B together express a double bond as a whole, the configuration of the double bond may be (E)-configuration or (Z)-configuration. Furthermore, the present invention includes a mixture of such stereoisomers at arbitrary ratios.

In addition, according to the present invention, above objects of the present invention are achieved by therapeutic methods for inflammatory respiratory diseases using above vitamin $D_3$ derivatives or pharmaceutically permissible solvates thereof in therapeutically effective amounts as active ingredients.

Further, according to the present invention, above objects of the present invention are achieved by therapeutic methods for malignant tumors using the above vitamin $D_3$ derivatives or pharmaceutically permissible solvates thereof in therapeutically effective amounts as active ingredients.

Further, according to the present invention, the above objects of the present invention are achieved by pharmaceutical compositions consisting of the above vitamin $D_3$ derivatives or pharmaceutically permissible solvates thereof, and pharmaceutically permissible supports.

Furthermore, according to the present invention, the above objects of the present invention are achieved by a method for producing active vitamin $D_3$ derivatives in which vitamin $D_3$ derivatives whose hydroxyl groups at the first- and the third-positions are each protected with a tri($C_1$–$C_7$ alkyl)silyl group are treated with a reagent consisting of a combination of a tetrafluoroborate alkali metal salt and a mineral acid for deprotection.

C: control group

*: statistically significant against the control group (Dunnett method: significance level of 5%)

***: statistically significant against the control group (Dunnett method: significance level of 0.01%)

Figure 2:
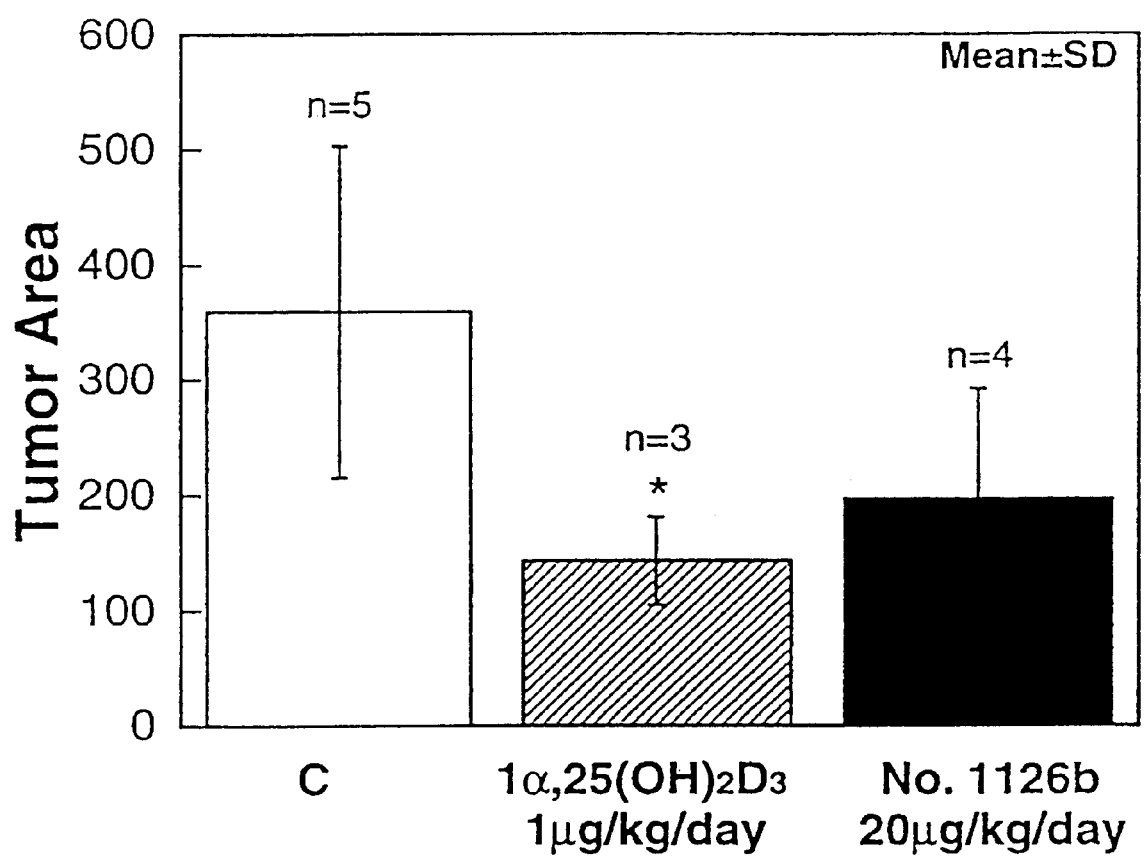

FIG. 2 is a drawing showing sizes (tumor area) of transplanted cell aggregates determined after the oral repeated administrations of an active vitamin $D_3$ (1 α, 25(OH)$_2$D$_3$) or a compound (No. 1126b) of the present invention for 2 weeks to mice in which HL-60 cells have been transplanted under the renal capsule.

C: control group

*: statistically significant against the control group (Dunnett method: significance level of 5%)

Figure 3:
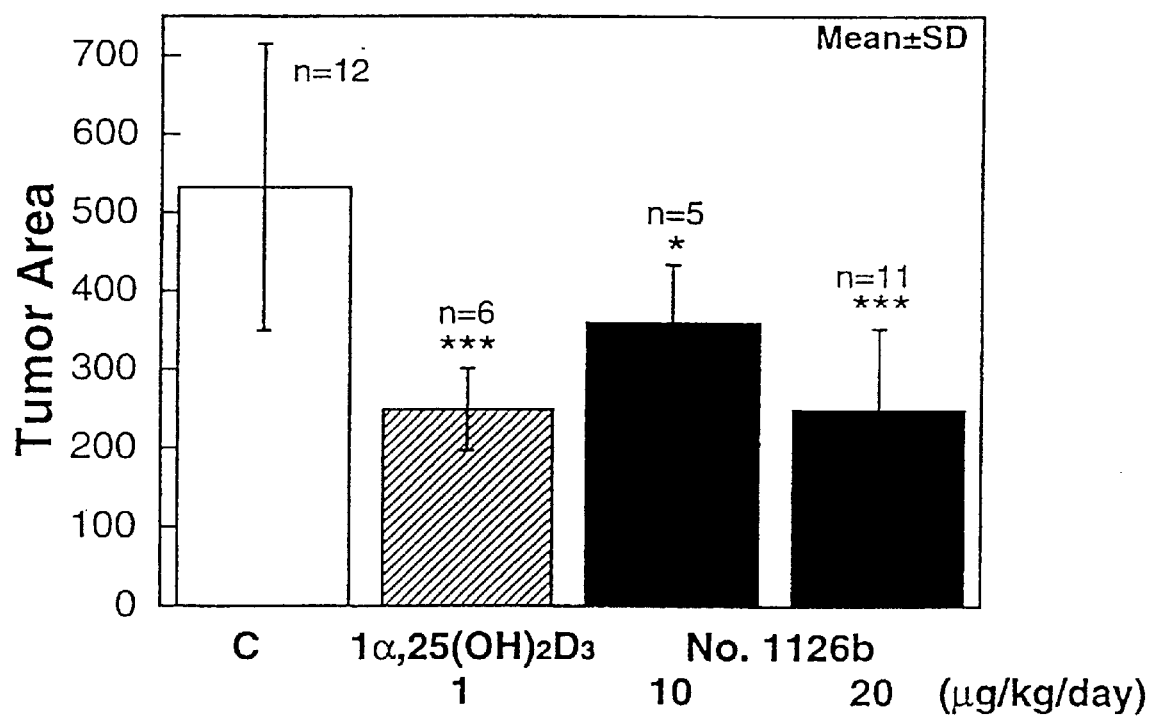

FIG. 3 is a drawing showing sizes (tumor area) of transplanted cell aggregates determined after the oral repeated administrations of an active vitamin $D_3$ (1 α, 25(OH)$_2$D$_3$) or a compound (No. 1126b) of the present invention for 2 weeks to mice in which HT-29 cells have been transplanted under the renal capsule.

C: control group

*: statistically significant against the control group (Dunnett method: significance level of 5%)

***: statistically significant against the control group (Dunnett method: significance level of 0.01%)

BEST MODE FOR CARRYING OUT THE INVENTION

Terms used in the present invention are defined as follows.

The term "alkyl group" refers to a normal or branched aliphatic hydrocarbon group or an aromatic hydrocarbon group.

The term "alkyloxy group" refers to a normal or branched aliphatic hydrocarbon-oxy group or an aromatic hydrocarbon-oxy group.

The term "acyl group" refers to a normal or branched aliphatic hydrocarbon-carbonyl group or an aromatic hydrocarbon-carbonyl group.

The term "acyloxy group" refers to a normal or branched aliphatic hydrocarbon-carbonyloxy group or a normal or branched aromatic hydrocarbon-carbonyloxy group.

The term "alkylthio group" refers to a normal or branched aliphatic hydrocarbon-thio group or an aromatic hydrocarbon-thio group.

In the above formula [1], Z is 1a, 1b or 1c. Among them is preferable 1a or 1b.

In the above formula [1], $R_1$ and $R_2$ are identical to or different from each other, and are each a hydrogen atom, a tri($C_1$–$C_7$ hydrocarbon)silyl group, an acetyl group, a methoxymethyl group, or a tetrahydropyranyl group. Among them is most preferable the case where both of $R_1$ and $R_2$ are hydrogen atoms.

Further, when $R_1$ and $R_2$ are each a tri($C_1$–$C_7$ alkyl)silyl group, for example, trimethylsilyl, triethylsilyl, t-butyldimethylsilyl, t-butyldiphenylsilyl and tribenzylsilyl groups, etc., may be cited as preferable concrete examples.

In the above formula [1], $R_3$ and $R_4$ are identical to or different from each other, and are each a hydrogen atom, a hydroxyl group, a $C_2$ to $C_8$ acyloxy group, a $C_1$ to $C_7$ alkyloxy group, a $C_1$–$C_6$ alkylthio group or a $C_1$–$C_7$ alkyl group which is optionally substituted with a hydroxyl group, a $C_2$–$C_8$ acyloxy group or a $C_1$–$C_7$ alkyloxy group.

When $R_3$ and $R_4$ are each a $C_1$–$C_7$ alkyloxy group, for example, methoxy, ethoxy, propyloxy, isopropyloxy, butyloxy, isobutyloxy, s-butyloxy, t-butyloxy, pentyloxy, isopentyloxy, neopentyloxy, hexyloxy, heptyloxy and benzyloxy groups, etc., may be cited as concrete examples. Among these groups are preferable methoxy, ethoxy, propyloxy, isopropyloxy, butyloxy, isobutyloxy, s-butyloxy, t-butyloxy and benzyloxy groups. Especially, methoxy, ethoxy and propyloxy groups are most preferable methoxy.

When $R_3$ and $R_4$ are each a $C_1$–$C_6$ alkylthio group, for example, methylthio, ethylthio, propylthio, isopropylthio, butylthio, isobutylthio, s-butylthio, t-butylthio, pentylthio, isopentylthio, neopentylthio, hexylthio, heptylthio and phenylthio groups, etc., may be cited as concrete examples. Among these groups are preferable $C_1$–$C_4$ alkylthio groups, for example, methylthio, ethylthio, propylthio, isopropylthio, butylthio, isobutylthio, s-butylthio and t-butylthio groups. Especially, methylthio, ethylthio and propylthio groups are most preferable.

When $R_3$ and $R_4$ are each a $C_2$–$C_8$ acyloxy group, for example, acetoxy, propionyloxy, isopropionyloxy, butyryloxy, isobutyryloxy, s-butyryloxy, valeryloxy, isovaleryloxy, hexanoyloxy, heptanoyloxy and benzoyloxy groups, etc., may be cited as concrete examples. Among these groups are preferable $C_2$–$C_4$ acyloxy groups, for example, acetoxy, propionyloxy, isopropionyloxy, butyryloxy, isobutyryloxy, s-butyryloxy and benzoyloxy groups.

When $R_3$ and $R_4$ are each a $C_1$–$C_7$ alkyl group which is optionally substituted with a hydroxyl group, a $C_2$–$C_8$ acyloxy group or a $C_1$–$C_7$ alkyloxy group, the $C_1$–$C_7$ alkyl group may be substituted with a hydroxyl group, a $C_2$–$C_8$ acyloxy group or a $C_1$–$C_7$ alkyloxy group at any position. As concrete examples of such alkyl groups, for example, methyl, ethyl, propyl, isopropyl, n-butyl, isobutyl, s-butyl, t-butyl, n-pentyl, isopentyl, neopentyl, n-hexyl, n-heptyl, benzyl, hydroxymethyl, hydroxyethyl, hydroxypropyl, hydroxybutyl, hydroxypentyl, hydroxyhexyl, hydroxyheptyl, hydroxybenzyl, acetoxymethyl, propionyloxymethyl, butyryloxymethyl, benzoyloxymethyl, acetoxyethyl, propionyloxyethyl, butyryloxyethyl, benzoyloxyethyl, acetoxypropyl, propionyloxypropyl, butyryloxypropyl, benzoyloxypropyl, methoxymethyl, ethoxymethyl, benzyloxymethyl, methoxyethyl, ethoxyethyl, benzyloxyethyl, methoxypropyl, ethoxypropyl and benzyloxypropyl groups, etc., may be cited. Among these groups are preferable methyl, ethyl, propyl, isopropyl, n-butyl, isobutyl, s-butyl, t-butyl, benzyl, hydroxymethyl, hydroxyethyl, hydroxybenzyl, acetoxymethyl, benzoyloxymethyl, acetoxyethyl, benzoyloxyethyl, acetoxypropyl, benzoyloxypropyl, methoxymethyl, benzyloxymethyl, methoxyethyl, benzyloxyethyl, methoxypropyl and benzyloxypropyl groups. Especially, methyl, ethyl, propyl, benzyl, hydroxymethyl, methoxymethyl and benzyloxymethyl groups are most preferable.

Further, preferable combinations of the $R_3$ and $R_4$ are follows: one of $R_3$ and $R_4$ is a hydroxyl group, and the other is a $C_1$–$C_7$ alkyl group which is optionally substituted with a hydroxyl group, a $C_2$–$C_8$ acyloxy group or a $C_1$–$C_7$ alkyloxy group; one of $R_3$ and $R_4$ is a hydrogen atom, and the other is a $C_1$–$C_7$ alkyl group which is optionally substituted with a hydroxyl group, a $C_2$–$C_8$ acyloxy group or a $C_1$–$C_7$ alkyloxy group; both of $R_3$ and $R_4$ are each a hydrogen atom; or both of $R_3$ and $R_4$ are each a $C_1$–$C_7$ alkyl group, which is optionally substituted with a hydroxyl group, a $C_2$–$C_8$ acyloxy group or a $C_1$–$C_7$ alkyloxy group, in which substituents are same or different in $R_3$ and $R_4$.

In the above formula [1], $R_5$, $R_6$, $R_7$ and $R_8$ are identical to or different from each other, and are each a hydrogen atom, a hydroxyl group, a $C_1$–$C_7$ alkyl group or a $C_2$–$C_8$ acyloxy group. Among them are preferable a hydrogen atom and a $C_1$–$C_7$ alkyl group.

When $R_5$, $R_6$, $R_7$ and $R_8$ are each a $C_1$–$C_7$ alkyl group, for example, methyl, ethyl, propyl, isopropyl, n-butyl, isobutyl, s-butyl, t-butyl, n-pentyl, isopentyl, neopentyl, n-hexyl, n-heptyl and benzyl groups may be cited as concrete examples. Among them are preferable methyl, ethyl, propyl, isopropyl, n-butyl, isobutyl, s-butyl and t-butyl groups. Especially, methyl, ethyl and propyl groups are preferable.

When $R_5$, $R_6$, $R_7$ and $R_8$ are each a $C_2$–$C_8$ acyloxy group, for example, acetoxy, propionyloxy, isopropionyloxy, butyryloxy, isobutyryloxy, s-butyryloxy, valeryloxy, isovaleryloxy, hexanoyloxy, heptanoyloxy and benzoyloxy groups, etc., may be cited as concrete examples. Among these groups are preferable $C_2$–$C_4$ acyloxy groups, for example, acetoxy, propionyloxy, isopropionyloxy, butyryloxy, isobutyryloxy, s-butyryloxy and benzoyloxy groups.

In the above formula [1], $R_9$ is a hydrogen atom, a hydroxyl group, a $C_1$–$C_7$ alkyl group or a $C_1$–$C_6$ alkylthio group.

When $R_9$ is a $C_1$–$C_7$ alkyl group, for example, methyl, ethyl, propyl, isopropyl, n-butyl, isobutyl, s-butyl, t-butyl, n-pentyl, isopentyl, neopentyl, hexyl, heptyl and benzyl groups may be cited as concrete examples. Among these groups are preferable $C_1$–$C_4$ alkyl groups, for example, methyl, ethyl, propyl, isopropyl, n-butyl, isobutyl, s-butyl and t-butyl groups. Especially, methyl, ethyl and propyl groups are most preferable.

When $R_9$ is a $C_1$–$C_6$ alkylthio group, for example, methylthio, ethylthio, propylthio, isopropylthio, butylthio, isobutylthio, s-butylthio, t-butylthio, pentylthio, isopentylthio, neopentylthio, hexylthio, heptylthio and phenylthio groups, etc., may be cited as concrete examples. Among these groups are preferable $C_1$–$C_4$ alkylthio groups, for example, methylthio, ethylthio, propylthio, isopropylthio, butylthio, isobutylthio, s-butylthio and t-butylthio groups. Especially, methylthio, ethylthio and propylthio groups are most preferable. Further, besides the above groups, $R_9$ is preferably a hydrogen atom or a hydroxyl group.

In the above formula [1], $R_{10}$ is a hydrogen atom, a $C_1$–$C_7$ alkyl group or a $C_1$–$C_7$ alkyloxy group, and among them, a hydrogen atom is When $R_{10}$ is a $C_1$–$C_7$ alkyl group, for example, methyl, ethyl, propyl, isopropyl, n-butyl, isobutyl, s-butyl, t-butyl, n-pentyl, isopentyl, neopentyl, hexyl, heptyl and benzyl groups, etc., may be cited as concrete examples. Among these groups are preferable $C_1$–$C_4$ alkyl groups, for example, methyl, ethyl, propyl, isopropyl, n-butyl, isobutyl, s-butyl and t-butyl groups. Especially, methyl, ethyl and propyl groups are most preferable.

Further, when $R_{10}$ is a $C_1$–$C_7$ alkyloxy group, for example, methoxy, ethoxy, propyloxy, isopropyloxy, butyloxy, isobutyloxy, s-butyloxy, t-butyloxy, pentyloxy, isopentyloxy, neopentyloxy, hexyloxy, heptyloxy and benzyloxy groups, etc., may be cited as concrete examples. Among these groups are preferable $C_1$–$C_4$ alkyloxy groups, for example, methoxy, ethoxy, propyloxy, isopropyloxy, butyloxy, isobutyloxy, s-butyloxy and t-butyloxy groups. Especially, methoxy, ethoxy and propyloxy groups are most preferable.

In the above formula [1], A and B are identical to or different from each other, and are each a hydrogen atom, a hydroxyl group, or together express a single bond. Among them are preferable the cases in which both of A and B are each a hydrogen atom, A is a hydroxyl group and B is a hydrogen atom, and A and B together express a single bond. Especially, the cases in which both of A and B are each a hydrogen atom, and A and B together express a single bond are most preferable.

In the above formula [1], X and Y together form a carbonyl group in cooperation with the carbon atom to which they are bonded, one of them is a hydrogen atom and the other is a hydroxyl group, or one of them is a hydrogen atom and the other is a $C_2$–$C_8$ acyloxy group. Among them are preferable the cases in which X and Y together form a carbonyl group in cooperation with the carbon atom to which they are bonded, and one of them is a hydrogen atom and the other is a hydroxyl group.

When one of X and Y is a hydrogen atom and the other is a $C_2$–$C_8$ acyloxy group, for example, acetoxy, propionyloxy, isopropionyloxy, butyryloxy, isobutyryloxy, s-butyryloxy, valeryloxy, isovaleryloxy, hexanoyloxy, heptanoyloxy and benzoyloxy groups, etc., may be cited as concrete examples of the $C_2$–$C_8$ acyloxy group. Among these groups are preferable $C_2$–$C_4$ acyl groups, for example, acetoxy, propionyloxy, isopropionyloxy, butyryloxy, isobutyryloxy and s-butyryloxy groups.

In the formula [1], n is an integer of 0 to 2. Especially, n is preferably 0 or 1.

In the formula [1], m is an integer of 0 to 2. Especially, m is preferably 0 or 1.

Vitamin $D_3$ derivatives of the present invention can be optionally converted into pharmaceutically permissible solvates thereof. Examples of a solvent to be used for such a purpose include water, methanol, ethanol, propyl alcohol, isopropyl alcohol, butanol, t-butanol, acetonitrile, acetone, methyl ethyl ketone, chloroform, ethyl acetate, diethyl ether, t-butyl methyl ether, benzene, toluene, DMF, DMSO, etc. Especially, water, methanol, ethanol, propyl alcohol, isopropyl alcohol, acetonitrile, acetone, methyl ethyl ketone and ethyl acetate may be cited as preferable examples.

Preferable concrete examples of a vitamin $D_3$ derivative of the present invention expressed by the above formula [1] are shown in Table 1-1 to Table 1-14 and Table 2-1 to Table 2-3. Further, in these compounds, the configuration of the carbon atom at the 20-position includes both (S)-configuration and (R)-configuration. When a carbon atom to which $R_3$ and $R_4$, $R_5$ and $R_6$, $R_7$ and $R_8$, X and Y, or A and B are boned becomes an asymmetric center, the configuration of the carbon includes both (S)-configuration and (R)-configuration. Further, when A and B together express a double bond as a whole, the configuration of the double bond includes both (E)-configuration and (Z)-configuration.

TABLE 1-1

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1101 | 0 | 0 | double bond | carbonyl | H, H | H, H | H, H | H, H |
| 1102 | 1 | 0 | double bond | carbonyl | H, H | H, H | H, H | H, H |
| 1103 | 2 | 0 | double bond | carbonyl | H, H | H, H | H, H | H, H |
| 1104 | 0 | 1 | double bond | carbonyl | H, H | H, H | H, H | H, H |
| 1105 | 1 | 1 | double bond | carbonyl | H, H | H, H | H, H | H, H |
| 1106 | 2 | 1 | double bond | carbonyl | H, H | H, H | H, H | H, H |
| 1107 | 0 | 2 | double bond | carbonyl | H, H | H, H | H, H | H, H |
| 1108 | 1 | 2 | double bond | carbonyl | H, H | H, H | H, H | H, H |
| 1109 | 2 | 2 | double bond | carbonyl | H, H | H, H | H, H | H, H |
| 1110 | 0 | 0 | double bond | carbonyl | H, H | H, Me | H, H | H, H |
| 1111 | 1 | 0 | double bond | carbonyl | H, H | H, Me | H, H | H, H |
| 1112 | 0 | 0 | double bond | carbonyl | H, H | H, Et | H, H | H, H |
| 1113 | 1 | 0 | double bond | carbonyl | H, H | H, Et | H, H | H, H |
| 1114 | 0 | 0 | double bond | carbonyl | H, H | H, Pr | H, H | H, H |
| 1115 | 1 | 0 | double bond | carbonyl | H, H | H, Pr | H, H | H, H |
| 1116 | 0 | 0 | double bond | carbonyl | H, H | Me, Me | H, H | H, H |
| 1117 | 1 | 0 | double bond | carbonyl | H, H | Me, Me | H, H | H, H |
| 1118 | 0 | 1 | double bond | carbonyl | H, H | H, Me | H, H | H, H |
| 1119 | 1 | 1 | double bond | carbonyl | H, H | H, Me | H, H | H, H |
| 1120 | 0 | 1 | double bond | carbonyl | H, H | H, Et | H, H | H, H |
| 1121 | 1 | 1 | double bond | carbonyl | H, H | H, Et | H, H | H, H |
| 1122 | 0 | 1 | double bond | carbonyl | H, H | H, Pr | H, H | H, H |
| 1123 | 1 | 1 | double bond | carbonyl | H, H | H, Pr | H, H | H, H |
| 1124 | 0 | 1 | double bond | carbonyl | H, H | Me, Me | H, H | H, H |
| 1125 | 1 | 1 | double bond | carbonyl | H, H | Me, Me | H, H | H, H |
| 1126 | 0 | 0 | double bond | carbonyl | H, H | Me, OH | H, H | H, H |
| 1127 | 1 | 0 | double bond | carbonyl | H, H | Me, OH | H, H | H, H |
| 1128 | 2 | 0 | double bond | carbonyl | H, H | Me, OH | H, H | H, H |
| 1129 | 0 | 1 | double bond | carbonyl | H, H | Me, OH | H, H | H, H |
| 1130 | 1 | 1 | double bond | carbonyl | H, H | Me, OH | H, H | H, H |
| 1131 | 2 | 1 | double bond | carbonyl | H, H | Me, OH | H, H | H, H |
| 1132 | 0 | 0 | double bond | carbonyl | H, H | Me, OAc | H, H | H, H |
| 1133 | 1 | 0 | double bond | carbonyl | H, H | Me, OAc | H, H | H, H |
| 1134 | 2 | 0 | double bond | carbonyl | H, H | Me, OAc | H, H | H, H |
| 1135 | 0 | 1 | double bond | carbonyl | H, H | Me, OAc | H, H | H, H |
| 1136 | 1 | 1 | double bond | carbonyl | H, H | Me, OAc | H, H | H, H |
| 1137 | 2 | 1 | double bond | carbonyl | H, H | Me, OAc | H, H | H, H |
| 1138 | 0 | 0 | double bond | carbonyl | H, H | Me, OCOn-Bu | H, H | H, H |
| 1139 | 1 | 0 | double bond | carbonyl | H, H | Me, OCOn-Bu | H, H | H, H |
| 1140 | 2 | 0 | double bond | carbonyl | H, H | Me, OCOn-Bu | H, H | H, H |
| 1141 | 0 | 1 | double bond | carbonyl | H, H | Me, OCOn-Bu | H, H | H, H |
| 1142 | 1 | 1 | double bond | carbonyl | H, H | Me, OCOn-Bu | H, H | H, H |
| 1143 | 2 | 1 | double bond | carbonyl | H, H | Me, OCOn-Bu | H, H | H, H |
| 1144 | 0 | 0 | double bond | carbonyl | H, H | Et, OH | H, H | H, H |
| 1145 | 1 | 0 | double bond | carbonyl | H, H | Et, OH | H, H | H, H |

TABLE 1-2

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1146 | 0 | 1 | double bond | carbonyl | H, H | Et, OH | H, H | H, H |
| 1147 | 1 | 1 | double bond | carbonyl | H, H | Et, OH | H, H | H, H |
| 1148 | 0 | 0 | double bond | carbonyl | H, H | Pr, OH | H, H | H, H |
| 1149 | 1 | 0 | double bond | carbonyl | H, H | Pr, OH | H, H | H, H |
| 1150 | 0 | 1 | double bond | carbonyl | H, H | Pr, OH | H, H | H, H |
| 1151 | 1 | 1 | double bond | carbonyl | H, H | Pr, OH | H, H | H, H |
| 1152 | 0 | 0 | double bond | carbonyl | H, H | $CH_2Ph$, OH | H, H | H, H |
| 1153 | 1 | 0 | double bond | carbonyl | H, H | $CH_2Ph$, OH | H, H | H, H |
| 1154 | 0 | 1 | double bond | carbonyl | H, H | $CH_2Ph$, OH | H, H | H, H |
| 1155 | 1 | 1 | double bond | carbonyl | H, H | $CH_2Ph$, OH | H, H | H, H |
| 1156 | 0 | 0 | double bond | carbonyl | H, H | Me, $CH_2OH$ | H, H | H, H |
| 1157 | 1 | 0 | double bond | carbonyl | H, H | Me, $CH_2OH$ | H, H | H, H |
| 1158 | 0 | 1 | double bond | carbonyl | H, H | Me, $CH_2OH$ | H, H | H, H |
| 1159 | 1 | 1 | double bond | carbonyl | H, H | Me, $CH_2OH$ | H, H | H, H |
| 1160 | 0 | 1 | double bond | carbonyl | H, H | H, OMe | H, H | H, H |
| 1161 | 1 | 1 | double bond | carbonyl | H, H | H, OMe | H, H | H, H |
| 1162 | 0 | 1 | double bond | carbonyl | H, H | H, OEt | H, H | H, H |

TABLE 1-2-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1163 | 1 | 1 | double bond | carbonyl | H, H | H, OEt | H, H | H, H |
| 1164 | 0 | 1 | double bond | carbonyl | H, H | H, SMe | H, H | H, H |
| 1165 | 1 | 1 | double bond | carbonyl | H, H | H, SMe | H, H | H, H |
| 1166 | 0 | 1 | double bond | carbonyl | H, H | H, tBu | H, H | H, H |
| 1167 | 1 | 1 | double bond | carbonyl | H, H | H, tBu | H, H | H, H |
| 1168 | 0 | 1 | double bond | carbonyl | H, H | H, allyl | H, H | H, H |
| 1169 | 1 | 1 | double bond | carbonyl | H, H | H, allyl | H, H | H, H |
| 1170 | 0 | 0 | double bond | carbonyl | H, H | H, H | H, Me | H, H |
| 1171 | 1 | 0 | double bond | carbonyl | H, H | H, H | H, Me | H, H |
| 1172 | 0 | 0 | double bond | carbonyl | H, H | H, H | H, Et | H, H |
| 1173 | 1 | 0 | double bond | carbonyl | H, H | H, H | H, Et | H, H |
| 1174 | 0 | 0 | double bond | carbonyl | H, H | H, H | H, Pr | H, H |
| 1175 | 1 | 0 | double bond | carbonyl | H, H | H, H | H, Pr | H, H |
| 1176 | 0 | 1 | double bond | carbonyl | H, H | H, H | H, Me | H, H |
| 1177 | 1 | 1 | double bond | carbonyl | H, H | H, H | H, Me | H, H |
| 1178 | 0 | 1 | double bond | carbonyl | H, H | H, H | H, Et | H, H |
| 1179 | 1 | 1 | double bond | carbonyl | H, H | H, H | H, Et | H, H |
| 1180 | 0 | 1 | double bond | carbonyl | H, H | H, H | H, Pr | H, H |
| 1181 | 1 | 1 | double bond | carbonyl | H, H | H, H | H, Pr | H, H |
| 1182 | 0 | 1 | double bond | carbonyl | H, H | H, H | H, H | H, Me |
| 1183 | 1 | 1 | double bond | carbonyl | H, H | H, H | H, H | H, Me |
| 1184 | 0 | 1 | double bond | carbonyl | H, H | H, H | H, H | H, Et |
| 1185 | 1 | 1 | double bond | carbonyl | H, H | H, H | H, H | H, Et |
| 1186 | 0 | 1 | double bond | carbonyl | H, H | H, H | H, H | H, tBu |
| 1187 | 1 | 1 | double bond | carbonyl | H, H | H, H | H, H | H, tBu |

TABLE 1-3

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1201 | 0 | 0 | H, H | carbonyl | H, H | H, H | H, H | H, H |
| 1202 | 1 | 0 | H, H | carbonyl | H, H | H, H | H, H | H, H |
| 1203 | 2 | 0 | H, H | carbonyl | H, H | H, H | H, H | H, H |
| 1204 | 0 | 1 | H, H | carbonyl | H, H | H, H | H, H | H, H |
| 1205 | 1 | 1 | H, H | carbonyl | H, H | H, H | H, H | H, H |
| 1206 | 2 | 1 | H, H | carbonyl | H, H | H, H | H, H | H, H |
| 1207 | 0 | 2 | H, H | carbonyl | H, H | H, H | H, H | H, H |
| 1208 | 1 | 2 | H, H | carbonyl | H, H | H, H | H, H | H, H |
| 1209 | 2 | 2 | H, H | carbonyl | H, H | H, H | H, H | H, H |
| 1210 | 0 | 0 | H, H | carbonyl | H, H | H, Me | H, H | H, H |
| 1211 | 1 | 0 | H, H | carbonyl | H, H | H, Me | H, H | H, H |
| 1212 | 0 | 0 | H, H | carbonyl | H, H | H, Et | H, H | H, H |
| 1213 | 1 | 0 | H, H | carbonyl | H, H | H, Et | H, H | H, H |
| 1214 | 0 | 0 | H, H | carbonyl | H, H | H, Pr | H, H | H, H |
| 1215 | 1 | 0 | H, H | carbonyl | H, H | H, Pr | H, H | H, H |
| 1216 | 0 | 0 | H, H | carbonyl | H, H | Me, Me | H, H | H, H |
| 1217 | 1 | 0 | H, H | carbonyl | H, H | Me, Me | H, H | H, H |
| 1218 | 0 | 1 | H, H | carbonyl | H, H | H, Me | H, H | H, H |
| 1219 | 1 | 1 | H, H | carbonyl | H, H | H, Me | H, H | H, H |
| 1220 | 0 | 1 | H, H | carbonyl | H, H | H, Et | H, H | H, H |
| 1221 | 1 | 1 | H, H | carbonyl | H, H | H, Et | H, H | H, H |
| 1222 | 0 | 1 | H, H | carbonyl | H, H | H, Pr | H, H | H, H |
| 1223 | 1 | 1 | H, H | carbonyl | H, H | H, Pr | H, H | H, H |
| 1224 | 0 | 1 | H, H | carbonyl | H, H | Me, Me | H, H | H, H |
| 1225 | 1 | 1 | H, H | carbonyl | H, H | Me, Me | H, H | H, H |
| 1226 | 0 | 0 | H, H | carbonyl | H, H | Me, OH | H, H | H, H |
| 1227 | 1 | 0 | H, H | carbonyl | H, H | Me, OH | H, H | H, H |
| 1228 | 2 | 0 | H, H | carbonyl | H, H | Me, OH | H, H | H, H |
| 1229 | 0 | 1 | H, H | carbonyl | H, H | Me, OH | H, H | H, H |
| 1230 | 1 | 1 | H, H | carbonyl | H, H | Me, OH | H, H | H, H |
| 1231 | 2 | 1 | H, H | carbonyl | H, H | Me, OH | H, H | H, H |
| 1232 | 0 | 0 | H, H | carbonyl | H, H | Me, OAc | H, H | H, H |
| 1233 | 1 | 0 | H, H | carbonyl | H, H | Me, OAc | H, H | H, H |

TABLE 1-3-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1234 | 2 | 0 | H, H | carbonyl | H, H | Me, OAc | H, H | H, H |
| 1235 | 0 | 1 | H, H | carbonyl | H, H | Me, OAc | H, H | H, H |
| 1236 | 1 | 1 | H, H | carbonyl | H, H | Me, OAc | H, H | H, H |
| 1237 | 2 | 1 | H, H | carbonyl | H, H | Me, OAc | H, H | H, H |
| 1238 | 0 | 0 | H, H | carbonyl | H, H | Me, OCOn-Bu | H, H | H, H |
| 1239 | 1 | 0 | H, H | carbonyl | H, H | Me, OCOn-Bu | H, H | H, H |
| 1240 | 2 | 0 | H, H | carbonyl | H, H | Me, OCOn-Bu | H, H | H, H |
| 1241 | 0 | 1 | H, H | carbonyl | H, H | Me, OCOn-Bu | H, H | H, H |
| 1242 | 1 | 1 | H, H | carbonyl | H, H | Me, OCOn-Bu | H, H | H, H |
| 1243 | 2 | 1 | H, H | carbonyl | H, H | Me, OCOn-Bu | H, H | H, H |
| 1244 | 0 | 0 | H, H | carbonyl | H, H | Et, OH | H, H | H, H |
| 1245 | 1 | 0 | H, H | carbonyl | H, H | Et, OH | H, H | H, H |

TABLE 1-4

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1246 | 0 | 1 | H, H | carbonyl | H, H | Et, OH | H, H | H, H |
| 1247 | 1 | 1 | H, H | carbonyl | H, H | Et, OH | H, H | H, H |
| 1248 | 0 | 0 | H, H | carbonyl | H, H | Pr, OH | H, H | H, H |
| 1249 | 1 | 0 | H, H | carbonyl | H, H | Pr, OH | H, H | H, H |
| 1250 | 0 | 1 | H, H | carbonyl | H, H | Pr, OH | H, H | H, H |
| 1251 | 1 | 1 | H, H | carbonyl | H, H | Pr, OH | H, H | H, H |
| 1252 | 0 | 0 | H, H | carbonyl | H, H | CH$_2$Ph, OH | H, H | H, H |
| 1253 | 1 | 0 | H, H | carbonyl | H, H | CH$_2$Ph, OH | H, H | H, H |
| 1254 | 0 | 1 | H, H | carbonyl | H, H | CH$_2$Ph, OH | H, H | H, H |
| 1255 | 1 | 1 | H, H | carbonyl | H, H | CH$_2$Ph, OH | H, H | H, H |
| 1256 | 0 | 0 | H, H | carbonyl | H, H | Me, CH$_2$OH | H, H | H, H |
| 1257 | 1 | 0 | H, H | carbonyl | H, H | Me, CH$_2$OH | H, H | H, H |
| 1258 | 0 | 1 | H, H | carbonyl | H, H | Me, CH$_2$OH | H, H | H, H |
| 1259 | 1 | 1 | H, H | carbonyl | H, H | Me, CH$_2$OH | H, H | H, H |
| 1260 | 0 | 1 | H, H | carbonyl | H, H | H, OMe | H, H | H, H |
| 1261 | 1 | 1 | H, H | carbonyl | H, H | H, OMe | H, H | H, H |
| 1262 | 0 | 1 | H, H | carbonyl | H, H | H, OEt | H, H | H, H |
| 1263 | 1 | 1 | H, H | carbonyl | H, H | H, OEt | H, H | H, H |
| 1264 | 0 | 1 | H, H | carbonyl | H, H | H, SMe | H, H | H, H |
| 1265 | 1 | 1 | H, H | carbonyl | H, H | H, SMe | H, H | H, H |
| 1266 | 0 | 1 | H, H | carbonyl | H, H | H, tBu | H, H | H, H |
| 1267 | 1 | 1 | H, H | carbonyl | H, H | H, tBu | H, H | H, H |
| 1268 | 0 | 1 | H, H | carbonyl | H, H | H, allyl | H, H | H, H |
| 1269 | 1 | 1 | H, H | carbonyl | H, H | H, allyl | H, H | H, H |
| 1270 | 0 | 0 | H, H | carbonyl | H, H | H, H | H, Me | H, H |
| 1271 | 1 | 0 | H, H | carbonyl | H, H | H, H | H, Me | H, H |
| 1272 | 0 | 0 | H, H | carbonyl | H, H | H, H | H, Et | H, H |
| 1273 | 1 | 0 | H, H | carbonyl | H, H | H, H | H, Et | H, H |
| 1274 | 0 | 0 | H, H | carbonyl | H, H | H, H | H, Pr | H, H |
| 1275 | 1 | 0 | H, H | carbonyl | H, H | H, H | H, Pr | H, H |
| 1276 | 0 | 1 | H, H | carbonyl | H, H | H, H | H, Me | H, H |
| 1277 | 1 | 1 | H, H | carbonyl | H, H | H, H | H, Me | H, H |
| 1278 | 0 | 1 | H, H | carbonyl | H, H | H, H | H, Et | H, H |
| 1279 | 1 | 1 | H, H | carbonyl | H, H | H, H | H, Et | H, H |
| 1280 | 0 | 1 | H, H | carbonyl | H, H | H, H | H, Pr | H, H |
| 1281 | 1 | 1 | H, H | carbonyl | H, H | H, H | H, Pr | H, H |
| 1282 | 0 | 1 | H, H | carbonyl | H, H | H, H | H, H | H, Me |
| 1283 | 1 | 1 | H, H | carbonyl | H, H | H, H | H, H | H, Me |
| 1284 | 0 | 1 | H, H | carbonyl | H, H | H, H | H, H | H, Et |
| 1285 | 1 | 1 | H, H | carbonyl | H, H | H, H | H, H | H, Et |
| 1286 | 0 | 1 | H, H | carbonyl | H, H | H, H | H, H | H, tBu |
| 1287 | 1 | 1 | H, H | carbonyl | H, H | H, H | H, H | H, tBu |

TABLE 1-5

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1301 | 0 | 0 | A = OH, B = H | carbonyl | H, H | H, H | H H | H, H |
| 1302 | 1 | 0 | A = OH, B = H | carbonyl | H, H | H, H | H, H | H, H |
| 1303 | 2 | 0 | A = OH, B = H | carbonyl | H, H | H, H | H, H | H, H |
| 1304 | 0 | 1 | A = OH, B = H | carbonyl | H, H | H, H | H, H | H, H |
| 1305 | 1 | 1 | A = OH, B = H | carbonyl | H, H | H, H | H, H | H, H |
| 1306 | 2 | 1 | A = OH, B = H | carbonyl | H, H | H, H | H, H | H, H |
| 1307 | 0 | 2 | A = OH, B = H | carbonyl | H, H | H, H | H, H | H, H |
| 1308 | 1 | 2 | A = OH, B = H | carbonyl | H, H | H, H | H, H | H, H |
| 1309 | 2 | 2 | A = OH, B = H | carbonyl | H, H | H, H | H, H | H, H |
| 1310 | 0 | 0 | A = OH, B = H | carbonyl | H, H | H, Me | H, H | H, H |
| 1311 | 1 | 0 | A = OH, B = H | carbonyl | H, H | H, Me | H, H | H, H |
| 1312 | 0 | 0 | A = OH, B = H | carbonyl | H, H | H, Et | H, H | H, H |
| 1313 | 1 | 0 | A = OH, B = H | carbonyl | H, H | H, Et | H, H | H, H |
| 1314 | 0 | 0 | A = OH, B = H | carbonyl | H, H | H, Pr | H, H | H, H |
| 1315 | 1 | 0 | A = OH, B = H | carbonyl | H, H | H, Pr | H, H | H, H |
| 1316 | 0 | 0 | A = OH, B = H | carbonyl | H, H | Me, Me | H, H | H, H |
| 1317 | 1 | 0 | A = OH, B = H | carbonyl | H, H | Me, Me | H, H | H, H |
| 1318 | 0 | 1 | A = OH, B = H | carbonyl | H, H | H, Me | H, H | H, H |
| 1319 | 1 | 1 | A = OH, B = H | carbonyl | H, H | H, Me | H, H | H, H |
| 1320 | 0 | 1 | A = OH, B = H | carbonyl | H, H | H, Et | H, H | H, H |
| 1321 | 1 | 1 | A = OH, B = H | carbonyl | H, H | H, Et | H, H | H, H |
| 1322 | 0 | 1 | A = OH, B = H | carbonyl | H, H | H, Pr | H, H | H, H |
| 1323 | 1 | 1 | A = OH, B = H | carbonyl | H, H | H, Pr | H, H | H, H |
| 1324 | 0 | 1 | A = OH, B = H | carbonyl | H, H | Me, Me | H, H | H, H |
| 1325 | 1 | 1 | A = OH, B = H | carbonyl | H, H | Me, Me | H, H | H, H |
| 1326 | 0 | 0 | A = OH, B = H | carbonyl | H, H | Me, OH | H, H | H, H |
| 1327 | 1 | 0 | A = OH, B = H | carbonyl | H, H | Me, OH | H, H | H, H |
| 1328 | 2 | 0 | A = OH, B = H | carbonyl | H, H | Me, OH | H, H | H, H |
| 1329 | 0 | 1 | A = OH, B = H | carbonyl | H, H | Me, OH | H, H | H, H |
| 1330 | 1 | 1 | A = OH, B = H | carbonyl | H, H | Me, OH | H, H | H, H |
| 1331 | 2 | 1 | A = OH, B = H | carbonyl | H, H | Me, OH | H, H | H, H |
| 1332 | 0 | 0 | A = OH, B = H | carbonyl | H, H | Me, OAc | H, H | H, H |
| 1333 | 1 | 0 | A = OH, B = H | carbonyl | H, H | Me, OAc | H, H | H, H |
| 1334 | 2 | 0 | A = OH, B = H | carbonyl | H, H | Me, OAc | H, H | H, H |
| 1335 | 0 | 1 | A = OH, B = H | carbonyl | H, H | Me, OAc | H, H | H, H |
| 1336 | 1 | 1 | A = OH, B = H | carbonyl | H, H | Me, OAc | H, H | H, H |
| 1337 | 2 | 1 | A = OH, B = H | carbonyl | H, H | Me, OAc | H, H | H, H |
| 1338 | 0 | 0 | A = OH, B = H | carbonyl | H, H | Me, OCOn-Bu | H, H | H, H |
| 1339 | 1 | 0 | A = OH, B = H | carbonyl | H, H | Me, OCOn-Bu | H, H | H, H |
| 1340 | 2 | 0 | A = OH, B = H | carbonyl | H, H | Me, OCOn-Bu | H, H | H, H |
| 1341 | 0 | 1 | A = OH, B = H | carbonyl | H, H | Me, OCOn-Bu | H, H | H, H |
| 1342 | 1 | 1 | A = OH, B = H | carbonyl | H, H | Me, OCOn-Bu | H, H | H, H |
| 1343 | 2 | 1 | A = OH, B = H | carbonyl | H, H | Me, OCOn-Bu | H, H | H, H |
| 1344 | 0 | 0 | A = OH, B = H | carbonyl | H, H | Et, OH | H, H | H, H |
| 1345 | 1 | 0 | A = OH, B = H | carbonyl | H, H | Et, OH | H, H | H, H |

TABLE 1-6

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1346 | 0 | 1 | A = OH, B = H | carbonyl | H, H | Et, OH | H, H | H, H |
| 1347 | 1 | 1 | A = OH, B = H | carbonyl | H, H | Et, OH | H, H | H, H |
| 1348 | 0 | 0 | A = OH, B = H | carbonyl | H, H | Pr, OH | H, H | H, H |
| 1349 | 1 | 0 | A = OH, B = H | carbonyl | H, H | Pr, OH | H, H | H, H |
| 1350 | 0 | 1 | A = OH, B = H | carbonyl | H, H | Pr, OH | H, H | H, H |
| 1351 | 1 | 1 | A = OH, B = H | carbonyl | H, H | Pr, OH | H, H | H, H |
| 1352 | 0 | 0 | A = OH, B = H | carbonyl | H, H | CH$_2$Ph, OH | H, H | H, H |
| 1353 | 1 | 0 | A = OH, B = H | carbonyl | H, H | CH$_2$Ph, OH | H, H | H, H |
| 1354 | 0 | 1 | A = OH, B = H | carbonyl | H, H | CH$_2$Ph, OH | H, H | H, H |
| 1355 | 1 | 1 | A = OH, B = H | carbonyl | H, H | CH$_2$Ph, OH | H, H | H, H |
| 1356 | 0 | 0 | A = OH, B = H | carbonyl | H, H | Me, CH$_2$OH | H, H | H, H |
| 1357 | 1 | 0 | A = OH, B = H | carbonyl | H, H | Me, CH$_2$OH | H, H | H, H |
| 1358 | 0 | 1 | A = OH, B = H | carbonyl | H, H | Me, CH$_2$OH | H, H | H, H |

TABLE 1-6-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1359 | 1 | 1 | A = OH, B = H | carbonyl | H, H | Me, CH$_2$OH | H, H | H, H |
| 1360 | 0 | 1 | A = OH, B = H | carbonyl | H, H | H, OMe | H, H | H, H |
| 1361 | 1 | 1 | A = OH, B = H | carbonyl | H, H | H, OMe | H, H | H, H |
| 1362 | 0 | 1 | A = OH, B = H | carbonyl | H, H | H, OEt | H, H | H, H |
| 1363 | 1 | 1 | A = OH, B = H | carbonyl | H, H | H, OEt | H, H | H, H |
| 1364 | 0 | 1 | A = OH, B = H | carbonyl | H, H | H, SMe | H, H | H, H |
| 1365 | 1 | 1 | A = OH, B = H | carbonyl | H, H | H, SMe | H, H | H, H |
| 1366 | 0 | 1 | A = OH, B = H | carbonyl | H, H | H, tBu | H, H | H, H |
| 1367 | 1 | 1 | A = OH, B = H | carbonyl | H, H | H, tBu | H, H | H, H |
| 1368 | 0 | 1 | A = OH, B = H | carbonyl | H, H | H, allyl | H, H | H, H |
| 1369 | 1 | 1 | A = OH, B = H | carbonyl | H, H | H, allyl | H, H | H, H |
| 1370 | 0 | 0 | A = OH, B = H | carbonyl | H, H | H, H | H, Me | H, H |
| 1371 | 1 | 0 | A = OH, B = H | carbonyl | H, H | H, H | H, Me | H, H |
| 1372 | 0 | 0 | A = OH, B = H | carbonyl | H, H | H, H | H, Et | H, H |
| 1373 | 1 | 0 | A = OH, B = 4 | carbonyl | H, H | H, H | H, Et | H, H |
| 1374 | 0 | 0 | A = OH, B = H | carbonyl | H, H | H, H | H, Pr | H, H |
| 1375 | 1 | 0 | A = OH, B = H | carbonyl | H, H | H, H | H, Pr | H, H |
| 1376 | 0 | 1 | A = OH, B = H | carbonyl | H, H | H, H | H, Me | H, H |
| 1377 | 1 | 1 | A = OH, B = H | carbonyl | H, H | H, H | H, Me | H, H |
| 1378 | 0 | 1 | A = OH, B = H | carbonyl | H, H | H, H | H, Et | H, H |
| 1379 | 1 | 1 | A = OH, B = H | carbonyl | H, H | H, H | H, Et | H, H |
| 1380 | 0 | 1 | A = OH, B = H | carbonyl | H, H | H, H | H, Pr | H, H |
| 1381 | 1 | 1 | A = OH, B = H | carbonyl | H, H | H, H | H, Pr | H, H |
| 1382 | 0 | 1 | A = OH, B = H | carbonyl | H, H | H, H | H, H | H, Me |
| 1383 | 1 | 1 | A = OH, B = H | carbonyl | H, H | H, H | H, H | H, Me |
| 1384 | 0 | 1 | A = OH, B = H | carbonyl | H, H | H, H | H, H | H, Et |
| 1385 | 1 | 1 | A = OH, B = H | carbonyl | H, H | H, H | H, H | H, Et |
| 1386 | 0 | 1 | A = OH, B = H | carbonyl | H, H | H, H | H, H | H, tBu |
| 1387 | 1 | 1 | A = OH, B = H | carbonyl | H, H | H, H | H, H | H, tBu |

TABLE 1-7

Structure of Compound: formula [1], Z = [1a]

| Comp. No | n | m | A, B | X, Y | R1, R2 | R3, R4 | R5, R6 | R7, R8 |
|---|---|---|---|---|---|---|---|---|
| 1401 | 0 | 0 | double bond | OH, H | H, H | H, H | H, H | H, H |
| 1402 | 1 | 0 | double bond | OH, H | H, H | H, H | H, H | H, H |
| 1403 | 2 | 0 | double bond | OH, H | H, H | H, H | H, H | H, H |
| 1404 | 0 | 1 | double bond | OH, H | H, H | H, H | H, H | H, H |
| 1405 | 1 | 1 | double bond | OH, H | H, H | H, H | H, H | H, H |
| 1406 | 2 | 1 | double bond | OH, H | H, H | H, H | H, H | H, H |
| 1407 | 0 | 2 | double bond | OH, H | H, H | H, H | H, H | H, H |
| 1408 | 1 | 2 | double bond | OH, H | H, H | H, H | H, H | H, H |
| 1409 | 2 | 2 | double bond | OH, H | H, H | H, H | H, H | H, H |
| 1410 | 0 | 0 | double bond | OH, H | H, H | H, Me | H, H | H, H |
| 1411 | 1 | 0 | double bond | OH, H | H, H | H, Me | H, H | H, H |
| 1412 | 0 | 0 | double bond | OH, H | H, H | H, Et | H, H | H, H |
| 1413 | 1 | 0 | double bond | OH, H | H, H | H, Et | H, H | H, H |
| 1414 | 0 | 0 | double bond | OH, H | H, H | H, Pr | H, H | H, H |
| 1415 | 1 | 0 | double bond | OH, H | H, H | H, Pr | H, H | H, H |
| 1416 | 0 | 0 | double bond | OH, H | H, H | Me, Me | H, H | H, H |
| 1417 | 1 | 0 | double bond | OH, H | H, H | Me, Me | H, H | H, H |
| 1418 | 0 | 1 | double bond | OH, H | H, H | H, Me | H, H | H, H |
| 1419 | 1 | 1 | double bond | OH, H | H, H | H, Me | H, H | H, H |
| 1420 | 0 | 1 | double bond | OH, H | H, H | H, Et | H, H | H, H |
| 1421 | 1 | 1 | double bond | OH, H | H, H | H, Et | H, H | H, H |
| 1422 | 0 | 1 | double bond | OH, H | H, H | H, Pr | H, H | H, H |
| 1423 | 1 | 1 | double bond | OH, H | H, H | H, Pr | H, H | H, H |
| 1424 | 0 | 1 | double bond | OH, H | H, H | Me, Me | H, H | H, H |
| 1425 | 1 | 1 | double bond | OH, H | H, H | Me, Me | H, H | H, H |
| 1426 | 0 | 0 | double bond | OH, H | H, H | Me, OH | H, H | H, H |
| 1427 | 1 | 0 | double bond | OH, H | H, H | Me, OH | H, H | H, H |
| 1428 | 2 | 0 | double bond | OH, H | H, H | Me, OH | H, H | H, H |
| 1429 | 0 | 1 | double bond | OH, H | H, H | Me, OH | H, H | H, H |

TABLE 1-7-continued

Structure of Compound: formula [1], Z = [1a]

| Comp. No | n | m | A, B | X, Y | R1, R2 | R3, R4 | R5, R6 | R7, R8 |
|---|---|---|---|---|---|---|---|---|
| 1430 | 1 | 1 | double bond | OH, H | H, H | Me, OH | H, H | H, H |
| 1431 | 2 | 1 | double bond | OH, H | H, H | Me, OH | H, H | H, H |
| 1432 | 0 | 0 | double bond | OH, H | H, H | Me, OAc | H, H | H, H |
| 1433 | 1 | 0 | double bond | OH, H | H, H | Me, OAc | H, H | H, H |
| 1434 | 2 | 0 | double bond | OH, H | H, H | Me, OAc | H, H | H, H |
| 1435 | 0 | 1 | double bond | OH, H | H, H | Me, OAc | H, H | H, H |
| 1436 | 1 | 1 | double bond | OH, H | H, H | Me, OAc | H, H | H, H |
| 1437 | 2 | 1 | double bond | OH, H | H, H | Me, OAc | H, H | H, H |
| 1438 | 0 | 0 | double bond | OH, H | H, H | Me, OCOn-Bu | H, H | H, H |
| 1439 | 1 | 0 | double bond | OH, H | H, H | Me, OCOn-Bu | H, H | H, H |
| 1440 | 2 | 0 | double bond | OH, H | H, H | Me, OCOn-Bu | H, H | H, H |
| 1441 | 0 | 1 | double bond | OH, H | H, H | Me, OCOn-Bu | H, H | H, H |
| 1442 | 1 | 1 | double bond | OH, H | H, H | Me, OCOn-Bu | H, H | H, H |
| 1443 | 2 | 1 | double bond | OH, H | H, H | Me, OCOn-Bu | H, H | H, H |
| 1444 | 0 | 0 | double bond | OH, H | H, H | Et, OH | H, H | H, H |
| 1445 | 1 | 0 | double bond | OH, H | H, H | Et, OH | H, H | H, H |

TABLE 1-8

Structure of Compound: formula [1], Z = [1a]

| Comp. No | n | m | A, B | X, Y | R1, R2 | R3, R4 | R5, R6 | R7, R8 |
|---|---|---|---|---|---|---|---|---|
| 1446 | 0 | 1 | double bond | OH, H | H, H | Et, OH | H, H | H, H |
| 1447 | 1 | 1 | double bond | OH, H | H, H | Et, OH | H, H | H, H |
| 1448 | 0 | 0 | double bond | OH, H | H, H | Pr, OH | H, H | H, H |
| 1449 | 1 | 0 | double bond | OH, H | H, H | Pr, OH | H, H | H, H |
| 1450 | 0 | 1 | double bond | OH, H | H, H | Pr, OH | H, H | H, H |
| 1451 | 1 | 1 | double bond | OH, H | H, H | Pr, OH | H, H | H, H |
| 1452 | 0 | 0 | double bond | OH, H | H, H | $CH_2Ph$, OH | H, H | H, H |
| 1453 | 1 | 0 | double bond | OH, H | H, H | $CH_2Ph$, OH | H, H | H, H |
| 1454 | 0 | 1 | double bond | OH, H | H, H | $CH_2Ph$, OH | H, H | H, H |
| 1455 | 1 | 1 | double bond | OH, H | H, H | $CH_2Ph$, OH | H, H | H, H |
| 1456 | 0 | 0 | double bond | OH, H | H, H | Me, $CH_2OH$ | H, H | H, H |
| 1457 | 1 | 0 | double bond | OH, H | H, H | Me, $CH_2OH$ | H, H | H, H |
| 1458 | 0 | 1 | double bond | OH, H | H, H | Me, $CH_2OH$ | H, H | H, H |
| 1459 | 1 | 1 | double bond | OH, H | H, H | Me, $CH_2OH$ | H, H | H, H |
| 1460 | 0 | 1 | double bond | OH, H | H, H | H, OMe | H, H | H, H |
| 1461 | 1 | 1 | double bond | OH, H | H, H | H, OMe | H, H | H, H |
| 1462 | 0 | 1 | double bond | OH, H | H, H | H, OEt | H, H | H, H |
| 1463 | 1 | 1 | double bond | OH, H | H, H | H, OEt | H, H | H, H |
| 1464 | 0 | 1 | double bond | OH, H | H, H | H, SMe | H, H | H, H |
| 1465 | 1 | 1 | double bond | OH, H | H, H | H, SMe | H, H | H, H |
| 1466 | 0 | 1 | double bond | OH, H | H, H | H, tBu | H, H | H, H |
| 1467 | 1 | 1 | double bond | OH, H | H, H | H, tBu | H, H | H, H |
| 1468 | 0 | 1 | double bond | OH, H | H, H | H, allyl | H, H | H, H |
| 1469 | 1 | 1 | double bond | OH, H | H, H | H, allyl | H, H | H, H |
| 1470 | 0 | 0 | double bond | OH, H | H, H | H, H | H, Me | H, H |
| 1471 | 1 | 0 | double bond | OH, H | H, H | H, H | H, Me | H, H |
| 1472 | 0 | 0 | double bond | OH, H | H, H | H, H | H, Et | H, H |
| 1473 | 1 | 0 | double bond | OH, H | H, H | H, H | H, Et | H, H |
| 1474 | 0 | 0 | double bond | OH, H | H, H | H, H | H, Pr | H, H |
| 1475 | 1 | 0 | double bond | OH, H | H, H | H, H | H, Pr | H, H |
| 1476 | 0 | 1 | double bond | OH, H | H, H | H, H | H, Me | H, H |
| 1477 | 1 | 1 | double bond | OH, H | H, H | H, H | H, Me | H, H |
| 1478 | 0 | 1 | double bond | OH, H | H, H | H, H | H, Et | H, H |
| 1479 | 1 | 1 | double bond | OH, H | H, H | H, H | H, Et | H, H |
| 1480 | 0 | 1 | double bond | OH, H | H, H | H, H | H, Pr | H, H |
| 1481 | 1 | 1 | double bond | OH, H | H, H | H, H | H, Pr | H, H |
| 1482 | 0 | 1 | double bond | OH, H | H, H | H, H | H, H | H, Me |
| 1483 | 1 | 1 | double bond | OH, H | H, H | H, H | H, H | H, Me |
| 1484 | 0 | 1 | double bond | OH, H | H, H | H, H | H, H | H, Et |
| 1485 | 1 | 1 | double bond | OH, H | H, H | H, H | H, H | H, Et |
| 1486 | 0 | 1 | double bond | OH, H | H, H | H, H | H, H | H, tBu |
| 1487 | 1 | 1 | double bond | OH, H | H, H | H, H | H, H | H, tBu |

TABLE 1-9

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1501 | 0 | 0 | H, H | OH, H | H, H | H, H | H, H | H, H |
| 1502 | 1 | 0 | H, H | OH, H | H, H | H, H | H, H | H, H |
| 1503 | 2 | 0 | H, H | OH, H | H, H | H, H | H, H | H, H |
| 1504 | 0 | 1 | H, H | OH, H | H, H | H, H | H, H | H, H |
| 1505 | 1 | 1 | H, H | OH, H | H, H | H, H | H, H | H, H |
| 1506 | 2 | 1 | H, H | OH, H | H, H | H, H | H, H | H, H |
| 1507 | 0 | 2 | H, H | OH, H | H, H | H, H | H, H | H, H |
| 1508 | 1 | 2 | H, H | OH, H | H, H | H, H | H, H | H, H |
| 1509 | 2 | 2 | H, H | OH, H | H, H | H, H | H, H | H, H |
| 1510 | 0 | 0 | H, H | OH, H | H, H | H, Me | H, H | H, H |
| 1511 | 1 | 0 | H, H | OH, H | H, H | H, Me | H, H | H, H |
| 1512 | 0 | 0 | H, H | OH, H | H, H | H, Et | H, H | H, H |
| 1513 | 1 | 0 | H, H | OH, H | H, H | H, Et | H, H | H, H |
| 1514 | 0 | 0 | H, H | OH, H | H, H | H, Pr | H, H | H, H |
| 1515 | 1 | 0 | H, H | OH, H | H, H | H, Pr | H, H | H, H |
| 1516 | 0 | 0 | H, H | OH, H | H, H | Me, Me | H, H | H, H |
| 1517 | 1 | 0 | H, H | OH, H | H, H | Me, Me | H, H | H, H |
| 1518 | 0 | 1 | H, H | OH, H | H, H | H, Me | H, H | H, H |
| 1519 | 1 | 1 | H, H | OH, H | H, H | H, Me | H, H | H, H |
| 1520 | 0 | 1 | H, H | OH, H | H, H | H, Et | H, H | H, H |
| 1521 | 1 | 1 | H, H | OH, H | H, H | H, Et | H, H | H, H |
| 1522 | 0 | 1 | H, H | OH, H | H, H | H, Pr | H, H | H, H |
| 1523 | 1 | 1 | H, H | OH, H | H, H | H, Pr | H, H | H, H |
| 1524 | 0 | 1 | H, H | OH, H | H, H | Me, Me | H, H | H, H |
| 1525 | 1 | 1 | H, H | OH, H | H, H | Me, Me | H, H | H, H |
| 1526 | 0 | 0 | H, H | OH, H | H, H | Me, OH | H, H | H, H |
| 1527 | 1 | 0 | H, H | OH, H | H, H | Me, OH | H, H | H, H |
| 1528 | 2 | 0 | H, H | OH, H | H, H | Me, OH | H, H | H, H |
| 1529 | 0 | 1 | H, H | OH, H | H, H | Me, OH | H, H | H, H |
| 1530 | 1 | 1 | H, H | OH, H | H, H | Me, OH | H, H | H, H |
| 1531 | 2 | 1 | H, H | OH, H | H, H | Me, OH | H, H | H, H |
| 1532 | 0 | 0 | H, H | OH, H | H, H | Me, OAc | H, H | H, H |
| 1533 | 1 | 0 | H, H | OH, H | H, H | Me, OAc | H, H | H, H |
| 1534 | 2 | 0 | H, H | OH, H | H, H | Me, OAc | H, H | H, H |
| 1535 | 0 | 1 | H, H | OH, H | H, H | Me, OAc | H, H | H, H |
| 1536 | 1 | 1 | H, H | OH, H | H, H | Me, OAc | H, H | H, H |
| 1537 | 2 | 1 | H, H | OH, H | H, H | Me, OAc | H, H | H, H |
| 1538 | 0 | 0 | H, H | OH, H | H, H | Me, OCOn-Bu | H, H | H, H |
| 1539 | 1 | 0 | H, H | OH, H | H, H | Me, OCOn-Bu | H, H | H, H |
| 1540 | 2 | 0 | H, H | OH, H | H, H | Me, OCOn-Bu | H, H | H, H |
| 1541 | 0 | 1 | H, H | OH, H | H, H | Me, OCOn-Bu | H, H | H, H |
| 1542 | 1 | 1 | H, H | OH, H | H, H | Me, OCOn-Bu | H, H | H, H |
| 1543 | 2 | 1 | H, H | OH, H | H, H | Me, OCOn-Bu | H, H | H, H |
| 1544 | 0 | 0 | H, H | OH, H | H, H | Et, OH | H, H | H, H |
| 1545 | 1 | 0 | H, H | OH, H | H, H | Et, OH | H, H | H, H |

TABLE 1-10

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1546 | 0 | 1 | H, H | OH, H | H, H | Et, OH | H, H | H, H |
| 1547 | 1 | 1 | H, H | OH, H | H, H | Et, OH | H, H | H, H |
| 1548 | 0 | 0 | H, H | OH, H | H, H | Pr, OH | H, H | H, H |
| 1549 | 1 | 0 | H, H | OH, H | H, H | Pr, OH | H, H | H, H |
| 1550 | 0 | 1 | H, H | OH, H | H, H | Pr, OH | H, H | H, H |
| 1551 | 1 | 1 | H, H | OH, H | H, H | Pr, OH | H, H | H, H |
| 1552 | 0 | 0 | H, H | OH, H | H, H | CH$_2$Ph, OH | H, H | H, H |
| 1553 | 1 | 0 | H, H | OH, H | H, H | CH$_2$Ph, OH | H, H | H, H |
| 1554 | 0 | 1 | H, H | OH, H | H, H | CH$_2$Ph, OH | H, H | H, H |
| 1555 | 1 | 1 | H, H | OH, H | H, H | CH$_2$Ph, OH | H, H | H, H |
| 1556 | 0 | 0 | H, H | OH, H | H, H | Me, CH$_2$OH | H, H | H, H |
| 1557 | 1 | 0 | H, H | OH, H | H, H | Me, CH$_2$OH | H, H | H, H |
| 1558 | 0 | 1 | H, H | OH, H | H, H | Me, CH$_2$OH | H, H | H, H |

TABLE 1-10-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1559 | 1 | 1 | H, H | OH, H | H, H | Me, CH₂OH | H, H | H, H |
| 1560 | 0 | 1 | H, H | OH, H | H, H | H, OMe | H, H | H, H |
| 1561 | 1 | 1 | H, H | OH, H | H, H | H, OMe | H, H | H, H |
| 1562 | 0 | 1 | H, H | OH, H | H, H | H, OEt | H, H | H, H |
| 1563 | 1 | 1 | H, H | OH, H | H, H | H, OEt | H, H | H, H |
| 1564 | 0 | 1 | H, H | OH, H | H, H | H, SMe | H, H | H, H |
| 1565 | 1 | 1 | H, H | OH, H | H, H | H, SMe | H, H | H, H |
| 1566 | 0 | 1 | H, H | OH, H | H, H | H, tBu | H, H | H, H |
| 1567 | 1 | 1 | H, H | OH, H | H, H | H, tBu | H, H | H, H |
| 1568 | 0 | 1 | H, H | OH, H | H, H | H, allyl | H, H | H, H |
| 1569 | 1 | 1 | H, H | OH, H | H, H | H, allyl | H, H | H, H |
| 1570 | 0 | 0 | H, H | OH, H | H, H | H, H | H, H | H, H |
| 1571 | 1 | 0 | H, H | OH, H | H, H | H, H | H, Me | H, H |
| 1572 | 0 | 0 | H, H | OH, H | H, H | H, H | H, Et | H, H |
| 1573 | 1 | 0 | H, H | OH, H | H, H | H, H | H, Et | H, H |
| 1574 | 0 | 0 | H, H | OH, H | H, H | H, H | H, Pr | H, H |
| 1575 | 1 | 0 | H, H | OH, H | H, H | H, H | H, Pr | H, H |
| 1576 | 0 | 1 | H, H | OH, H | H, H | H, H | H, Me | H, H |
| 1577 | 1 | 1 | H, H | OH, H | H, H | H, H | H, Me | H, H |
| 1578 | 0 | 1 | H, H | OH, H | H, H | H, H | H, Et | H, H |
| 1579 | 1 | 1 | H, H | OH, H | H, H | H, H | H, Et | H, H |
| 1580 | 0 | 1 | H, H | OH, H | H, H | H, H | H, Pr | H, H |
| 1581 | 1 | 1 | H, H | OH, H | H, H | H, H | H, Pr | H, H |
| 1582 | 0 | 1 | H, H | OH, H | H, H | H, H | H, H | H, Me |
| 1583 | 1 | 1 | H, H | OH, H | H, H | H, H | H, H | H, Me |
| 1584 | 0 | 1 | H, H | OH, H | H, H | H, H | H, H | H, Et |
| 1585 | 1 | 1 | H, H | OH, H | H, H | H, H | H, H | H, Et |
| 1586 | 0 | 1 | H, H | OH, H | H, H | H, H | H, H | H, tBu |
| 1587 | 1 | 1 | H, H | OH, H | H, H | H, H | H, H | H, tBu |

TABLE 1-11

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1601 | 0 | 0 | A = H, B = OH | carbonyl | H, H | H, H | H, H | H, H |
| 1602 | 1 | 0 | A = H, B = OH | carbonyl | H, H | H, H | H, H | H, H |
| 1603 | 2 | 0 | A = H, B = OH | carbonyl | H, H | H, H | H, H | H, H |
| 1604 | 0 | 1 | A = H, B = OH | carbonyl | H, H | H, H | H, H | H, H |
| 1605 | 1 | 1 | A = H, B = OH | carbonyl | H, H | H, H | H, H | H, H |
| 1606 | 2 | 1 | A = H, B = OH | carbonyl | H, H | H, H | H, H | H, H |
| 1607 | 0 | 2 | A = H, B = OH | carbonyl | H, H | H, H | H, H | H, H |
| 1608 | 1 | 2 | A = H, B = OH | carbonyl | H, H | H, H | H, H | H, H |
| 1609 | 2 | 2 | A = H, B = OH | carbonyl | H, H | H, H | H, H | H, H |
| 1610 | 0 | 0 | A = H, B = OH | carbonyl | H, H | H, H | H, Me | H, H |
| 1611 | 1 | 0 | A = H, B = OH | carbonyl | H, H | H, H | H, Me | H, H |
| 1612 | 0 | 0 | A = H, B = OH | carbonyl | H, H | H, H | H, Et | H, H |
| 1613 | 1 | 0 | A = H, B = OH | carbonyl | H, H | H, H | H, Et | H, H |
| 1614 | 0 | 0 | A = H, B = OH | carbonyl | H, H | H, H | H, Pr | H, H |
| 1615 | 1 | 0 | A = H, B = OH | carbonyl | H, H | H, H | H, Pr | H, H |
| 1616 | 0 | 0 | A = H, B = OH | carbonyl | H, H | H, H | Me, Me | H, H |
| 1617 | 1 | 0 | A = H, B = OH | carbonyl | H, H | H, H | Me, Me | H, H |
| 1618 | 0 | 1 | A = H, B = OH | carbonyl | H, H | H, H | H, Me | H, H |
| 1619 | 1 | 1 | A = H, B = OH | carbonyl | H, H | H, H | H, Me | H, H |
| 1620 | 0 | 1 | A = H, B = OH | carbonyl | H, H | H, H | H, Et | H, H |
| 1621 | 1 | 1 | A = H, B = OH | carbonyl | H, H | H, H | H, Et | H, H |
| 1622 | 0 | 1 | A = H, B = OH | carbonyl | H, H | H, H | H, Pr | H, H |
| 1623 | 1 | 1 | A = H, B = OH | carbonyl | H, H | H, H | H, Pr | H, H |
| 1624 | 0 | 1 | A = H, B = OH | carbonyl | H, H | H, H | Me, Me | H, H |
| 1625 | 1 | 1 | A = H, B = OH | carbonyl | H, H | H, H | Me, Me | H, H |
| 1626 | 0 | 0 | A = H, B = OH | carbonyl | H, H | H, H | Me, OH | H, H |
| 1627 | 1 | 0 | A = H, B = OH | carbonyl | H, H | H, H | Me, OH | H, H |
| 1628 | 2 | 0 | A = H, B = OH | carbonyl | H, H | H, H | Me, OH | H, H |
| 1629 | 0 | 1 | A = H, B = OH | carbonyl | H, H | H, H | Me, OH | H, H |

TABLE 1-11-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1630 | 1 | 1 | A = H, B = OH | carbonyl | H, H | Me, OH | H, H | H, H |
| 1631 | 2 | 1 | A = H, B = OH | carbonyl | H, H | Me, OH | H, H | H, H |
| 1632 | 0 | 0 | A = H, B = OH | carbonyl | H, H | Me, OAc | H, H | H, H |
| 1633 | 1 | 0 | A = H, B = OH | carbonyl | H, H | Me, OAc | H, H | H, H |
| 1634 | 2 | 0 | A = H, B = OH | carbonyl | H, H | Me, OAc | H, H | H, H |
| 1635 | 0 | 1 | A = H, B = OH | carbonyl | H, H | Me, OAc | H, H | H, H |
| 1636 | 1 | 1 | A = H, B = OH | carbonyl | H, H | Me, OAc | H, H | H, H |
| 1637 | 2 | 1 | A = H, B = OH | carbonyl | H, H | Me, OAc | H, H | H, H |
| 1638 | 0 | 0 | A = H, B = OH | carbonyl | H, H | Me, OCOn-Bu | H, H | H, H |
| 1639 | 1 | 0 | A = H, B = OH | carbonyl | H, H | Me, OCOn-Bu | H, H | H, H |
| 1640 | 2 | 0 | A = H, B = OH | carbonyl | H, H | Me, OCOn-Bu | H, H | H, H |
| 1641 | 0 | 1 | A = H, B = OH | carbonyl | H, H | Me, OCOn-Bu | H, H | H, H |
| 1642 | 1 | 1 | A = H, B = OH | carbonyl | H, H | Me, OCOn-Bu | H, H | H, H |
| 1643 | 2 | 1 | A = H, B = OH | carbonyl | H, H | Me, OCOn-Bu | H, H | H, H |
| 1644 | 0 | 0 | A = H, B = OH | carbonyl | H, H | Et, OH | H, H | H, H |
| 1645 | 1 | 0 | A = H, B = OH | carbonyl | H, H | Et, OH | H, H | H, H |

TABLE 1-12

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1646 | 0 | 1 | A = H, B = OH | carbonyl | H, H | Et, OH | H, H | H, H |
| 1647 | 1 | 1 | A = H, B = OH | carbonyl | H, H | Et, OH | H, H | H, H |
| 1648 | 0 | 0 | A = H, B = OH | carbonyl | H, H | Pr, OH | H, H | H, H |
| 1649 | 1 | 0 | A = H, B = OH | carbonyl | H, H | Pr, OH | H, H | H, H |
| 1650 | 0 | 1 | A = H, B = OH | carbonyl | H, H | Pr, OH | H, H | H, H |
| 1651 | 1 | 1 | A = H, B = OH | carbonyl | H, H | Pr, OH | H, H | H, H |
| 1652 | 0 | 0 | A = H, B = OH | carbonyl | H, H | $CH_2Ph$, OH | H, H | H, H |
| 1653 | 1 | 0 | A = H, B = OH | carbonyl | H, H | $CH_2Ph$, OH | H, H | H, H |
| 1654 | 0 | 1 | A = H, B = OH | carbonyl | H, H | $CH_2Ph$, OH | H, H | H, H |
| 1655 | 1 | 1 | A = H, B = OH | carbonyl | H, H | $CH_2Ph$, OH | H, H | H, H |
| 1656 | 0 | 0 | A = H, B = OH | carbonyl | H, H | Me, $CH_2OH$ | H, H | H, H |
| 1657 | 1 | 0 | A = H, B = OH | carbonyl | H, H | Me, $CH_2OH$ | H, H | H, H |
| 1658 | 0 | 1 | A = H, B = OH | carbonyl | H, H | Me, $CH_2OH$ | H, H | H, H |
| 1659 | 1 | 1 | A = H, B = OH | carbonyl | H, H | Me, $CH_2OH$ | H, H | H, H |
| 1660 | 0 | 1 | A = H, B = OH | carbonyl | H, H | H, OMe | H, H | H, H |
| 1661 | 1 | 1 | A = H, B = OH | carbonyl | H, H | H, OMe | H, H | H, H |
| 1662 | 0 | 1 | A = H, B = OH | carbonyl | H, H | H, OEt | H, H | H, H |
| 1663 | 1 | 1 | A = H, B = OH | carbonyl | H, H | H, OEt | H, H | H, H |
| 1664 | 0 | 1 | A = H, B = OH | carbonyl | H, H | H, SMe | H, H | H, H |
| 1665 | 1 | 1 | A = H, B = OH | carbonyl | H, H | H, SMe | H, H | H, H |
| 1666 | 0 | 1 | A = H, B = OH | carbonyl | H, H | H, tBu | H, H | H, H |
| 1667 | 1 | 1 | A = H, B = OH | carbonyl | H, H | H, tBu | H, H | H, H |
| 1668 | 0 | 1 | A = H, B = OH | carbonyl | H, H | H, allyl | H, H | H, H |
| 1669 | 1 | 1 | A = H, B = OH | carbonyl | H, H | H, allyl | H, H | H, H |
| 1670 | 0 | 0 | A = H, B = OH | carbonyl | H, H | H, H | H, Me | H, H |
| 1671 | 1 | 0 | A = H, B = OH | carbonyl | H, H | H, H | H, Me | H, H |
| 1672 | 0 | 0 | A = H, B = OH | carbonyl | H, H | H, H | H, Et | H, H |
| 1673 | 1 | 0 | A = H, B = OH | carbonyl | H, H | H, H | H, Et | H, H |
| 1674 | 0 | 0 | A = H, B = OH | carbonyl | H, H | H, H | H, Pr | H, H |
| 1675 | 1 | 0 | A = H, B = OH | carbonyl | H, H | H, H | H, Pr | H, H |
| 1676 | 0 | 1 | A = H, B = OH | carbonyl | H, H | H, H | H, Me | H, H |
| 1677 | 1 | 1 | A = H, B = OH | carbonyl | H, H | H, H | H, Me | H, H |
| 1678 | 0 | 1 | A = H, B = OH | carbonyl | H, H | H, H | H, Et | H, H |
| 1679 | 1 | 1 | A = H, B = OH | carbonyl | H, H | H, H | H, Et | H, H |
| 1680 | 0 | 1 | A = H, B = OH | carbonyl | H, H | H, H | H Pr | H, H |
| 1681 | 1 | 1 | A = H, B = OH | carbonyl | H, H | H, H | H, Pr | H, H |
| 1682 | 0 | 1 | A = H, B = OH | carbonyl | H, H | H, H | H, H | H, Me |
| 1683 | 1 | 1 | A = H, B = OH | carbonyl | H, H | H, H | H, H | H, Me |
| 1684 | 0 | 1 | A = H, B = OH | carbonyl | H, H | H, H | H, H | H, Et |
| 1685 | 1 | 1 | A = H, B = OH | carbonyl | H, H | H, H | H, H | H, Et |
| 1686 | 0 | 1 | A = H, B = OH | carbonyl | H, H | H, H | H, H | H, tBu |
| 1687 | 1 | 1 | A = H, B = OH | carbonyl | H, H | H, H | H, H | H, tBu |

TABLE 1-13

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1701 | 0 | 0 | A = OH, B = H | OH, H | H, H | H, H | H, H | H, H |
| 1702 | 1 | 0 | A = OH, B = H | OH, H | H, H | H, H | H, H | H, H |
| 1703 | 2 | 0 | A = OH, B = H | OH, H | H, H | H, H | H, H | H, H |
| 1704 | 0 | 1 | A = OH, B = H | OH, H | H, H | H, H | H, H | H, H |
| 1705 | 1 | 1 | A = OH, B = H | OH, H | H, H | H, H | H, H | H, H |
| 1706 | 2 | 1 | A = OH, B = H | OH, H | H, H | H, H | H, H | H, H |
| 1707 | 0 | 2 | A = OH, B = H | OH, H | H, H | H, H | H, H | H, H |
| 1708 | 1 | 2 | A = OH, B = H | OH, H | H, H | H, H | H, H | H, H |
| 1709 | 2 | 2 | A = OH, B = H | OH, H | H, H | H, H | H, H | H, H |
| 1710 | 0 | 0 | A = OH, B = H | OH, H | H, H | H, Me | H, H | H, H |
| 1711 | 1 | 0 | A = OH, B = H | OH, H | H, H | H, Me | H, H | H, H |
| 1712 | 0 | 0 | A = OH, B = H | OH, H | H, H | H, Et | H, H | H, H |
| 1713 | 1 | 0 | A = OH, B = H | OH, H | H, H | H, Et | H, H | H, H |
| 1714 | 0 | 0 | A = OH, B = H | OH, H | H, H | H, Pr | H, H | H, H |
| 1715 | 1 | 0 | A = OH, B = H | OH, H | H, H | H, Pr | H, H | H, H |
| 1716 | 0 | 0 | A = OH, B = H | OH, H | H, H | Me, Me | H, H | H, H |
| 1717 | 1 | 0 | A = OH, B = H | OH, H | H, H | Me, Me | H, H | H, H |
| 1718 | 0 | 1 | A = OH, B = H | OH, H | H, H | H, Me | H, H | H, H |
| 1719 | 1 | 1 | A = OH, B = H | OH, H | H, H | H, Me | H, H | H, H |
| 1720 | 0 | 1 | A = OH, B = H | OH, H | H, H | H, Et | H, H | H, H |
| 1721 | 1 | 1 | A = OH, B = H | OH, H | H, H | H, Et | H, H | H, H |
| 1722 | 0 | 1 | A = OH, B = H | OH, H | H, H | H, Pr | H, H | H, H |
| 1723 | 1 | 1 | A = OH, B = H | OH, H | H, H | H, Pr | H, H | H, H |
| 1724 | 0 | 1 | A = OH, B = H | OH, H | H, H | Me, Me | H, H | H, H |
| 1725 | 1 | 1 | A = OH, B = H | OH, H | H, H | Me, Me | H, H | H, H |
| 1726 | 0 | 0 | A = OH, B = H | OH, H | H, H | Me, OH | H, H | H, H |
| 1727 | 1 | 0 | A = OH, B = H | OH, H | H, H | Me, OH | H, H | H, H |
| 1728 | 2 | 0 | A = OH, B = H | OH, H | H, H | Me, OH | H, H | H, H |
| 1729 | 0 | 1 | A = OH, B = H | OH, H | H, H | Me, 0H | H, H | H, H |
| 1730 | 1 | 1 | A = OH, B = H | OH, H | H, H | Me, OH | H, H | H, H |
| 1731 | 2 | 1 | A = OH, B = H | OH, H | H, H | Me, OH | H, H | H, H |
| 1732 | 0 | 0 | A = OH, B = H | OH, H | H, H | Me, OAc | H, H | H, H |
| 1733 | 1 | 0 | A = OH, B = H | OH, H | H, H | Me, OAc | H, H | H, H |
| 1734 | 2 | 0 | A = OH, B = H | OH, H | H, H | Me, OAc | H, H | H, H |
| 1735 | 0 | 1 | A = OH, B = H | OH, H | H, H | Me, OAc | H, H | H, H |
| 1736 | 1 | 1 | A = OH, B = H | OH, H | H, H | Me, OAc | H, H | H, H |
| 1737 | 2 | 1 | A = OH, B = H | OH, H | H, H | Me, OAc | H, H | H, H |
| 1738 | 0 | 0 | A = OH, B = H | OH, H | H, H | Me, OCOn-Bu | H, H | H, H |
| 1739 | 1 | 0 | A = OH, B = H | OH, H | H, H | Me, OCOn-Bu | H, H | H, H |
| 1740 | 2 | 0 | A = OH, B = H | OH, H | H, H | Me, OCOn-Bu | H, H | H, H |
| 1741 | 0 | 1 | A = OH, B = H | OH, H | H, H | Me, OCOn-Bu | H, H | H, H |
| 1742 | 1 | 1 | A = OH, B = H | OH, H | H, H | Me, OCOn-Bu | H, H | H, H |
| 1743 | 2 | 1 | A = OH, B = H | OH, H | H, H | Me, OCOn-Bu | H, H | H, H |
| 1744 | 0 | 0 | A = OH, B = H | OH, H | H, H | Et, OH | H, H | H, H |
| 1745 | 1 | 0 | A = OH, B = H | OH, H | H, H | Et, OH | H, H | H, H |

TABLE 1-14

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1746 | 0 | 1 | A = OH, B = H | OH, H | H, H | Et, OH | H, H | H, H |
| 1747 | 1 | 1 | A = OH, B = H | OH, H | H, H | Et, OH | H, H | H, H |
| 1748 | 0 | 0 | A = OH, B = H | OH, H | H, H | Pr, OH | H, H | H, H |
| 1749 | 1 | 0 | A = OH, B = H | OH, H | H, H | Pr, OH | H, H | H, H |
| 1750 | 0 | 1 | A = OH, B = H | OH, H | H, H | Pr, OH | H, H | H, H |
| 1751 | 1 | 1 | A = OH, B = H | OH, H | H, H | Pr, OH | H, H | H, H |
| 1752 | 0 | 0 | A = OH, B = H | OH, H | H, H | $CH_2Ph$, OH | H, H | H, H |
| 1753 | 1 | 0 | A = OH, B = H | OH, H | H, H | $CH_2Ph$, OH | H, H | H, H |
| 1754 | 0 | 1 | A = OH, B = H | OH, H | H, H | $CH_2Ph$, OH | H, H | H, H |
| 1755 | 1 | 1 | A = OH, B = H | OH, H | H, H | $CH_2Ph$, OH | H, H | H, H |
| 1756 | 0 | 0 | A = OH, B = H | OH, H | H, H | Me, $CH_2OH$ | H, H | H, H |
| 1757 | 1 | 0 | A = OH, B = H | OH, H | H, H | Me, $CH_2OH$ | H, H | H, H |
| 1758 | 0 | 1 | A = OH, B = H | OH, H | H, H | Me, $CH_2OH$ | H, H | H, H |

TABLE 1-14-continued

Structure of Compound: formula [1], Z = [1a]

| Comp. No. | n | m | A, B | X, Y | R1, R2 | R3, R4 | R5, R6 | R7, R8 |
|---|---|---|---|---|---|---|---|---|
| 1759 | 1 | 1 | A = OH, B = H | OH, H | H, H | Me, CH₂OH | H, H | H, H |
| 1760 | 0 | 1 | A = OH, B = H | OH, H | H, H | H, OMe | H, H | H, H |
| 1761 | 1 | 1 | A = OH, B = H | OH, H | H, H | H, OMe | H, H | H, H |
| 1762 | 0 | 1 | A = OH, B = H | OH, H | H, H | H, OEt | H, H | H, H |
| 1763 | 1 | 1 | A = OH, B = H | OH, H | H, H | H, OEt | H, H | H, H |
| 1764 | 0 | 1 | A = OH, B = H | OH, H | H, H | H, SMe | H, H | H, H |
| 1765 | 1 | 1 | A = OH, B = H | OH, H | H, H | H, SMe | H, H | H, H |
| 1766 | 0 | 1 | A = OH, B = H | OH, H | H, H | H, tBu | H, H | H, H |
| 1767 | 1 | 1 | A = OH, B = H | OH, H | H, H | H, tBu | H, H | H, H |
| 1768 | 0 | 1 | A = OH, B = H | OH, H | H, H | H, allyl | H, H | H, H |
| 1769 | 1 | 1 | A = OH, B = H | OH, H | H, H | H, allyl | H, H | H, H |
| 1770 | 0 | 0 | A = OH, B = H | OH, H | H, H | H, H | H, Me | H, H |
| 1771 | 1 | 0 | A = OH, B = H | OH, H | H, H | H, H | H, Me | H, H |
| 1772 | 0 | 0 | A = OH, B = H | OH, H | H, H | H, H | H, Et | H, H |
| 1773 | 1 | 0 | A = OH, B = H | OH, H | H, H | H, H | H, Et | H, H |
| 1774 | 0 | 0 | A = OH, B = H | OH, H | H, H | H, H | H, Pr | H, H |
| 1775 | 1 | 0 | A = OH, B = H | OH, H | H, H | H, H | H, Pr | H, H |
| 1776 | 0 | 1 | A = OH, B = H | OH, H | H, H | H, H | H, Me | H, H |
| 1777 | 1 | 1 | A = OH, B = H | OH, H | H, H | H, H | H, Me | H, H |
| 1778 | 0 | 1 | A = OH, B = H | OH, H | H, H | H, H | H, Et | H, H |
| 1779 | 1 | 1 | A = OH, B = H | OH, H | H, H | H, H | H, Et | H, H |
| 1780 | 0 | 1 | A = OH, B = H | OH, H | H, H | H, H | H, Pr | H, H |
| 1781 | 1 | 1 | A = OH, B = H | OH, H | H, H | H, H | H, Pr | H, H |
| 1782 | 0 | 1 | A = OH, B = H | OH, H | H, H | H, H | H, H | H, Me |
| 1783 | 1 | 1 | A = OH, B = H | OH, H | H, H | H, H | H, H | H, Me |
| 1784 | 0 | 1 | A = OH, B = H | OH, H | H, H | H, H | H, H | H, Et |
| 1785 | 1 | 1 | A = OH, B = H | OH, H | H, H | H, H | H, H | H, Et |
| 1786 | 0 | 1 | A = OH, B = H | OH, H | H, H | H, H | H, H | H, tBu |
| 1787 | 1 | 1 | A = OH, B = H | OH, H | H, H | H, H | H, H | H, tBu |

TABLE 2-1

Structure of Compound: formula [1], Z = [1b]

| Comp. No | n | m | A, B | X, Y | R1, R2 | R7, R8 | R9 | R10 |
|---|---|---|---|---|---|---|---|---|
| 2101 | 0 | 0 | double bond | carbonyl | H, H | H, H | H | H |
| 2102 | 1 | 0 | double bond | carbonyl | H, H | H, H | H | H |
| 2103 | 2 | 0 | double bond | carbonyl | H, H | H, H | H | H |
| 2104 | 0 | 0 | double bond | carbonyl | H, H | H, H | Me | H |
| 2105 | 1 | 0 | double bond | carbonyl | H, H | H, H | Me | H |
| 2106 | 2 | 0 | double bond | carbonyl | H, H | H, H | Me | H |
| 2107 | 0 | 0 | double bond | carbonyl | H, H | H, H | Pentyl | H |
| 2108 | 1 | 0 | double bond | carbonyl | H, H | H, H | Pentyl | H |
| 2109 | 2 | 0 | double bond | carbonyl | H, H | H, H | Pentyl | H |
| 2110 | 0 | 0 | double bond | carbonyl | H, H | H, H | H | Me |
| 2111 | 1 | 0 | double bond | carbonyl | H, H | H, H | H | Me |
| 2112 | 2 | 0 | double bond | carbonyl | H, H | H, H | H | Me |
| 2113 | 0 | 0 | double bond | carbonyl | H, H | H, H | Me | Me |
| 2114 | 1 | 0 | double bond | carbonyl | H, H | H, H | Me | Me |
| 2115 | 2 | 0 | double bond | carbonyl | H, H | H, H | Me | Me |
| 2116 | 0 | 0 | double bond | carbonyl | H, H | Me, Me | H | H |
| 2117 | 1 | 0 | double bond | carbonyl | H, H | Me, Me | H | H |
| 2118 | 2 | 0 | double bond | carbonyl | H, H | Me, Me | H | H |
| 2119 | 0 | 0 | double bond | carbonyl | H, H | H, H | H | OMe |
| 2120 | 1 | 0 | double bond | carbonyl | H, H | H, H | H | OMe |
| 2121 | 2 | 0 | double bond | carbonyl | H, H | H, H | H | OMe |
| 2122 | 0 | 0 | double bond | carbonyl | H, H | H, H | H | OEt |
| 2123 | 1 | 0 | double bond | carbonyl | H, H | H, H | H | OEt |
| 2124 | 2 | 0 | double bond | carbonyl | H, H | H, H | H | OEt |
| 2125 | 0 | 1 | double bond | carbonyl | H, H | H, H | H | H |
| 2126 | 1 | 1 | double bond | carbonyl | H, H | H, H | H | H |
| 2127 | 2 | 1 | double bond | carbonyl | H, H | H, H | H | H |
| 2128 | 0 | 1 | double bond | carbonyl | H, H | H, H | H | Me |
| 2129 | 1 | 1 | double bond | carbonyl | H, H | H, H | H | Me |

TABLE 2-1-continued

Structure of Compound: formula [1], Z = [1b]

| Comp. No | n | m | A, B | X, Y | R1, R2 | R7, R8 | R9 | R10 |
|---|---|---|---|---|---|---|---|---|
| 2130 | 2 | 1 | double bond | carbonyl | H, H | H, H | H | Me |
| 2131 | 0 | 1 | double bond | carbonyl | H, H | Me, Me | H | H |
| 2132 | 1 | 1 | double bond | carbonyl | H, H | Me, Me | H | H |
| 2133 | 2 | 1 | double bond | carbonyl | H, H | Me, Me | H | H |
| 2134 | 0 | 1 | double bond | carbonyl | H, H | Me, Me | Me | H |
| 2135 | 1 | 1 | double bond | carbonyl | H, H | Me, Me | Me | H |
| 2136 | 2 | 1 | double bond | carbonyl | H, H | Me, Me | Me | H |
| 2137 | 0 | 1 | dduble bond | carbonyl | H, H | H, H | H | OEt |
| 2138 | 1 | 1 | double bond | carbonyl | H, H | H, H | H | OEt |
| 2139 | 2 | 1 | double bond | carbonyl | H, H | H, H | H | OEt |
| 2140 | 0 | 2 | double bond | carbonyl | H, H | H, H | H | H |
| 2141 | 1 | 2 | double bond | carbonyl | H, H | H, H | H | H |
| 2142 | 2 | 2 | double bond | carbonyl | H, H | H, H | H | H |

TABLE 2-2

Structure of Compound: formula [1], Z = [1b]

| Comp. No. | n | m | A, B | X, Y | R1, R2 | R7, R8 | R9 | R10 |
|---|---|---|---|---|---|---|---|---|
| 2201 | 0 | 0 | A = OH, B = H | carbonyl | H, H | H, H | H | H |
| 2202 | 1 | 0 | A = OH, B = H | carbonyl | H, H | H, H | H | H |
| 2203 | 2 | 0 | A = OH, B = H | carbonyl | H, H | H, H | H | H |
| 2204 | 0 | 0 | A = OH, B = H | carbonyl | H, H | H, H | H | H |
| 2205 | 1 | 0 | A = OH, B = H | carbonyl | H, H | H, H | H | H |
| 2206 | 2 | 0 | A = OH, B = H | carbonyl | H, H | H, H | H | H |
| 2207 | 0 | 0 | A = OH, B = H | carbonyl | H, H | H, H | Pentyl | H |
| 2208 | 1 | 0 | A = OH, B = H | carbonyl | H, H | H, H | Pentyl | H |
| 2209 | 2 | 0 | A = OH, B = H | carbonyl | H, H | H, H | Pentyl | H |
| 2210 | 0 | 0 | A = OH, B = H | carbonyl | H, H | H, H | Me | H |
| 2211 | 1 | 0 | A = OH, B = H | carbonyl | H, H | H, H | Me | H |
| 2212 | 2 | 0 | A = OH, B = H | carbonyl | H, H | H, H | Me | H |
| 2213 | 0 | 0 | A = OH, B = H | carbonyl | H, H | H, H | Me | Me |
| 2214 | 1 | 0 | A = OH, B = H | carbonyl | H, H | H, H | Me | Me |
| 2215 | 2 | 0 | A = OH, B = H | carbonyl | H, H | H, H | Me | Me |
| 2216 | 0 | 0 | A = OH, B = H | carbonyl | H, H | Me, Me | H | H |
| 2217 | 1 | 0 | A = OH, B = H | carbonyl | H, H | Me, Me | H | H |
| 2218 | 2 | 0 | A = OH, B = H | carbonyl | H, H | Me, Me | H | H |
| 2219 | 0 | 0 | A = OH, B = H | carbonyl | H, H | H, H | H | OMe |
| 2220 | 1 | 0 | A = OH, B = H | carbonyl | H, H | H, H | H | OMe |
| 2221 | 2 | 0 | A = OH, B = H | carbonyl | H, H | H, H | H | OMe |
| 2222 | 0 | 0 | A = OH, B = H | carbonyl | H, H | H, H | H | OEt |
| 2223 | 1 | 0 | A = OH, B = H | carbonyl | H, H | H, H | H | OEt |
| 2224 | 2 | 0 | A = OH, B = H | carbonyl | H, H | H, H | H | OEt |
| 2225 | 0 | 1 | A = OH, B = H | carbonyl | H, H | H, H | H | H |
| 2226 | 1 | 1 | A = OH, B = H | carbonyl | H, H | H, H | H | H |
| 2227 | 2 | 1 | A = OH, B = H | carbonyl | H, H | H, H | H | H |
| 2228 | 0 | 1 | A = OH, B = H | carbonyl | H, H | H, H | H | Me |
| 2229 | 1 | 1 | A = OH, B = H | carbonyl | H, H | H, H | H | Me |
| 2230 | 2 | 1 | A = OH, B = H | carbonyl | H, H | H, H | H | Me |
| 2231 | 0 | 1 | A = OH, B = H | carbonyl | H, H | Me, Me | H | H |
| 2232 | 1 | 1 | A = OH, B = H | carbonyl | H, H | Me, Me | H | H |
| 2233 | 2 | 1 | A = OH, B = H | carbonyl | H, H | Me, Me | H | H |
| 2234 | 0 | 1 | A = OH, B = H | carbonyl | H, H | Me, Me | Me | H |
| 2235 | 1 | 1 | A = OH, B = H | carbonyl | H, H | Me, Me | Me | H |
| 2236 | 2 | 1 | A = OH, B = H | carbonyl | H, H | Me, Me | Me | H |
| 2237 | 0 | 1 | A = OH, B = H | carbonyl | H, H | H, H | H | OEt |
| 2238 | 1 | 1 | A = OH, B = H | carbonyl | H, H | H, H | H | OEt |
| 2239 | 2 | 1 | A = OH, B = H | carbonyl | H, H | H, H | H | OEt |
| 2240 | 0 | 2 | A = OH, B = H | carbonyl | H, H | H, H | H | H |
| 2241 | 1 | 2 | A = OH, B = H | carbonyl | H, H | H, H | H | H |
| 2242 | 2 | 2 | A = OH, B = H | carbonyl | H, H | H, H | H | H |

TABLE 2-3

Structure of Compound: formula [1], Z = [1b]

| Comp. No. | n | m | A, B | X, Y | R1, R2 | R7, R8 | R9 | R10 |
|---|---|---|---|---|---|---|---|---|
| 2301 | 0 | 0 | double bond | H, OH | H, H | H, H | H | H |
| 2302 | 1 | 0 | double bond | H, OH | H, H | H, H | H | H |
| 2303 | 2 | 0 | double bond | H, OH | H, H | H, H | H | H |
| 2304 | 0 | 0 | double bond | H, OH | H, H | H, H | H | H |
| 2305 | 1 | 0 | double bond | H, OH | H, H | H, H | H | H |
| 2306 | 2 | 0 | double bond | H, OH | H, H | H, H | H | H |
| 2307 | 0 | 0 | double bond | H, OH | H, H | H, H | Pentyl | H |
| 2308 | 1 | 0 | double bond | H, OH | H, H | H, H | Pentyl | H |
| 2309 | 2 | 0 | double bond | H, OH | H, H | H, H | Pentyl | H |
| 2310 | 0 | 0 | double bond | H, OH | H, H | H, H | Me | H |
| 2311 | 1 | 0 | double bond | H, OH | H, H | H, H | Me | H |
| 2312 | 2 | 0 | double bond | H, OH | H, H | H, H | Me | H |
| 2313 | 0 | 0 | double bond | H, OH | H, H | H, H | Me | Me |
| 2314 | 1 | 0 | double bond | H, OH | H, H | H, H | Me | Me |
| 2315 | 2 | 0 | double bond | H, OH | H, H | H, H | Me | Me |
| 2316 | 0 | 0 | double bond | H, OH | H, H | Me, Me | H | H |
| 2317 | 1 | 0 | double bond | H, OH | H, H | Me, Me | H | H |
| 2318 | 2 | 0 | double bond | H, OH | H, H | Me, Me | H | H |
| 2319 | 0 | 0 | double bond | H, OH | H, H | H, H | H | OMe |
| 2320 | 1 | 0 | double bond | H, OH | H, H | H, H | H | OMe |
| 2321 | 2 | 0 | double bond | H, OH | H, H | H, H | H | OMe |
| 2322 | 0 | 0 | double bond | H, OH | H, H | H, H | H | OEt |
| 2323 | 1 | 0 | double bond | H, OH | H, H | H, H | H | OEt |
| 2324 | 2 | 0 | double bond | H, OH | H, H | H, H | H | OEt |
| 2325 | 0 | 1 | double bond | H, OH | H, H | H, H | H | H |
| 2326 | 1 | 1 | double bond | H, OH | H, H | H, H | H | H |
| 2327 | 2 | 1 | double bond | H, OH | H, H | H, H | H | H |
| 2328 | 0 | 1 | double bond | H, OH | H, H | H, H | H | Me |
| 2329 | 1 | 1 | double bond | H, OH | H, H | H, H | H | Me |
| 2330 | 2 | 1 | double bond | H, OH | H, H | H, H | H | Me |
| 2331 | 0 | 1 | double bond | H, OH | H, H | Me, Me | H | H |
| 2332 | 1 | 1 | double bond | H, OH | H, H | Me, Me | H | H |
| 2333 | 2 | 1 | double bond | H, OH | H, H | Me, Me | H | H |
| 2334 | 0 | 1 | double bond | H, OH | H, H | Me, Me | Me | H |
| 2335 | 1 | 1 | double bond | H, OH | H, H | Me, Me | Me | H |
| 2336 | 2 | 1 | double bond | H, OH | H, H | Me, Me | Me | H |
| 2337 | 0 | 1 | double bond | H, OH | H, H | H, H | H | OEt |
| 2338 | 1 | 1 | double bond | H, OH | H, H | H, H | H | OEt |
| 2339 | 2 | 1 | double bond | H, OH | H, H | H, H | H | OEt |
| 2340 | 0 | 2 | double bond | H, OH | H, H | H, H | H | H |
| 2341 | 1 | 2 | double bond | H, OH | H, H | H, H | H | H |
| 2342 | 2 | 2 | double bond | H, OH | H, H | H, H | H | H |

The production of a vitamin $D_3$ derivative expressed by the above formula [1] can be carried out, for example, by reacting an aldehyde expressed by the following formula [2] with a compound expressed by the following formula [3] or the following formula [4] in aldol reaction in the presence of a basic catalyst and optionally combining reactions of dehydration, deprotection, reduction, isomerization, etc.

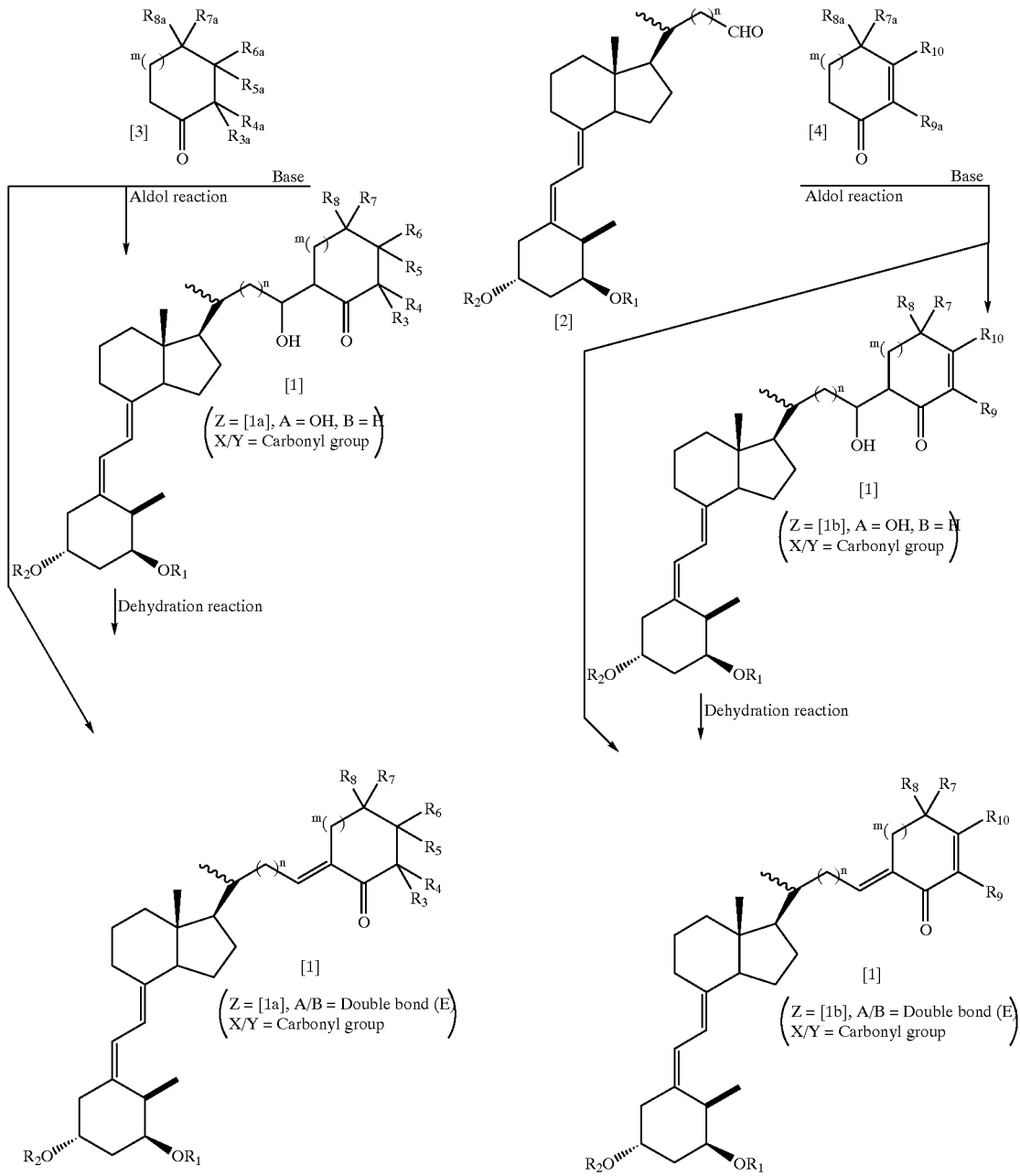

[wherein, $R_1$, $R_2$, $R_{10}$, n and m are same as defined in the above formula [1]; $R_{3a}$ and $R_{4a}$ are identical to or different from each other, and they are each a hydrogen atom, a hydroxyl group, a protected hydroxyl group, a $C_2$–$C_8$ acyloxy group, a $C_1$–$C_7$ alkyloxy group, a $C_1$–$C_6$ alkylthio group or a $C_1$–$C_7$ alkyl group which is optionally substituted with a hydroxyl group, a protected hydroxyl group, a $C_2$–$C_8$ acyloxy group or a $C_1$–$C_7$ alkyloxy group; $R_{5a}$, $R_{6a}$, $R_{7a}$ and $R_{8a}$ are same to or different from each other, and they are each a hydrogen atom, a hydroxyl group, a protected hydroxyl group, a $C_1$–$C_7$ alkyl group or a $C_2$–$C_8$ acyloxy group; $R_{9a}$ is a hydrogen atom, a hydroxyl group, a protected hydroxyl group, a $C_1$–$C_7$ alkyl group or a $C_1$–$C_6$ alkylthio group].

A vitamin $D_3$ derivative expressed by [1] (Z is [1a]; A is a hydroxyl group and B is a hydrogen atom; X and Y together express a carbonyl group in cooperation with the carbon atom to which they are bonded) or [1] (Z is [1b]; A is a hydroxyl group and B is a hydrogen atom; X and Y together express a carbonyl group in cooperation with the carbon atom to which they are bonded), or a vitamin $D_3$ derivative expressed by [1] (Z is [1a]; A and B together express a double bond (E-configuration) as a whole; X and Y together express a carbonyl group in cooperation with the carbon atom to which they are bonded) or [1] (Z is [1b]; A and B together express a double bond (E-configuration) as a whole; X and Y together express a carbonyl group in cooperation with the carbon atom to which they are bonded) is obtained through aldol reaction between an aldehyde expressed by the above formula [2] and a compound expressed by the above formula [3] or formula [4], and then optionally through deprotection in the case where $R_{3a}$ to $R_{9a}$ are each a protected hydroxyl group.

The vitamin $D_3$ derivatives expressed by [1] (Z is [1a]; A is a hydroxyl group and B is a hydrogen atom; X and Y together express a carbonyl group in cooperation with the carbon atom to which they are bonded) or [1] (Z is [1b]; A is a hydroxyl group and B is a hydrogen atom; X and Y together express a carbonyl group in cooperation with the carbon atom to which they are bonded) can be converted into the vitamin $D_3$ derivatives expressed by [1] (Z is [1a]; A and B together express a double bond (E-configuration) as a whole; X and Y together express a carbonyl group in cooperation with the carbon atom to which they are bonded) or [1] (Z is [1b]; A and B together express a double bond (E-configuration) as a whole; X and Y together express a carbonyl group in cooperation with the carbon atom to which they are bonded) by subjecting them to dehydration reactions.

Examples of the basic catalyst in the above aldol reaction include, for example, an inorganic basic catalyst such as potassium carbonate, lithium hydroxide, sodium hydroxide, potassium hydroxide, calcium hydroxide or sodium hydride, an organic basic catalyst such as 1,8-diazabicyclo[5.4.0]undecene (DBU), and an organo metallic basic catalyst such as lithium diisopropylamide, lithium hexamethyldisilylamide or sodium hexamethyldisilylamide. Especially, sodium hydroxide, potassium hydroxide, lithium diisopropylamide or lithium lo hexamethyldisilylamide is cited as a preferable example. The amount of the basic catalyst to be used is 0.1–10 equivalent, preferably 0.5–3 equivalent based on the aldehyde to be used as a raw material. Further, an additive for stimulating the reaction is optionally added to the reaction system. Here, an aldehyde expressed by the above formula [2] carries out stoichiometrically equimolar reaction with a compound expressed by the above formula [3] or [4], but it is preferable that either of which is easier in availability is used in a little excess than the other for certainly completing the reaction.

Examples of the organic solvent to be used in the aldol reaction include an alcoholic solvent such as methanol or ethanol, a halogen containing solvent such as methylene chloride, chloroform or carbon tetrachloride, a hydrocarbon solvent such as hexane or toluene, an ether solvent such as tetrahydrofuran or dioxane, a water-soluble solvent such as N,N-dimethylformamide or acetonitrile, their mixture, etc. The solvent can be selected considering the solubility and the reactivity of a compound. As for reaction temperature, a temperature in the range from −78° C. to the boiling point of the solvent is generally used. Reaction time generally depends on the basic catalyst, the reaction solvent and the reaction temperature used. It is commonly preferable that the reaction is continued until either of the compound expressed by the above formula [3] or [4], or the aldehyde expressed by the above formula [2] disappears when determined by using an analytical means such as thin layer chromatography.

Examples of the dehydrating agent to be used in the dehydration reaction include an acid such as potassium hydrogensulfate, oxalic acid, p-toluenesulfonic acid, iodine or anhydrous copper sulfate, a halogenating agent such as thionyl chloride or phosphoric acid chloride, a sulfonating agent such as methanesulfonyl chloride, etc. The amount of the agent to be used is 1–10 equivalent, preferably 1–5 equivalent based on an aldol adduct [1] (Z is [1a]; A is a hydroxyl group and B is a hydrogen atom; X and Y together express a carbonyl group in cooperation with the carbon atom to which they are bonded) or [1] (Z is [1b]; A is a hydroxyl group and B is a hydrogen atom; X and Y together express a carbonyl group in cooperation with the carbon atom to which they are bonded).

By reducing the carbonyl group on the side chain of a vitamin $D_3$ derivative thus obtained expressed by [1] (Z is [1a]; A and B together express a double bond (E-configuration) as a whole; X and Y together express a carbonyl group in cooperation with the carbon atom to which they are bonded) or [1] (Z is [1b]; A and B together express a double bond (E-configuration) as a whole; X and Y together express a carbonyl group in cooperation with the carbon atom to which they are bonded), a vitamin $D_3$ derivative expressed by the following formula [1] (Z is [1a]; A and B together express a double bond (E-configuration) as a whole; one of X and Y is a hydrogen atom, and the other is a hydroxyl group) or [1] (Z is [1b]; A and B together express a double bond (E-configuration) as a whole; one of X and Y is a hydrogen atom, and the other is a hydroxyl group) can be obtained.

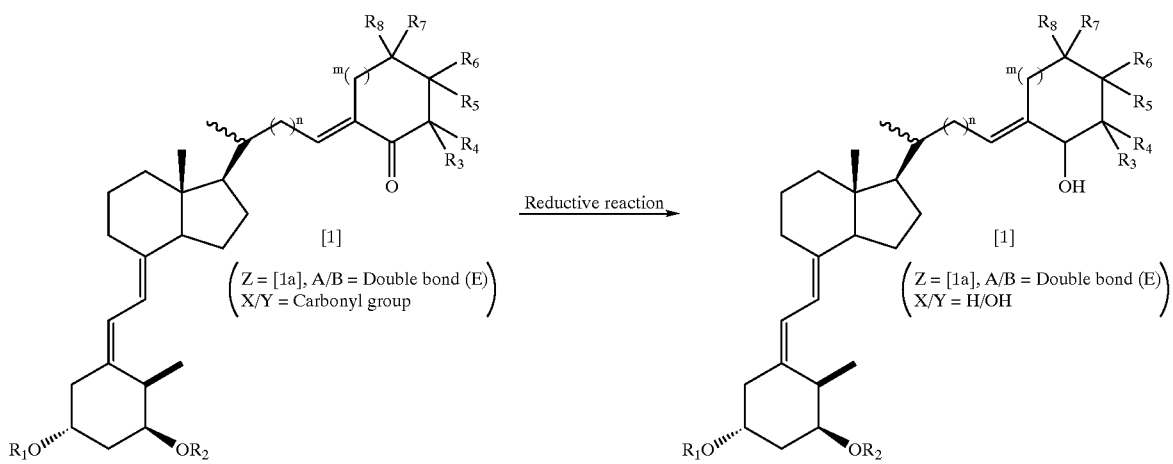

-continued

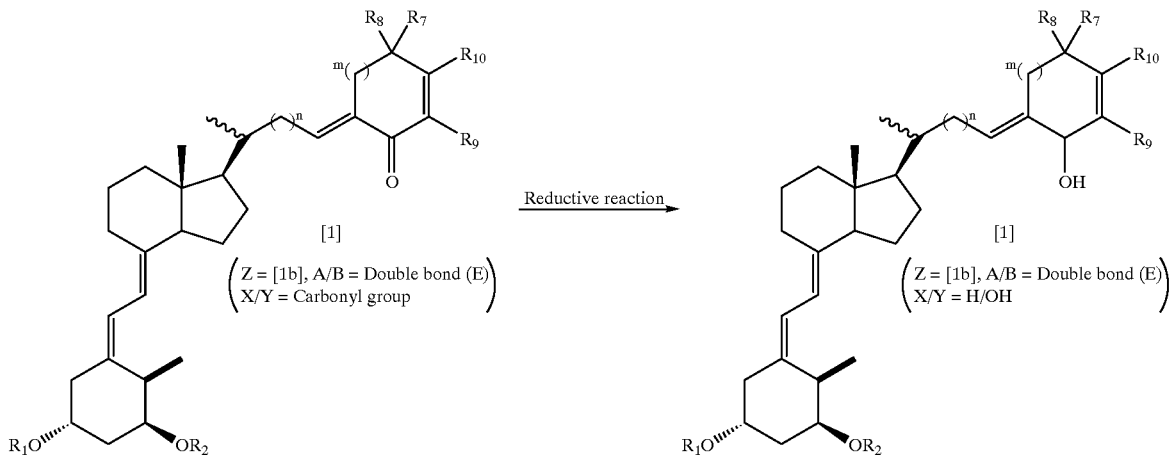

In this reductive reaction, sodium borohydride-cesium chloride, diiIsobutylaluminum hydride (DIBAH), 9-borabicyclo[3.3.1]nonane (9-BBN), lithium n-butylborohydride, K-Selectride®, tri-i-butylaluminium, etc., may be used as a reducing agent.

Similar reductive reaction may be carried out on a vitamin $D_3$ derivative expressed by [1] (Z is [1a]; A is a hydroxyl group and B is a hydrogen atom; X and Y together express a carbonyl group in cooperation with the carbon atom to which they are bonded) or [1] (Z is [1b]; A is a hydroxyl group and B is a hydrogen atom; X and Y together express a carbonyl group in cooperation with the carbon atom to which they are bonded), and in this case, a vitamin $D_3$ derivative expressed by the following formula [1] (Z is [1a]; A is a hydroxyl group and B is a hydrogen atom; one of X and Y is a hydrogen atom, and the other is a hydroxyl group) or [1] (Z is [1b]; A is a hydroxyl group and B is a hydrogen atom; one of X and Y is a hydrogen atom, and the other is a hydroxyl group) can be obtained.

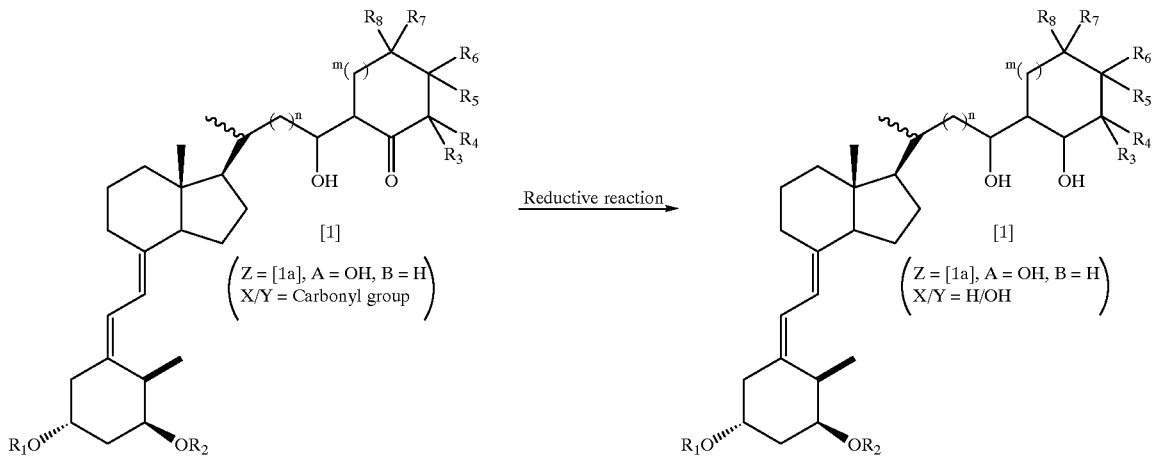

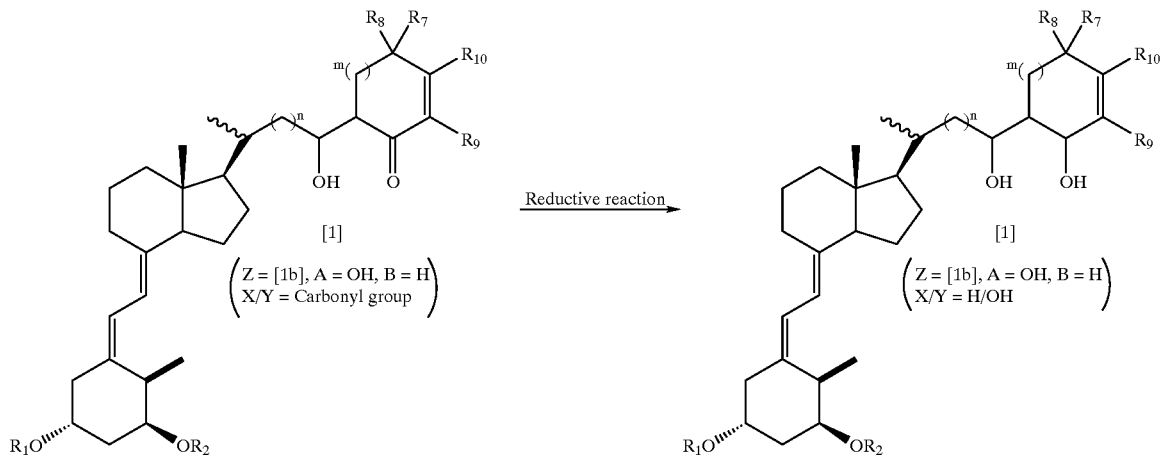

Further, [1] (Z is [1a]; A and B together express a double bond (E-configuration) as a whole; one of X and Y is a hydrogen atom, and the other is a hydroxyl group), which is obtained by the above reductive reaction, can be converted into a vitamin $D_3$ derivative expressed by [1] (Z is [1a]; A is a hydrogen atom and B is a hydroxyl group; X and Y together express a carbonyl group in cooperation with the carbon atom to which they are bonded) by epoxidizing of the double bond at the α, β-position of the ketone on the side chain and subsequently treating the resultant epoxy ring for reductive ring opening reaction, and then carrying out oxidation of secondary hydroxy group.

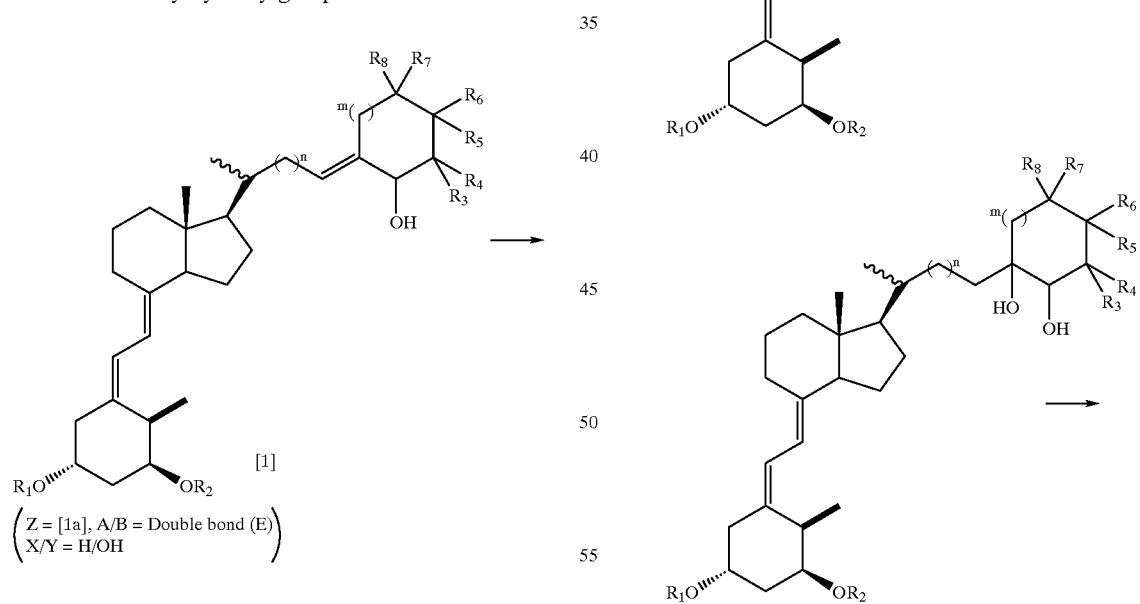

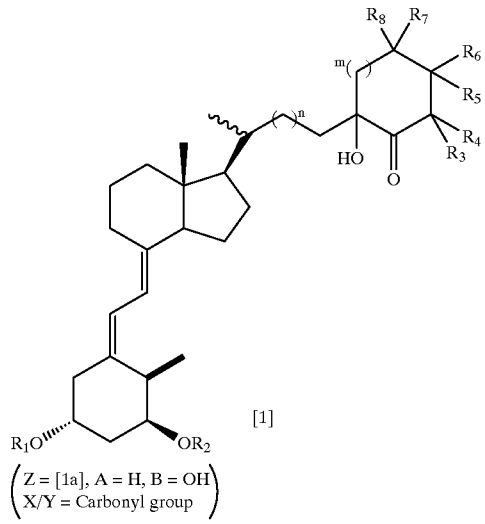

(Z = [1a], A = H, B = OH
X/Y = Carbonyl group) [1]

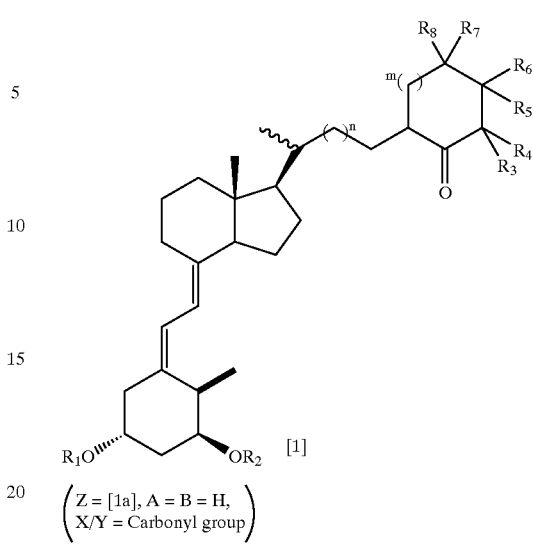

(Z = [1a], A = B = H,
X/Y = Carbonyl group) [1]

Furthermore, as shown below, the reduction of the double bond at the α, β-position of the ketone on the side chain of the above formula [1] (Z is [1]; A and B together express a double bond (E-configuration) as a whole; X and Y together express a carbonyl group in cooperation with the carbon atom to which they are bonded) can obtain a vitamin $D_3$ derivative expressed by the following formula [1] (Z is [1]; both of A and B are each a hydrogen atom; X and Y together express a carbonyl group in cooperation with the carbon atom to which they are bonded).

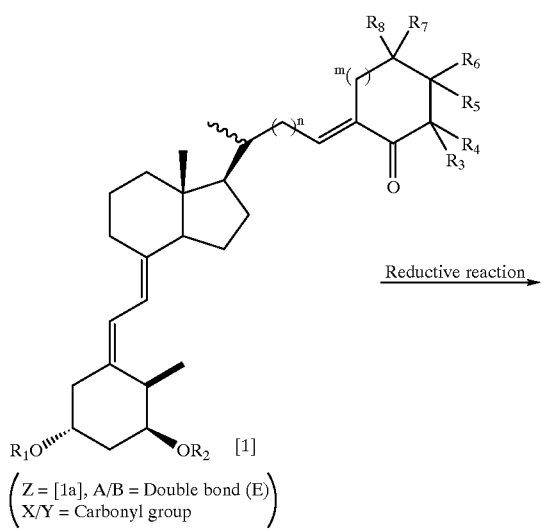

(Z = [1a], A/B = Double bond (E)
X/Y = Carbonyl group) [1]

In this reductive reaction, reduction with sodium borohydride, $Na_2S_2O_4$, NaHTe, tri-n-butyltin hydride, K-Selectride® or lithium aluminum hydride-cuprous iodide (l), or Birch reduction, etc., is applicable.

Further, as shown below, the isomerization of the double bond at the α, β-position of the ketone on the side chain of the above formula [1] (Z is [1]; A and B together express a double bond (E-configuration) as a whole; X and Y together express a carbonyl group in cooperation with the carbon atom to which they are bonded) can obtain a vitamin $D_3$ derivative expressed by the following formula [1] (Z is [1c]; X and Y together express a carbonyl group in cooperation with the carbon atom to which they are bonded) or a vitamin $D_3$ derivative expressed by the following formula [1] (Z is [1]; A and B together express a double bond (Z-configuration) as a whole; X and Y together express a carbonyl group in cooperation with the carbon atom to which they are bonded).

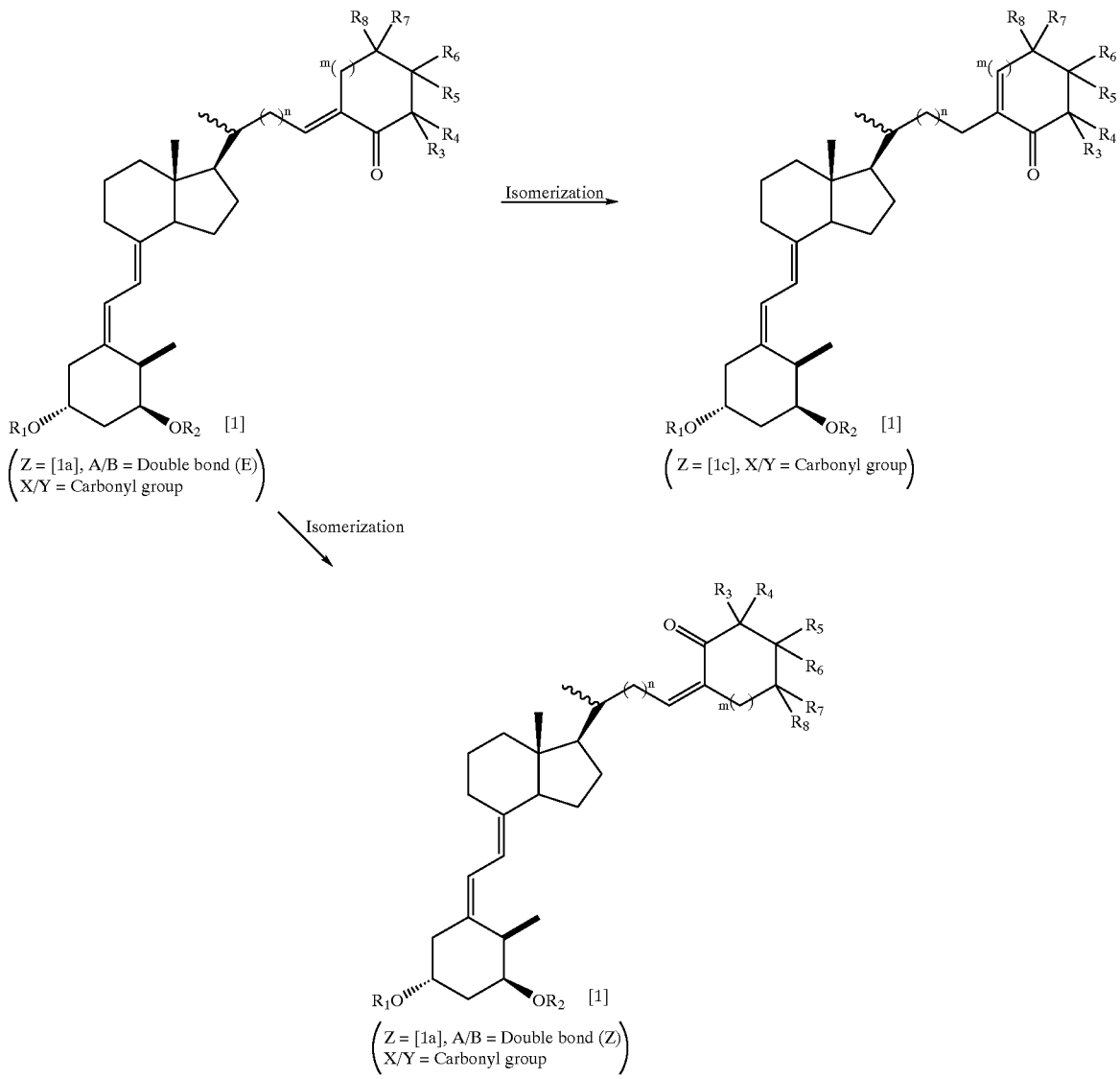

In this isomerization, a transition metal compound such as rhodium chloride or ultraviolet rays may be used.

Thus obtained compounds expressed by the above formula [1] optionally can be converted into vitamin $D_3$ derivatives expressed by the following formula [1] in which $R_1$ and $R_2$ are each hydrogen by subjecting to deprotection reaction.

The conversions of side chains of vitamin $D_3$ derivatives of the present invention will be precisely explained in examples.

The deprotection reaction may be carried out according to a known method (for example, Caverly, Tetrahedron, 20, 4609–4619 (1987)), and as the deprotecting agent, for example, tetrabutyl-ammonium fluoride, pyridinium p-toluenesulfonate, hydrogen fluoride, etc., may be used. Examples of the organic solvent to be used in the reaction include a halogen-containing solvent such as methylene chloride, chloroform or carbon tetrachloride, a hydrocarbon solvent such as hexane or toluene, an ether solvent such as tetrahydrofuran or dioxane, a water-soluble solvent such as N,N-dimethylformamide or acetonitrile, a mixed solvent of them, etc. The solvent may be selected in consideration of the solubility and the reactivity of the compound. The reaction temperature is commonly ranging from −20° C. to the boiling point of the solvent. The reaction time depends on the dehydrating agent, deprotecting agent, reaction solvent and reaction temperature used, and it is commonly preferable that the reaction is continued until the starting material disappears when determined by using an analytical means such as thin layer chromatography.

Further, in the deprotection reaction, the deprotection of a vitamin $D_3$ derivative expressed by the above formula [1] in which $R_1$ and $R_2$ are tri($C_1$–$C_7$ alkyl)silyl groups may be carried out by using a reagent consisting of a combination of an alkali metal salt of tetrafluoroboric acid and a mineral acid. As the alkali metal salt of tetrafluoroboric acid, lithium tetrafluoroborate, sodium tetrafluoroborate or potassium tetrafluoroborate may be used, and as the mineral acid, hydrochloric acid, sulfuric acid, etc., may be used. It is preferable that an alkali metal salt of tetrafluoroboric acid is used in an amount of 1–3 equivalent based on the hydroxyl group to be deprotected, and a mineral acid is used in an amount of 0.05–3 equivalent. To the reaction solvent, reaction temperature and reaction time, similar conditions to in the case of the above deprotection reaction may be applied. Especially, when acetonitrile or methylene chloride is ued as the solvent, the reaction temperature is preferably from 0° C. to room temperature, and the reaction time is preferably from 10 min to about 1 hr.

Furthermore, the deprotection reaction using the reagent consisting of a combination of an alkali metal salt of tetrafluoroboric acid and a mineral acid is applicable generally to vitamin $D_3$ derivatives whose hydroxyl groups at 1- and 3-positions are protected with tri($C_1$–$C_7$ alkyl)silyl groups.

Aldehydes expressed by the above formula [2] may be synthesized, for example, according to the following schemes.

An aldehyde whose n is 0 can be obtained from vitamin $D_2$ by a known method (the International Patent Publication WO90/0991; Caverly, Tetrahedron, 20, 4609–4619 (1987)). An aldehyde compound whose n is 1 or 2 can be obtained by the combination of known processes as shown in following Scheme 1 or Scheme 2.

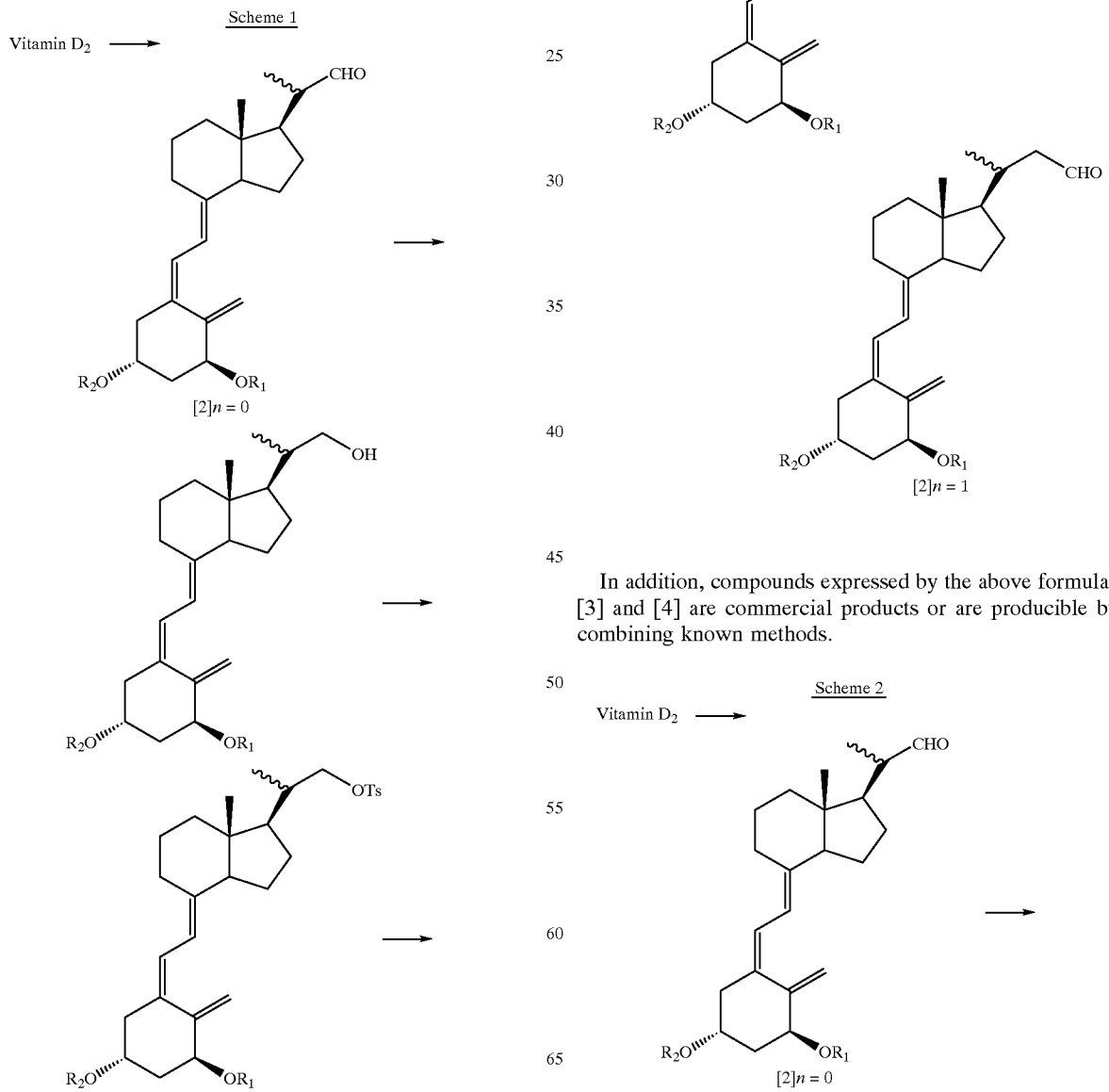

In addition, compounds expressed by the above formulae [3] and [4] are commercial products or are producible by combining known methods.

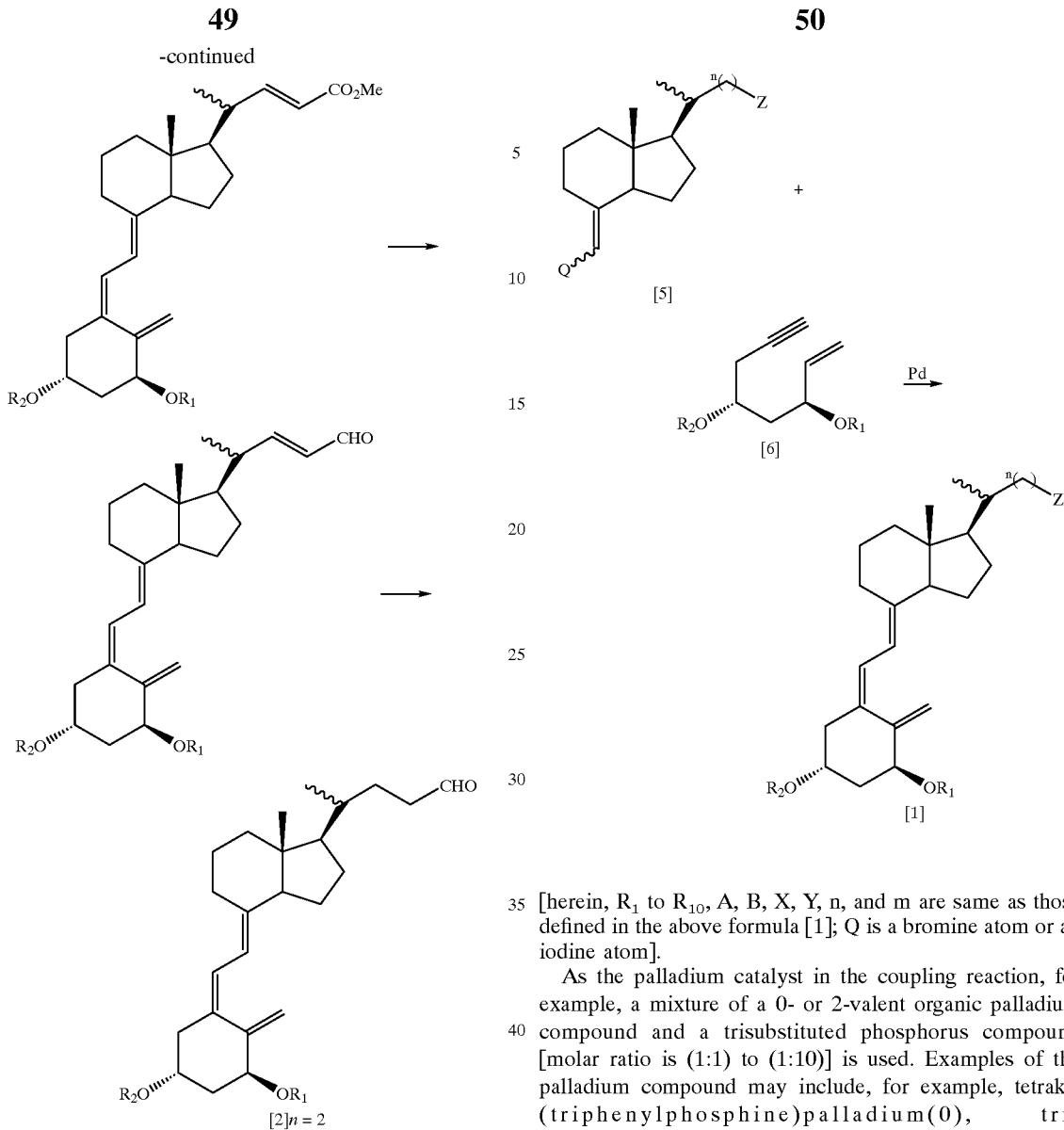

Further, a vitamin $D_3$ derivative expressed by the above formula [1] of the present invention may be produced also by the following production method. That is, a vitamin $D_3$ derivative expressed by the above formula [1] can be obtained by subjecting a compound expressed by the following formula [5] and an ene-yne compound expressed by the following formula [6] to coupling in the presence of a palladium catalyst.

Furthermore, the obtained derivative optionally can be converted into a vitamin $D_3$ derivative expressed by the above formula [1] whose $R_1$ and R2 are each a hydrogen atom by currying out deprotection reaction.

[herein, $R_1$ to $R_{10}$, A, B, X, Y, n, and m are same as those defined in the above formula [1]; Q is a bromine atom or an iodine atom].

As the palladium catalyst in the coupling reaction, for example, a mixture of a 0- or 2-valent organic palladium compound and a trisubstituted phosphorus compound [molar ratio is (1:1) to (1:10)] is used. Examples of the palladium compound may include, for example, tetrakis (triphenylphosphine)palladium(0), tris (dibenzylideneacetone)palladium(0)-chloroform adduct and palladium acetate. Further, examples of the trisubstituted phosphorus compound include triphenylphosphine and tributylphosphine. As a preferable example of the palladium catalyst, a combination of tris-(dibenzylidene-acetone) dipalladium(0)-chloroform adduct and triphenylphosphine [(1:1) to (1:10)] may be cited. Furthermore, a palladium catalyst is used in an amount in the range of 1–100 mol %, preferably 5–30 mol % based on a compound expressed by the above formula [5]. Herein, a compound expressed by the above formula [5] and an ene-yne compound expressed by the above formula [6] perform stoichiometrically equimolar reaction, but it is preferable that either of which is easier in availability is used in a little excess than the other for certainly completing the reaction.

Examples of the organic solvent to be used in the coupling reaction include a hydrocarbon solvent such as hexane or toluene, an ether solvent such as tetrahydrofuran or dioxane, a water-soluble solvent such as N,N-dimethylformamide or acetonitrile, a mixed solvent of them, etc., and they are preferably used after sufficient deaeration. As the reaction temperature, a temperature ranging from room temperature to the boiling temperature of the solvent is commonly used. The reaction time depends on the reaction solvent and the reaction temperature used in the reaction, and it is commonly preferable that the reaction is continued until either of a cycloalkanone compound expressed by the above formula [5] and an ene-yne compound expressed by the above formula [6] disappears, when determined by using an analytical means such as thin layer chromatography. Further, it is preferable that the reaction is carried out, for example, in the presence of a base such as triethylamine or diisopropylamine for trapping hydrogen chloride, besides a palladium catalyst. As for the amount of the base, one equivalent or more based on a cycloalkanone compound expressed by the above formula [5] is preferable, and optionally, the base may be used as a solvent at the same time. Further, the deprotection reaction may be performed according to the above-mentioned method.

A compound expressed by the above formula [5] to be used as a raw material in the production method of the present invention may be produced, for example, by reacting a compound expressed by the following formula [7] with a compound expressed by the following formula [3] or [4] in aldol reaction and optionally treating the reaction product for dehydration, deprotection, reduction, isomerization, etc., as shown in Scheme 3. These reactions are carried out substantially in the same manner as the above-mentioned aldol reaction that is carried out between a compound expressed by the above formula [2] and a compound expressed by the above formula [3] or [4], and dehydration, deprotection, reduction, isomerization, etc., which are optionally carried out following the aldol reaction, to produce a compound expressed by the above formula [1].

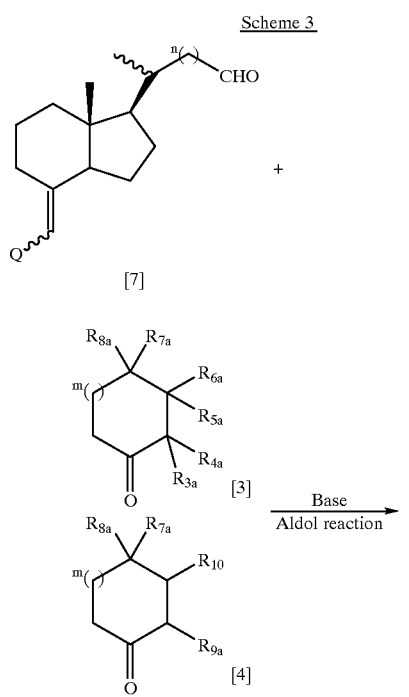

Scheme 3

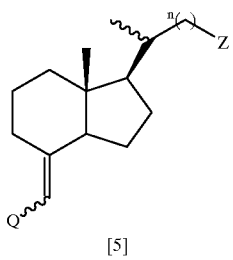

[5]

Further, compound [7] used in the above Scheme 3 may be produced by combining known methods as shown in Scheme 4 (n=0), Scheme 5 (n=1) and Scheme 6 (n=2).

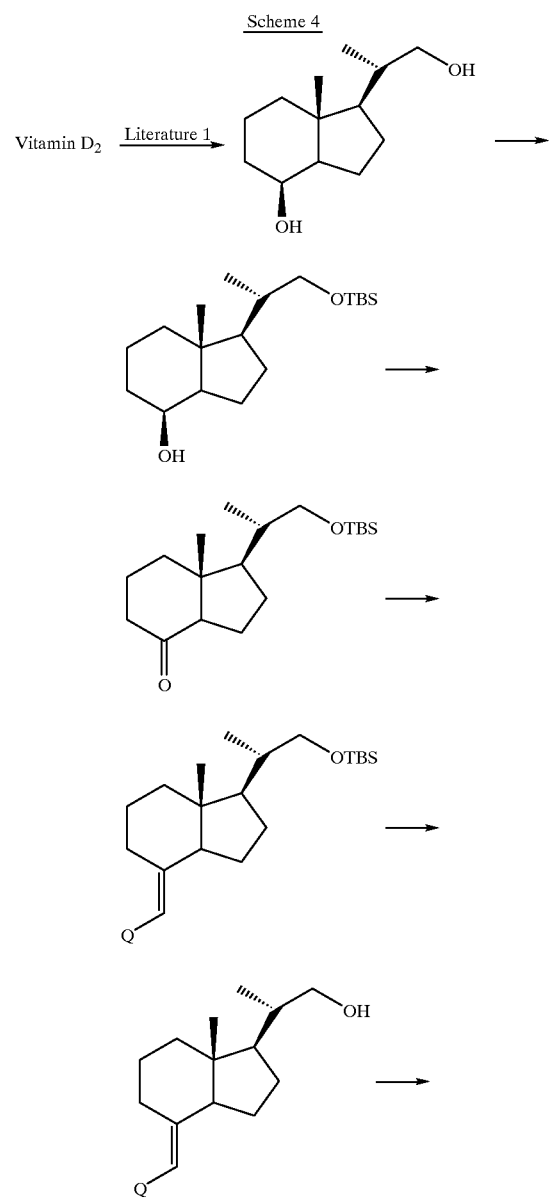

Scheme 4

53
-continued
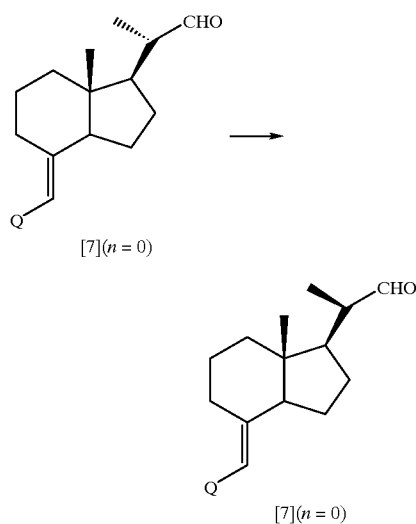
[7](n = 0)
Literature 1: J. Org. Chem., 51, 1264 (1986)
Scheme 5
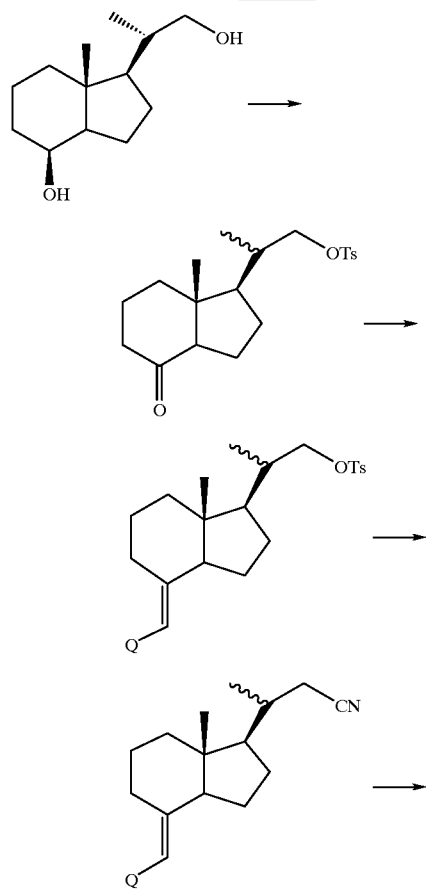
54
-continued
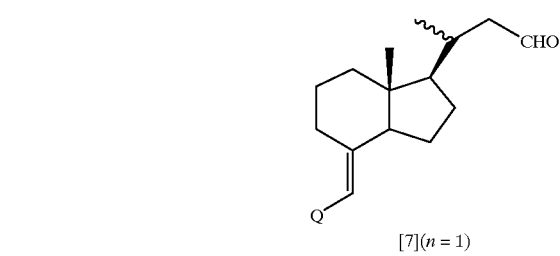
[7](n = 1)
Scheme 6
Vitamin D$_2$ →
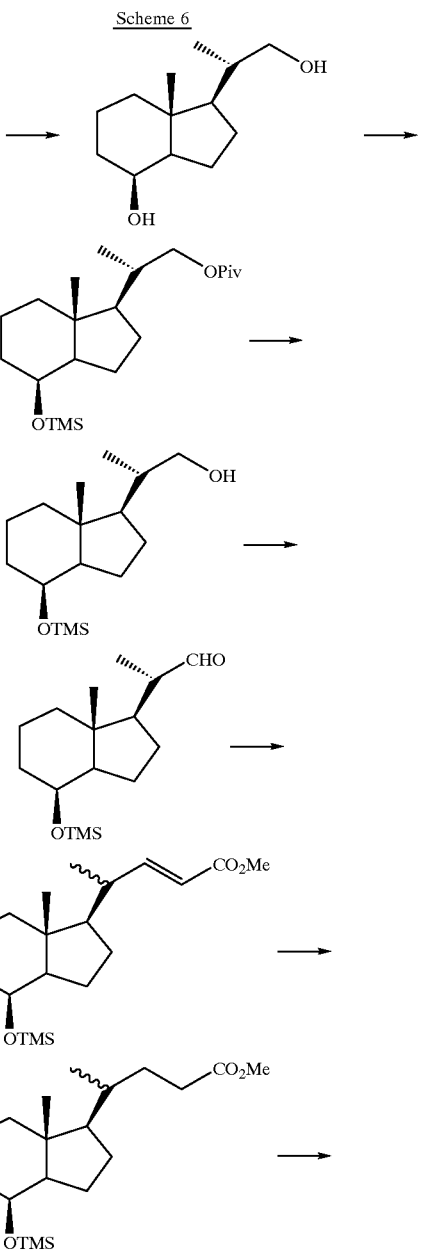

-continued

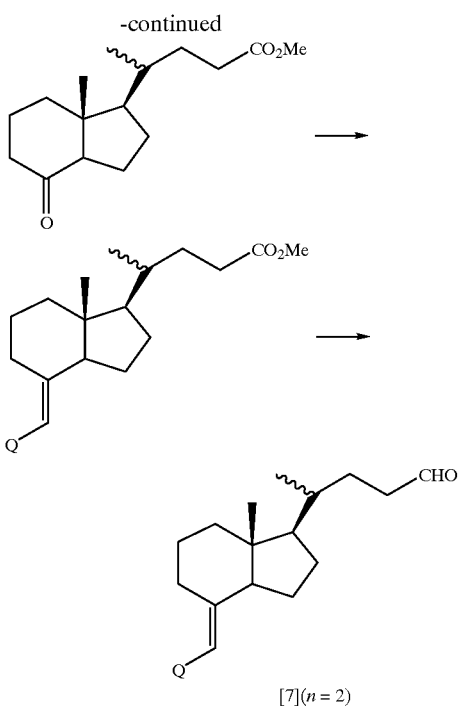

[7](n = 2)

Further, compounds expressed by the above formulae [3] and [4] are commercial products or producible by combining known methods.

Thus obtained vitamin $D_3$ derivatives is optionally converted into a pharmaceutically permissible solvate as shown above.

Furthermore, the present invention provides treating agents for inflammatory respiratory diseases containing above vitamin $D_3$ derivatives in therapeutically effective amounts and also methods for treating the diseases using the agents.

The inflammatory respiratory diseases to be objective of the treating agents or the treating methods of the present invention includes, for example, one or not less than two kinds of inflammatory respiratory diseases selected from a group consisting of acute upper airway infection, chronic sinusitis, allergic rhinitis, chronic lower respiratory infection, pulmonary emphysema, pneumonia, asthma, pulmonary tuberculosis sequela, acute respiratory distress syndrome and pulmonary fibrosis.

Especially, one or not less than two kinds of acute upper airway infections selected from a group consisting of, for example, common cold, acute pharyngitis, acute rhinitis, acute sinusitis, acute tonsillitis, acute laryngitis, acute epiglottitis and acute bronchitis, or one or not less than two kinds of chronic lower airway infections selected from a group consisting of, for example, chronic bronchitis, diffuse panbronchiolitis and bronchiectasis are preferably cited as inflammatory respiratory disease which is objective of the present invention.

Further, the present invention provides treating agents for malignant tumors containing above vitamin $D_3$ derivatives as active ingredients in therapeutically effective amounts and also provides therapeutic methods for the diseases using the agents. The treating agents may be administered for reducing the sizes or suppressing the growths of tumor cites after confirmed diagnosis of cancer, or for preventing the recurrence of the cancer after surgical operation or radiotherapy. Further, the kind of malignant tumor to be objective is not specifically restrictive, but especially, leukemia, colon cancer, prostatic carcinoma, breast cancer, lung cancer, brain tumor and melanoma may be cited as preferable objectives.

Furthermore, the present invention provides treating agents for diseases selected from a group consisting of rheumatoid arthritis, osteoporosis, diabetes mellitus, hypertension, alopecia, acne, psoriasis and dermatitis which contain vitamin $D_3$ derivatives or pharmaceutically permissible solvates thereof in therapeutically effective amounts and methods for treating a group of the diseases using the treating reagents.

Treating agents for various diseases of the present invention can be administered orally, or parenterally through intravenous, subcutaneous, intramuscular, percutaneous, intranasal or intrarectal route, or by inhalation.

Dosage forms for oral administration include tablets, pills, powders, granules, liquids, suspensions, syrups, capsules, etc.

The tablets are formulated according to a conventional process by using additives consisting of an excipient such as lactose, starch, calcium carbonate, crystalline cellulose or silicic acid; a binder such as carboxymethylcellulose, methylcellulose, calcium phosphate or polyvinylpyrrolidone; a disintegrator such as sodium alginate, sodium bicarbonate, sodium laurylsulfate or stearic acid monoglyceride; a humectant such as glycerin; an absorbent such as kaolin or colloidal silica; a lubricant such as talc or granular boric acid, etc.

The pills, powders and granules are prepared by conventional processes also using additives similar to those mentioned above.

Liquid preparations such as the liquids, suspensions and syrups can be formulated also according to conventional processes. As a carrier, for example, a glycerol ester such as tricaprylin, triacetin or an iodized poppy oil fatty acid ester; water; an alcohol such as ethanol; and an oily base such as liquid paraffin, coconut oil, soybean oil, sesame oil or corn oil is used.

The capsules are formulated by filling a powdery, granular or liquid pharmaceutical composition, etc., in gelatin capsules, etc.

Dosage forms for intravenous, subcutaneous and intramuscular administration include injections in the forms of sterilized aqueous solutions, non-aqueous solutions, etc. In an aqueous solution, for example, a physiological saline solution, etc., is used as a solvent. In a non-aqueous solution, for example, propylene glycol, polyethylene glycol, a vegetable oil such as olive oil, an organic ester which is acceptable for injection such as ethyl oleate or an iodized poppy oil fatty acid ester, etc., is used as a solvent. To the pharmaceutical preparations for injection are optionally added an isotonizing agent, a preservative, a humectant agent, an emulsifier, a dispersant, a stabilizer, etc., and the preparation may be sterilized by an adequate treatment such as filtration through a bacterium-retaining filter, blending of a germicide or irradiation. Also, the preparation may be prepared as aseptic solid preparation, which is used by dissolving in sterilized water or a sterilized solvent for injection just prior to use.

Further, a compound of the present invention may be used in the form of a clathrate compound prepared using α, β or γ-cyclodextrin, a methylated cyclodextrin, etc. The compound may be used also as an injection of lipoid form.

Dosage forms for percutaneous administration include ointments, creams, lotions, solutions, etc.

The base of an ointment include, for example, a fatty acid such as castor oil, olive oil, sesame oil or safflower oil;

lanolin; white, yellow or hydrophilic vaseline; wax; a higher alcohol such as oleyl alcohol, isostearyl alcohol, octyldodecanol or hexyldecanol; a glycol such as glycerin, diglycerin, ethylene glycol, propylene glycol, sorbitol or 1,3-butanediol; etc. Further, as a solubilizing agent for a compound of the present invention, ethanol, dimethyl sulfoxide, polyethylene glycol, etc., may be compounded. Optionally, a preservative such as a paraoxybenzoic acid ester, sodium benzoic acid, salicylic acid, sorbic acid or boric acid; an antioxidant such as butylhydroxyanisole or dibutylhydroxytoluene; etc., may be added.

Further, for stimulating percutaneous absorption in an ointment, an absorption promoter such as diisopropyl adipate, diethyl sebacate, ethyl caproate or ethyl laurate may be compounded. Also, for stabilization, a compound of the present invention may be used in the form of a clathrate compound prepared using $\alpha$, $\beta$ or $\gamma$-cyclodextrin, a methylated cyclodextrin, etc. An ointment can be prepared by a conventional process.

For the creams, dosage forms of oil-in-water type are preferable for stabilizing compounds of the present invention. Further, the above-mentioned fatty oil, higher alcohol, glycol, etc., can be used as the base of a cream, and diethylene glycol, propylene glycol, sorbitan mono fatty acid ester, polysorbate 80, sodium laurylsulfate, etc., is used as the emulsifier of a cream. Further, the above-mentioned preservative, antioxidant, etc., may be added. Furthermore, as in the case of ointment, a compound of the present invention can be used in the form of a clathrate compound prepared using a cyclodextrin or a methylcyclodextrin. A cream can be prepared according to a conventional process.

Examples of the lotions include a suspension-type lotion, an emulsion-type lotion and a solution-type lotion. The suspension-type lotion is prepared by using a suspending agent such as sodium alginate, traganth or sodium carboxymethylcellulose, and optionally by adding an antioxidant, a preservative, etc.

The emulsion-type lotion is prepared according to a conventional process using an emulsifier such as sorbitan mono fatty acid ester, polysorbate 80 or sodium laurylsulfate. A compound of the present invention is dissolved in an alcohol such as ethanol, and optionally an antioxidant, a preservative, etc., are added.

Besides the above-mentioned dosage forms, a pasta, a poultice, an aerosol, etc., may be cited. The pharmaceutical preparations having these dosage forms can be prepared according to conventional processes.

Pharmaceutical preparations for intranasal administration are supplied in the form of a liquid or powdery composition. As the base of the liquid preparation, water, saline, a phosphate buffer solution, an acetate buffer solution, etc., is used, and the liquid preparation may contain further a surfactant, an antioxidant, a stabilizer, a preservative and/or a thickener. As the base for the powdery preparation, a water-absorbent base is preferable. The examples of the water-absorbent base include polyacrylate salts such as sodium polyacrylate, potassium polyacrylate and ammonium polyacrylate; cellulose lower-alkyl ethers such as methylcellulose, hydroxyethylcellulose, hydroxypropylcellulose and sodium carboxymethylcellulose; polyethylene glycol; polyvinyl pyrrolidone; amylose; pullulan, etc., which are soluble in water, and cellulose compounds such as crystalline cellulose, $\alpha$-cellulose and cross-linked sodium carboxymethylcellulose; starch compounds such as hydroxypropyl starch, carboxymethyl starch, cross-linked starches, amylose, amylopectin and pectin; proteins such as gelatin, casein and sodium caseinate; gums such as gum arabic, tragacanth gum and glucomannan gum; polyvinylpolypyrrolidone, cross-linked polyacrylic acid and salts thereof, cross-linked polyvinyl alcohols, etc., which are scarcely soluble in water. These compounds may be used alone or in mixtures of two or more thereof. The powdery preparation may be further compounded with an antioxidant, a coloring agent, a preservative, a disinfectant, an antiseptic, etc. These liquid and powdery preparations can be applied, for example, each by using a spraying device, etc.

For intrarectal administration, ordinary suppositories such as gelatin soft capsule are used.

Further, for inhalation, a powdery or liquid composition prepared using an active ingredient of a vitamin $D_3$ derivative of the present invention alone or in combination with an adequate biocompatible vehicle can be administered to disease sites by using an applicator such as a spraying device, a nebulizer or an atomizer. Alternatively, an active ingredient may be administered to disease sites in a dosage form prepared by suspending in a spraying agent for aerosol such as flon.

A pharmaceutically effective dose of an active ingredient of the present invention depends on administration route, age and sex of the patient, objective disease, and the conditions of the disease, but it is ordinarily about 0.001–100 $\mu$g per day, preferably about 0.1–10 $\mu$g per day, and administration frequency is ordinarily 1–3 time per day. The pharmaceutical preparation is preferably prepared so as to meet these conditions.

Further, treating agents of the present invention for various kinds of diseases can be administered in combination with conventional medicines.

Effectiveness for inflammatory respiratory diseases of vitamin $D_3$ derivatives expressed by the above formula [1] of the present invention has been demonstrated by experiments using LPS-induced airway inflammatory hamsters, which are widely used as an inflammatory pulmonary disease model, as shown concretely in the following examples. That is, it has been found that compounds of the present invention significantly suppress LPS-induced airway inflammatory by intra-respiratory tract administration or oral administration.

Further, effectiveness for malignant tumors of vitamin $D_3$ derivatives expressed by the above formula [1] of the present invention has been demonstrated by experiments using human leukemia cells (HL-60), human colon cancer cells (HT-29) or cancer cell-transplanted mice as shown concretely in the following examples. That is, it has been found that vitamin $D_3$ derivatives of the present invention exhibit the differentiation inducing effect on human leukemia cells (HL-60) and the growth suppressing effect on human colon cancer cells (HT-29), and they suppress the growth of the cancer cells of cancer cell-transplanted mice by oral administration.

On the other hand, it has been clarified that the blood calcium level-elevation effects of compounds of the present invention is extremely reduced compared with that of 1 $\alpha$,25-dihydroxyvitamin $D_3$ although the generally most worried side effect of active vitamin $D_3$ compounds is the elevation of calcium level in blood. For example, the blood calcium level-elevation effects of vitamin $D_3$ derivatives of the present invention in oral administration to rats, which are compared with that of 1 $\alpha$,25-dihydroxyvitamin $D_3$, are as shown below:

Compound No. 1101, 1/>500,
Compound No. 1105b, 1/17
Compound No. 1110b, 1/111
Compound No. 1112b, 1/27

Compound No. 1126b, 1/47
Compound No. 1126d, 1/115
Compound No. 1127a, 1/41
Compound No. 1127b, 1/79
Compound No. 1128a, 1/16
Compound No. 1128b, 1/11
Compound No. 1129b, 1/55
Compound No. 1130b, 1/11
Compound No. 1131a, 1/10
Compound No. 1401a, 1/158.

From the above results, it is confirmed that in vitamin $D_3$ derivatives expressed by the above formula [1], the separation of the development concentrations for anti-inflammatory effect and anti-malignant tumor effect from that for blood calcium level elevation effect has been achieved, and side effect will not be generated.

Thus, treating agents containing vitamin $D_3$ derivatives expressed by the above formula [1] as active ingredients can be considered to be effective for inflammatory respiratory diseases or malignant tumors.

By the way, it has been reported that an active vitamin $D_3$ has various effects on cell metabolism. Examples of such reports include the stimulation of maturation and differentiation of cell (Tanaka, et al., Biochem. J., 204, 713–719 (1982); Amento, et al., J. Clin. Invest., 73, 731–739 (1984); Colston, et al., Endocrinology, 108, 1083–1086 (1981); Abeetl, et al., Proc. Natl. Acad. Sci., 78, 4990–4994 (1981)) and immunosuppression effect such as interleukin-2 production inhibition (Rigby, Immunology Today, 9, 54–58 (1988)). In addition, also immunology synergistic effect has been detected, and the stimulation of he production of bactericidal oxygen metabolites and the stimulation of leukocyte chemotactic response has been discovered.

It has been recognized that also vitamin $D_3$ derivatives expressed by the above formula [1] have the cell differentiation-inducing effect as mentioned above. This fact demonstrates that vitamin $D_3$ derivatives expressed by the above formula [1] have possibilities of therapies in various fields including, for example, psoriasis, rheumatoid arthritis, inflammatory diseases such as dermatitis and autoimmune diseases, and supplementary agents in chemotherapy of infectious diseases (especially, bacterial, viral or fungus) and other therapies associated with mononuclear phagocyte.

Further, it has been reported that an active vitamin $D_3$ is effective in the treatment of hypertension (Lind, et al., Acta Med. Scand., 222, 423–427 (1987)), the treatment of diabetes mellitus (Inomata, et al., Bone Mineral, 1, 187–192 (1986)), the stimulation of hair growth (Lancet, March 4, 478 (1989)) and the treatment of acne (Malloy, et al., Tricontinental Meeting for Investigative Dermatology, Washington, 1989), and it is expected that vitamin $D_3$ derivatives of the present invention are also effective on these treatments.

Some of vitamin $D_3$ derivatives expressed by the above formula [1] are very high binding affinties bonding to 1 α,25-dihydroxyvitamin $D_3$ receptor, that is, they have binding affinties ranging from same degree to 1/50 of 1 α,25-dihydroxyvitamin $D_3$, and high vitamin $D_3$-like effects can be expected in them.

Also, in assay systems using other cell lines, for example, a compound No. 1127a accelerated collagen synthesis and non-collagen protein synthesis in mouse osteoblastic cell line (MCJT) in a dose-related manner. The collagen synthesis acceleration effect of the compound No. 1127a was stronger than that of 1 α,25-dihydroxyvitamin $D_3$. Further, in the compound, calcification acceleration effect has also been detected in human osteoblastic cell line (SAM-1).

Further, when the formation acceleration effect of osteoclast was assayed, compounds No. 1128a and 1130a exhibited significant osteoclast formation acceleration effects. This suggests that these compounds activate bone metabolism turnover accompanied by the osteoclast formation acceleration, and thus they have possibility to become treating agents for osteoporosis.

EXAMPLES

The present invention will be explained further in detail hereafter with examples, while the present invention is not restricted by the examples. The compound number in each example corresponds to the compound number shown in the above Table 1—1 to Table 1-14 or Table 2-1 to Table 2-3. A compound number having an alphabet shows a stereoisomer (including geometrical isomer) of the compound.

Reference Example 1

Production of compound 7 (n=0)

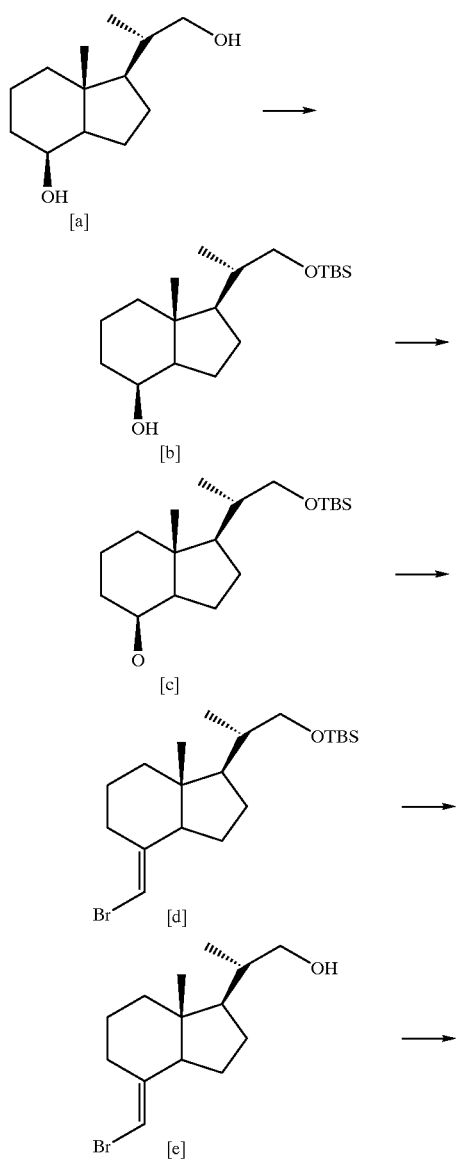

-continued

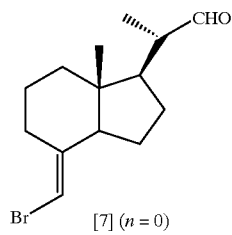

In 50 ml of methylene chloride was dissolved [a] (2.15 g) at room temperature, and the resultant solution was cooled with ice. To the cooled solution were serially added diisopropylethylamine (1.58 g) and t-butyldimethylsilyl chloride (1.54 g), and the mixture was stirred overnight after it was warmed up to room temperature. The reaction mixture was poured into ice-cooled water and extracted with methylene chloride. The organic layer was washed with brine, dried over sodium sulfate anhydride and evaporated to obtain crude [b].

The obtained [b] was dissolved in 20 ml of methylene chloride and cooled with ice. A mixture of pyridinium chlorochromate (PCC) (3.3 g) and celite (about 3 g) was added to the solution, and the mixture was warmed up to room temperature. After stirring for 2.5 hr, the reaction mixture was filtered, and the filtrate was concentrated and purified by silica gel column chromatography (hexane:ethyl acetate=20:1) to obtain [c] (3.2 g, 98% yield).

$^1$H NMR (CDCl$_3$) δ: 3.33, (dd, J=2.6, 9.6 Hz, 1 H), 2.57 (dd, J=2.6, 9.6 Hz, 1 H), 2.27 (dd, J=2.6, 6.3 Hz, 1 H), 1.23–2.29 (m, 1 H), 1.03 (d, J=6.3 Hz, 3 H), 0.89 (s, 9 H), 0.65 (s, 3 H), 0.03 (s, 6 H).

A container having 0.45 g of molecular sieve 4A in it was heated under reduced pressure with a heat gun to be dried. Bromomethyltriphenylphosphine bromide (13.26 g) and 70 ml of tetrahydrofuran were added to this, and the mixture was cooled to –70°C. To this mixture was added dropwise 26 ml of 1 M-tetrahydrofuran solution of sodium bistrimethylsilylamide while the temperature was slowly elevated up to –40° C. The mixture was cooled again down to –78° C. and added dropwise to a solution of [c] (1.23 g) in tetrahydrofuran (15 ml), which had been cooled to –15° C., through a cannula. After the completion of the addition, the mixture was continuously stirred as it was for 30 min. The reaction mixture was poured into hexane having suspended silica gel, the resultant mixture was filtered through celite, and the silica gel was washed with ethyl acetate. The filtrate was evaporated, and the residue was purified with silica gel column chromatography (hexane:ethyl acetate=100:1 to 10:1) to obtain [d] in a form of a mixture with triphenylphosphine.

The obtained [d] was dissolved in 5 ml of methylene chloride and 5 ml of acetonitrile, and the solution was cooled to 0° C. Lithium tetrafluoroborate (739 mg) was added to this, and then a solution prepared by diluting concentrated sulfuric acid with acetonitrile was added dropwise. When [d] had disappeared on thin layer chromatography (TLC), water and a saturated sodium bicarbonate solution were added, and the mixture was extracted with methylene chloride. The organic layer was washed with brine, dried and concentrated. The residue was purified with silica gel column chromatography (hexane: ethyl acetate=5:1 to 4:1) to obtain [e] (660 mg, 59% yield).

$^1$H NMR (CDCl$_3$) δ: 5.66 (d, J=1.7 Hz, 1 H), 3.65 (dd, J=3.3, 10.6 Hz, 1 H), 3.40 (dd, J=6.6, 10.6 Hz, 1 H), 2.85–2.90 (m, 1 H), 1.23–2.03 (m, 12 H), 1.06 (d, J=6.6 Hz, 3 H), 0.59 (s, 3 H).

The obtained [e] (660 mg) was dissolved in 18 ml of acetone. To the solution were added N-methylmorpholine-N-oxide (546 mg) and tristriphenylphosphine ruthenium (II) chloride (67 mg), and the mixture was stirred for 1 hr at room temperature. The reaction mixture was poured into ether having suspended silica gel, and the mixture was filtered through celite. The filtrate was concentrated under reduced pressure, and the residue was purified by silica gel column chromatography (hexane: ethyl acetate=30:1 to 1:1) to obtain the objective product (432 mg, 67% yield).

$^1$H NMR (CDCl$_3$) δ: 9.59 (d, J=3.3 Hz, 1 H), 5.68 (s, 1 H), 2.88–2.93 (in, 1 H), 2.32–2.42 (m, 1 H), 2.01–2.10 (in, 2 H), 1.33–1.98 (in, 9 H), 1.15 (d, J=6.9 Hz, 3 H) 0.61 (s, 3 H).

Reference Example 2

Production of Compound [7] (n=1)

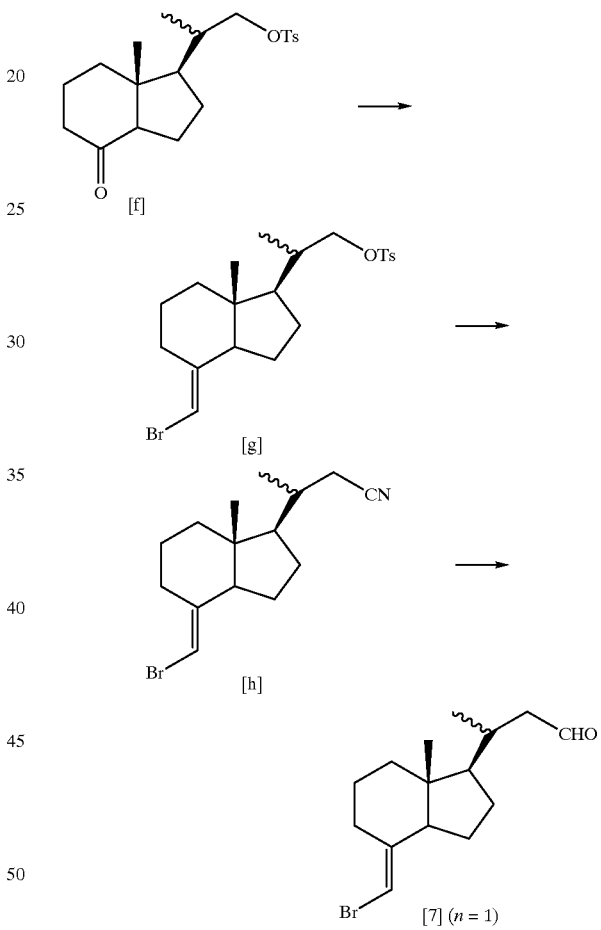

Bromomethylenetriphenylphosphonium bromide (2.39 g) was placed in a 100-ml egg plant-type flask, 40 ml of dry THF was added, and these were stirred and cooled to –70° C. To the solution was added dropwise 5.28 ml of 1M solution of sodium hexamethyldisilazide in THF, and the mixture was stirred for 1 hr at the same temperature. Subsequently, a solution prepared by dissolving [f] (300 mg) in 10 ml of dry THF was added dropwise, and then the mixture was stirred for 1 hr after the cooling bath was removed. Then, the reaction mixture was filtered after hexane was added to remove insoluble matters, and the filtrate was evaporated under reduced pressure. The residue was purified by silica gel column chromatography (hexane: ethyl acetate=14:1 to 9:1) to obtain [g] (178 mg, 48% yield).

$^1$H NMR (CDCl$_3$) δ: 7.78 (d, J=8 Hz, 2 H), 7.35 (d, J=8 Hz, 2 H), 5.64 (s, 1 H), 3.96 (dd, J=3, 9 Hz, 1 H), 3.82 (dd, J=6, 9 Hz, 1 H), 2.45 (s,3 H), 0.99 (d, J=7 Hz, 3 H), 0.53 (s, 3 H).

In a 50-ml egg plant-type flask, [g] (178 mg) was placed, and 6 ml of DMF was added to dissolve [g]. KCN (215 mg) was put into the solution, and the mixture was stirred for 24 hr at 50° C. After 50 ml of water was added, the reaction mixture was extracted with ether. The organic layer was washed with water, and then with brine, dried over magnesium sulfate anhydride and evaporated under reduced pressure to obtain a crude product (110 mg). This was purified by silica gel column chromatography (hexane: ethyl acetate'14:1) to obtain [h] (84 mg, 69% yield).

$^1$H NMR (CDCl$_3$) δ: 5.67 (s, 1 H), 2.86–2.91 (m, 1 H), 2.21–2.35 (m, 2 H), 1.18 (d, J=6 Hz, 3 H), 0.59 (s, 3 H).

In a 25-ml egg plan-type flask, [h] (84 mg) was placed, and 5 ml of dry dichloromethane was added to dissolve [h]. After the mixture was cooled to −70° C., 660 µl of 1.5 M solution of diisobutyl-aluminum hydride in toluene was added dropwise. The mixture was stirred for 1 hr at the same temperature, then 0.5 ml of a saturated sodium sulfate aqueous solution, 0.3 ml of methanol, 0.5 ml of 2N hydrochloric acid and 15 ml of ethyl acetate were added, and the resultant mixture was stirred for 30 min. The reaction mixture was filtered through celite, the filtrate was washed with a saturated ammonium chloride aqueous solution and subsequently with brine, dried over magnesium sulfate anhydride and evaporated under reduced pressure to obtain the object product (85 mg).

Reference Example 3

Production of Compound [7] (n=2)

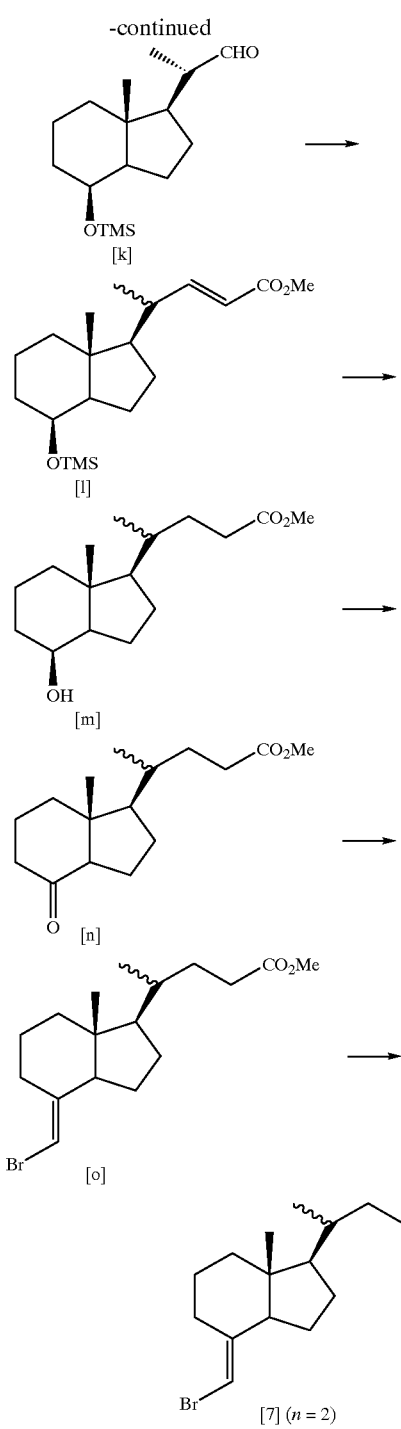

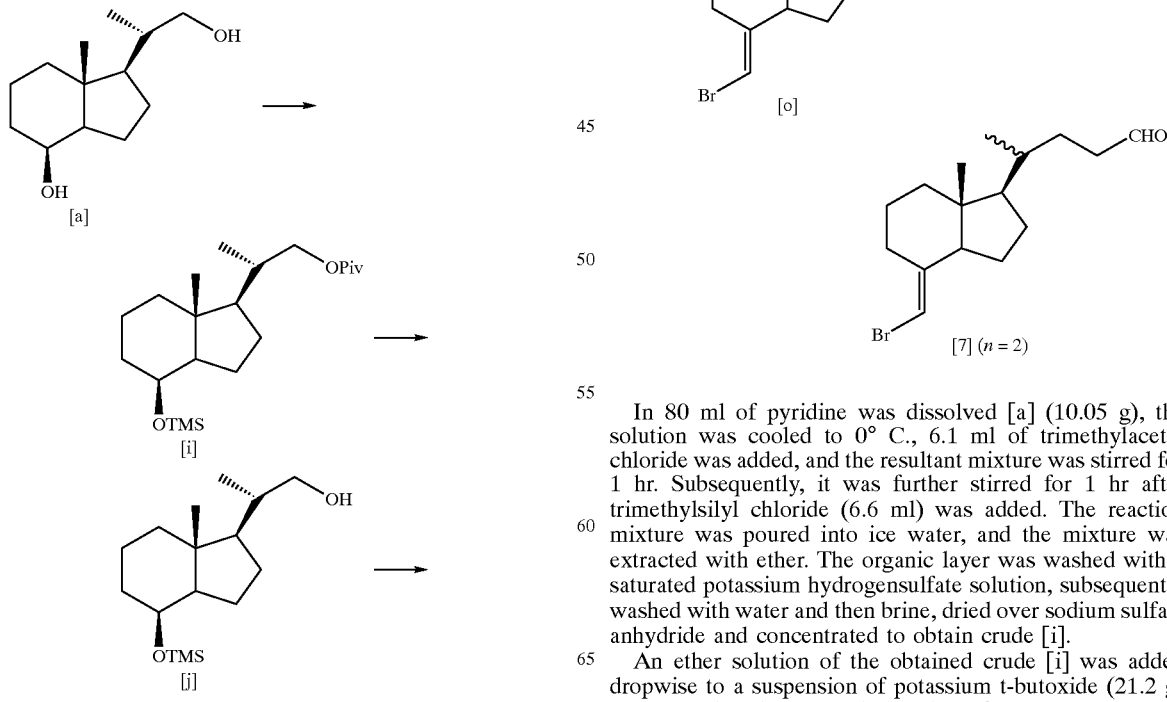

In 80 ml of pyridine was dissolved [a] (10.05 g), the solution was cooled to 0° C., 6.1 ml of trimethylacetyl chloride was added, and the resultant mixture was stirred for 1 hr. Subsequently, it was further stirred for 1 hr after trimethylsilyl chloride (6.6 ml) was added. The reaction mixture was poured into ice water, and the mixture was extracted with ether. The organic layer was washed with a saturated potassium hydrogensulfate solution, subsequently washed with water and then brine, dried over sodium sulfate anhydride and concentrated to obtain crude [i].

An ether solution of the obtained crude [i] was added dropwise to a suspension of potassium t-butoxide (21.2 g) and water (2 ml) in ether (270 ml) at 0° C. The temperature of the mixture was elevated to room temperature as it was, and the mixture was stirred overnight. The reaction mixture was poured into ice water and extracted with ether, and the organic layer was washed with brine, dried over magnesium sulfate anhydride and concentrated. The residue was purified by silica gel column chromatography (hexane: ethyl acetate=9:1) to obtain [b] (12.86 g, 96% yield).

$^1$H NMR (CDCl$_3$) δ: 4.00 (br, 1 H), 3.63 (dd, J=3.3, 10.6 Hz, 1 H), 3.36 (dd, J=6.9, 10.6 Hz, 1 H), 1.10–1.96 (m, 13 H), 1.02 (d, J=6.6 Hz, 3 H), 0.90 (s, 3 H), 0.05 (s, 9 H).

The obtained [j] was subjected to the same treatment as that for converting [e] into [7] (n=0) in Reference Example 1, and thus [k] was obtained.

$^1$H NMR (CDCl$_3$) δ: 9.58 (d, J=3.2 Hz, 1 H), 4.02 (br., 1 H), 2.31–2.41 (m, 1 H), 1.24–1.83 (m, 12 H), 1.09 (d, J=6.5 Hz, 3 H), 0.93 (s, 3 H), 0.06 (s, 9 H).

To 70 ml of a toluene solution of the obtained [k] (3.46 g) was added methyl (triphenylphosphoranylidene)acetate (12.24 g), and the mixture was heated at reflux overnight. After insoluble matters were filtered off, the filtrate was evaporated, and the residue was purified by silica gel column chromatography (hexane: ethyl acetate=30:1) to obtain [l] (3.88 g, 94% yield).

$^1$H NMR (CDCl$_3$) δ: 6.84 (dd, J=8.9, 15.5 Hz, 1 H), 5.74 (d, J=15.5 Hz, 1 H), 3.99 (br., 1 H), 3.72 (s, 3 H), 2.21–2.30 (m, 1 H), 1.11–1.96 (m, 12H), 1.06 (d, J=6.3 Hz, 3 H), 0.92 (s, 3 H), 0.05 (s, 9 H).

The obtained [l] (2.08 g) was dissolved in 10 ml of methanol and 5 ml of ethyl acetate. To the resultant solution were added one drop of concentrated hydrochloric acid and then, about 100 mg of palladium-carbon, and the reaction system was substituted with hydrogen. The mixture was stirred overnight at room temperature as it was, the reaction mixture was filtered, and the filtrate was concentrated. The residue was purified by silica gel column chromatography (hexane: ethyl acetate=4:1) to obtain [m] (1.58 g, 96% yield).

$^1$H NMR (CDCl$_3$) δ: 4.08 (d, J=3.0 Hz, 1 H), 3.66 (s, 3 H), 1.05–2.42 (m, 17 H), 0.93 (s, 3 H), 0.90 (d, J=6.6 Hz, 3 H).

Pyridinium dichromate (PDC) (3.64 g) was dissolved in 20 ml of dimethylformamide, and the solution was cooled to 0° C. To the resultant solution was added dropwise a solution of the above-obtained [m] (1.29 g) in 5 ml of dimethylformamide, and the mixture was stirred for 2 hr as it was. The reaction mixture was poured to a suspension of silica gel in a mixed solvent of hexane: ethyl acetate=2:1, the resultant mixture was filtered through celite, and the filtrate was concentrated. The residue was purified by silica gel column chromatography (hexane: ethyl acetate=8:1 to 4:1) to obtain [n] (1.24 g, 97% yield).

$^1$H NMR (CDCl$_3$) δ: 3.67 (s, 3 H), 1.26–2.48 (m, 17 H), 0.96 (d, J=4.6 Hz, 3 H), 0.64 (s, 3 H).

The obtained [n] was subjected to the same treatment as that for converting [c] into [d] in Reference Example 1, and thus [o] was obtained in 50% yield.

$^1$H NMR (CDCl$_3$) δ: 5.64 (d, J=1.7 Hz, 1 H), 3.66 (s, 3 H), 2.84–2.90 m, 1 H), 2.23–2.42 (m, 2 H), 1.21–2.04 (m, 14 H), 0.93 (d, J=6.3 Hz, 3 H), 0.56 (s, 3 H).

To a solution of the obtained [o] (292 mg) in 5 ml of methylene chloride was added at −78° C. 1 ml of 0.93 M hexane solution of diisobutylammonium hydride. After the mixture was stirred for 30 min, 2 ml of methanol was added and the resultant mixture was well stirred. To the reaction mixture was added a saturated ammonium chloride aqueous solution, the resultant mixture was warmed up to room temperature, and the reaction mixture was extracted with ethyl acetate. The organic layer was sequentially washed with a saturated sodium bicarbonate aqueous solution, water and brine, dried over sodium sulfate anhydride and concentrated. The residue was purified by silica gel column chromatography (hexane: ethyl acetate=25:1) to obtain [7] (n=2) (243 mg, 91% yield).

$^1$H NMR (CDCl$_3$) δ: 9.78 (t, J=1.8 Hz, 1 H), 5.65 (d, J=1.7 Hz, 1 H), 2.85–2.90 (m, 1 H), 2.36–2.54 (m, 1 H), 1.26–2.05 (m, 16 H), 0.94 (d, J=6.3 Hz, 3 H), 0.57 (s, 3 H).

Example 1
Production of Compound No. 1144

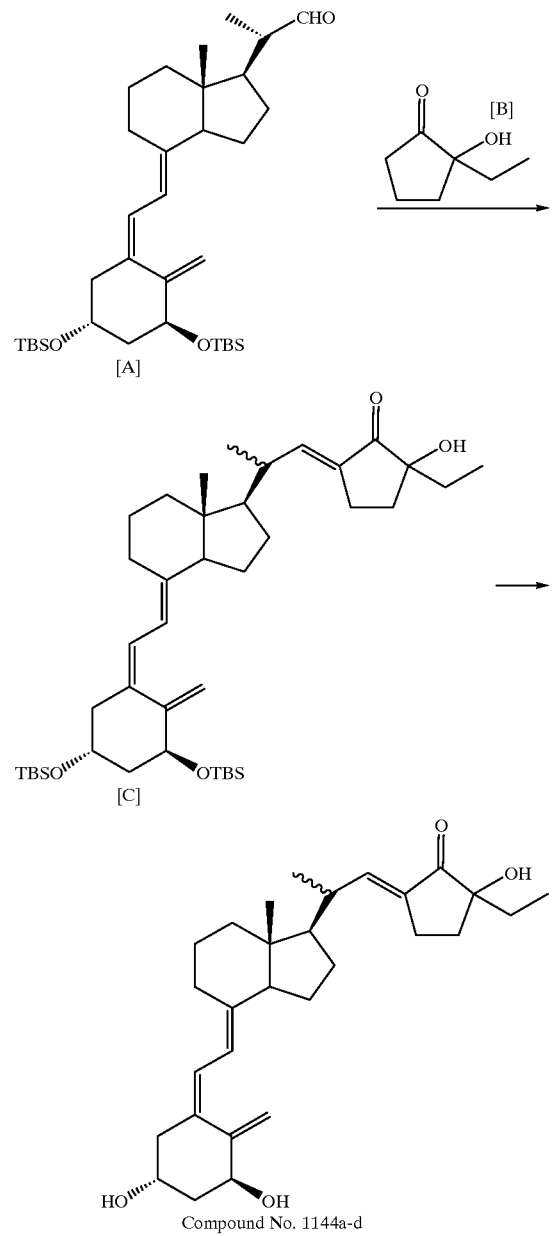

Compound No. 1144a-d

The aldehyde [A] (232 mg), which had been prepared by the above-mentioned method from vitamin D$_2$, and ketone [B] (52 mg) were dissolved in 3 ml of ethanol, the resultant solution was stirred overnight at room temperature after the addition of KOH (54 mg). The reaction mixture was extracted twice with ethyl acetate after ethyl acetate and 1N hydrochloric acid were added. Both the organic layers were combined, and they were washed with a saturated sodium bicarbonate aqueous solution, dried and concentrated. The residue was purified with silica gel column chromatography (hexane: ethyl acetate=100:3 to 100:7) to separate two spots each containing [C]. Yield: 51 mg and 55 mg (106 mg in total, 38%). Colorless oils. The product (51 mg) corresponding to the upper spot on the TLC out of the obtained [C] was dissolved in a mixed solvent of 0.5 ml of methylene chloride and 2.5 ml of acetonitrile, and the resultant solution was cooled with ice. To the solution was added lithium tetrafluoroborate (21 mg), and further was added dropwise 67.2 ml of 1N sulfuric acid solution in acetonitrile, and the mixture was stirred for 1 hr as it was. The reaction mixture was extracted twice with ethyl acetate after the addition of a saturated sodium bicarbonate aqueous solution. Both the organic layers were combined, and they were washed with brine, dried and concentrated. The residue was purified by HPLC (column: ODS, solvent: acetonitrile/water) to obtain the objective products, which were a compound having higher polarity (Compound No. 1144a) and that having a lower polarity (Compound No. 1144b), respectively. These are optical isomers originated from the carbon atom at the 20-position and the asymmetric carbon of the added ketone [B].

Further, the product (55 mg) corresponding to the lower spot on the TLC out of the obtained [C] was subjected to the deprotection reaction and purification process similar to those mentioned above, and the objective products consisting of a compound having a higher polarity (Compound No. 1144c) and that having a lower polarity (Compound No. 1144d) were obtained. These are optical isomers originated from the carbon atom at the 20-position and the asymmetric carbon of the added ketone [B].

[Compound No. 1144a]

$^1$H NMR (CDCl$_3$) δ: 6.62 (dt, J=2.5, 10.7 Hz, 1 H), 6.35 (d, J=11.2 Hz, 1 H), 6.00 (d, J=11.1 Hz, 1 H), 5.33 (s, 1 H), 4.43 (br., 1 H), 4.99 (s, 1 H), 4.22 (br., 1 H), 2.78–2.82 (m, 1 H), 2.56–2.65 (m, 2 H), 2.10–2.45 (m, 4 H), 1.85–2.06 (m, 4 H), 1.48–1.65 (m, 10 H), 1.15–1.46 (m, 5 H), 0.97 (d, J=6.8 Hz, 3 H), 0.92 (t, J=7.3 Hz, 3 H), 0.43 (s, 3 H).

MS m/e=477.3 [M+Na]$^+$.

[Compound No. 1144b]

$^1$H NMR (CDCl$_3$) δ: 6.53 (dt, J=2.5,10.7 Hz, 1 H), 6.37 (d, J=11.1 Hz, 1 H), 6.01 (d, J=11.4 Hz, 1 H), 5.32 (s, 1 H), 4.98 (s, 1 H), 4.43 (br., 1 H), 4.24 (br., 1 H), 2.81–2.86 (m, 1 H), 2.58–2.68 (m, 2 H), 2.28–2.43 (m, 3 H), 2.07–2.18 (m, 1 H), 1.64–2.05 (m, 8 H), 1.37–1.59 (m, 10 H), 1.11–1.19 (m, 1 H), 1.06 (d, J=6.6 Hz, 3 H), 0.93 (t, J=7.4 Hz, 3 H), 0.57 (s, 3 H).

MS m/e=477.3 [M+Na]$^+$.

[Compound No. 1144c]

$^1$H NMR (CDCl$_3$) δ: 6.63 (d, J=10.4 Hz, 1 H), 6.36 (d, J=11.2 Hz, 1 H), 6.00 (d, J=11.2 Hz, 1 H), 5.32 (s, 1 H), 4.99 (s, 1 H), 4.43 (br., 1 H), 4.22 (br., 1 H), 2.79–2.84 (m, 1 H), 2.57–2.66 (m, 2 H), 2.10–2.43 (m, 4 H), 1.79–2.07 (m, 4 H), 1.16–1.70 (m, 15 H), 0.97 (d, J=6.8 Hz, 3 H), 0.94 (t, J=7.3 Hz, 3 H), 0.41 (s, 3 H).

MS m/e=477.3 [M+Na]$^+$.

[Compound No. 1144d]

$^1$H NMR (CDCl$_3$) δ: 6.54 (dt, J=2.5, 10.6 Hz, 1 H), 6.37 (d, J=11.2 Hz, 1 H), 6.01 (d, J=11.2 Hz, 1 H), 5.32 (s, 1 H), 4.98 (s, 1 H), 4.43 (br., 1 H), 4.23 (br., 1 H), 2.81–2.86 (m, 1 H), 2.57–2.67 (m, 2 H), 2.28–2.44 (m, 3 H), 2.04–2.18 (m, 1 H), 1.26–2.01 (m, 19 H), 1.06 (d, J=6.6 Hz, 3 H), 0.94 (t, J=7.3 Hz, 3 H), 0.57 (s, 3 H).

MS m/e=477.3 [M+Na]$^+$.

Example 2

Production of Compound No. 1104

The objective compound was produced in the same way as in Example 1 using the corresponding ketone.

$^1$H NMR (CDCl$_3$) δ: 6.57 (d, J=11 Hz, 1 H), 6.42 (d, J=10 Hz,1 H), 5.87 (d, J=11 Hz,1 H), 5.12 (m, 1 H), 4.98 (m, 1 H), 4.50 (m, 1 H), 4.23 (m, 1 H), 1.10–2.89 (m, 27 H), 1.02 (d, J=6 Hz,3 H), 0.60 (s, 3 H).

Example 3

Production of Compound No. 1105a

The objective compound was produced in the same way as in Example 1 using the corresponding aldehyde and ketone.

$^1$H NMR (CDCl$_3$) δ: 6.67–6.70 (m, 1 H), 6.38 (d, J=10 Hz,1 H), 6.02 (d, J=11 Hz, 1 H), 5.33 (m, 1 H), 5.00 (s, 1 H), 4.43 (m, 1 H), 4.23 (m, 1 H), 1.23–2.85 (m, 29 H), 0.94 (d ,J=6 Hz, 3 H), 0.55 (s, 3 H).

Example 4

Production of Compound No. 1106

The objective compound was produced in the same way as in Example 1 using the corresponding aldehyde and ketone.

$^1$H NMR (CDCl$_3$) δ: 6.61 (m, 1 H), 6.38 (d, J=11 Hz, 1 H), 6.02 (d, J=11 Hz, 1 H), 5.33 (m , 1 H), 5.00 (s, 1 H), 4.43 (m, 1 H), 4.23 (m, 1 H), 1.22–2.85 (m, 31 H), 0.95 (d, J=6 Hz,3 H), 0.54 (s, 3 H).

Example 5

Production of Compound No. 1126

The objective compounds were produced in the same way as in Example 1 using the corresponding ketone. After the deprotection reaction, the crude product was purified by HPLC (column: ODS, solvent: acetonitrile/water) to obtain the objective products (four isomers). Below, data are shown in the order of retention times from the shortest one. The products are optical isomers originated from the carbon atom at the 20-position and the asymmetric carbon of the added ketone.

[Compound No. 1126a]

$^1$H NMR (CDCl$_3$) δ: 6.63 (d, J=10.7 Hz, 1 H), 6.35 (d, J=11.2 Hz, 1 H), 6.00 (d, J=11.2 Hz, 1 H), 5.33 (s, 1 H), 4.99 (s, 1 H), 4.43 (br., 1 H), 4.23 (br., 1 H), 1.00–3.00 (m, 21 H), 1.25 (s, 3 H), 0.96 (d, J=6.8 Hz, 3 H), 0.44 (s, 3 H).

[Compound No. 1126b]

$^1$H NMR (CDCl$_3$) δ: 6.54 (d, J=10.6 Hz,1 H),6.37 (d, J=11.2 Hz,1 H), 6.01 (d, J=11.2Hz,1 H), 5.32 (s, 1 H), 4.98 (s, 1 H), 4.43 (br., 1 H), 4.23 (br., 1 H), 0.88–2.62 (m, 20 H), 1.26 (s, 3 H), 1.06 (d, J=6.6 Hz,3 H), 0.58 (s, 3 H).

[Compound No. 1126c]

$^1$H NMR (CDCl$_3$) δ: 6.64 (dd, J=2.4, 10.8 Hz, 1 H), 6.36 (d, J=11.2 Hz, 1 H), 6.00 (d, J=11.5 Hz, 1 H), 5.32 (s, 1 H), 4.99 (s, 1 H), 4.43 (br., 1 H), 4.23 (br., 1 H), 2.79–2.82 (m, 1 H), 1.21–2.79 (m, 26 H), 0.97 (d, J=6.6 Hz, 3 H), 0.41 (s, 3 H).

[Compound No. 1126d]

$^1$H NMR (CDCl$_3$) δ: 6.56 (d, J=10.2 Hz, 1 H), 6.37 (d, J=11.2 Hz,1 H), 6.01 (d, J=12.2 Hz,1 H), 5.32 (s, 1 H), 4.99 (s, 1 H), 4.44 (m, 1 H), 4.23 (m, 1 H), 2.81–2.87 (m, 1 H), 1.13–2.62 (m, 20 H), 1.27 (s, 3 H), 1.07 (d, J=6.6 Hz,3 H), 0.58 (s, 3 H).

Example 6

Production of Compound No. 1129

The objective compounds were produced in the same way as in Example 1 using the corresponding ketone. After the aldol reaction, the reaction product was divided into two groups of compounds having a lower polarity and a higher polarity, respectively by silica gel column chromatography, both the groups of compounds were subjected to the deprotection reaction, the resultant two crude products were each fractionally purified by HPLC (column: ODS, solvent: acetonitrile/water). Thus, each group obtained a pair of objective products having a lower polarity and a higher polarity. The products are optical isomers originated from the carbon atom at the 20-position and the asymmetric carbon of the added ketone.

[Compound No. 1129a] (lower polarity after aldol reaction and higher polarity by HPLC separation)

$^1$H NMR (CDCl$_3$) δ: 6.37 (d, J=11.1 Hz, 2 H), 6.00 (d, J=11.5 Hz, 1 H), 5.32 (t, J=1.8 Hz, 1 H), 4.99 (s, 1 H), 4.41–4.45 (m, 1 H), 4.19–4.25 (m, 1 H), 2.78–2.83 (m, 2 H), 2.59 (dd, J=3.8, 13.7 Hz, 1 H), 2.17–2.35 (m, 3 H) 1.85–2.11 (m, 7 H), 1.19–1.80 (m, 16 H), 0.94 (d, J=6.6 Hz, 3 H), 0.39 (s, 3 H).

[Compound No. 1129b] (lower polarity after aldol reaction and lower polarity by HPLC separation)

$^1$H NMR (CDCl$_3$) δ: 6.38 (d, J=10.5 Hz, 1 H), 6.20 (d, J=10.0 Hz, 1 H), 6.02 (d, J=11.6 Hz, 1 H), 5.32 (s, 1 H), 4.99 (s, 1 H), 4.43 (m, 1 H), 4.08–4.24 (m, 1 H), 3.75 (br., 1 H), 2.81–2.88 (m, 2 H), 1.23–2.72 (m, 20 H), 1.25 (s, 3 H), 1.02 (d, J=6.6 Hz, 3 H), 0.59 (s, 3 H).

[Compound No. 1129c] (higher polarity after aldol reaction and higher polarity by HPLC separation)

$^1$H NMR (CDCl$_3$) δ: 6.36 (d, J=11.2 Hz, 2 H), 6.01 (d, J=11.2 Hz, 1 H), 5.33 (t, J=1.7 Hz, 1 H), 4.99 (s, 1 H), 4.41–4.46 (m, 1 H), 4.19–4.26 (m, 1 H), 2.78–2.87 (m, 2 H), 2.59 (dd, J=3.5, 13.5 Hz, 1 H), 2.11–2.37 (m, 3 H), 1.86–2.06 (m, 7 H), 1.15–1.78 (m, 16 H), 0.92 (d, J=6.6 Hz, 3 H), 0.46 (s, 3 H).

[Compound No. 1129d] (higher polarity after aldol reaction and lower polarity by HPLC separation)

$^1$H NMR (CDCl$_3$) δ: 6.37 (d, J=11.2 Hz,1 H), 6.29(d, J=9.6 Hz, 1 H), 6.03 (d, J=11.5 Hz, 1 H), 5.32 (s, 1 H), 4.99 (s, 1 H), 4.42 (m, 1 H), 4.23 (m, 1H), 3.71 (br., 1 H), 2.81–2.86 (m, 2 H), 1.23–2.57 (m, 20 H), 1.30 (s, 1 H), 1.04 (d, J=6.6 Hz, 3 H), 0.58 (s, 3 H).

Example 7
Production of Compound No. 1148

The objective compounds were produced in the same way as in Example 1 using the corresponding ketone. After the aldol reaction, the reaction product was divided into two groups of compounds having a lower polarity and a higher polarity, respectively by silica gel column chromatography, both the groups of compounds were subjected to the deprotection reaction, the resultant two crude products were each fractionally purified by HPLC (column: ODS, solvent: acetonitrile/water). Thus, each group obtained a pair of objective products having a lower polarity and a higher polarity. The products are optical isomers originated from the carbon atom at the 20-position and the asymmetric carbon of the added ketone.

[Compound No. 1148a] (lower polarity after aldol reaction and higher polarity by HPLC separation)

$^1$H NMR (CDCl$_3$) δ: 6.63 (dt, J=2.3, 10.4 Hz, 1 H), 6.36 (d, J=11.2 Hz, 1 H), 6.00 (d, J=11.1 Hz, 1 H), 5.32 (s, 1 H), 4.99 (s, 1 H), 4.43 (br., 1 H), 4.23 (br., 1 H), 2.79–2.83 (m, 1 H), 2.52–2.66 (m, 2 H), 2.11–2.44 (m, 4 H), 1.78–2.07 (m, 5 H), 1.16–1.70 (m, 16 H), 0.97 (d, J=6.6 Hz, 3 H), 0.92 (t, J=6.9 Hz, 3 H), 0.41 (s, 3 H).

MS m/e=469.0 [M+1]$^+$.

[Compound No. 1148b] (lower polarity after aldol reaction and lower polarity by HPLC separation)

$^1$H NMR (CDCl$_3$) δ: 6.54 (dt, J=2.6, 10.2 Hz, 1 H), 6.37 (d, J=10.1 Hz, 1 H), 6.01 (d, J=11.6 Hz, 1 H), 5.32 (d, J=1.7 Hz,1 H), 4.98 (s, 1 H), 4.43 (br., 1 H), 4.23 (br., 1 H), 2.81–2.86 (m, 1 H), 2.57–2.66 (m, 2 H), 2.28–2.49 (m, 4 H), 2.07–2.18 (m, 1 H), 1.13–2.00 (m, 20 H), 1.06 (d, J=6.6 Hz, 3 H), 0.92 (t, J=6.9 Hz, 3 H), 0.58 (s, 3 H).

MS m/e=469.6 [M+1]$^+$.

[Compound No. 1148c] (higher polarity after aldol reaction and higher polarity by HPLC separation)

$^1$H NMR (CDCl3) δ: 6.61 (dt, J=2.5, 10.4 Hz, 1 H), 6.36 (d, J=11.2 Hz, 1 H), 6.01 (d, J=11.6 Hz, 1 H), 5.33 (d, J=1.5 Hz,1 H), 4.99 (s, 1 H), 4.44 (br., 1 H), 4.23 (br., 1 H), 2.78–2.83 (m, 1 H), 2.55–2.64 (m, 2 H) 2.05–2.46 (m, 4 H), 1.79–2.02 (m, 5 H), 1.15–1.65 (m, 16 H), 0.97 (d, J=6.6 Hz, 3 H), 0.89 (t, J=6.9 Hz, 3 H), 0.44 (s, 3 H).

MS m/e=469.3 [M+1]$^+$.

[Compound No. 1148d] (higher polarity after aldol reaction and lower polarity by HPLC separation)

$^1$H NMR (CDCl$_3$) δ: 6.53 (dt, J=2.3, 10.4 Hz, 1 H), 6.37 (d, J=11.2 Hz, 1 H), 6.01 (d, J=11.7 Hz, 1 H), 5.33 (d, J=1.7 Hz,1 H), 4.99 (s, 1 H), 4.43 (br., 1 H), 4.23 (br., 1 H), 2.81–2.87 (m, 1 H), 2.52–2.67 (m, 2 H), 2.28–2.43 (m, 4 H), 2.04–2.18 (m, 1 H), 1.65–2.01 (m, 7 H), 1.11–1.57 (m, 13 H), 1.06 (d, J=6.6 Hz, 3 H), 0.91 (t, J=6.9 Hz, 3 H), 0.58 (s, 3 H).

MS m/e=469.0 [M+1]$^+$.

Example 8
Production of Compound No. 1152

The objective compounds were produced in the same way as in Example 1 using the corresponding ketone. After the aldol reaction, the reaction product was divided into two groups of compounds having a lower polarity and a higher polarity, respectively by silica gel column chromatography, both the groups of compounds were subjected to the deprotection reaction, the resultant two crude products were each fractionally purified by HPLC (column: ODS, solvent: acetonitrile/water). Thus, each group obtained a pair of objective products having a lower polarity and a higher polarity. The products are optical isomers originated from the carbon atom at the 20-position and the asymmetric carbon of the added ketone.

[Compound No. 1152a] (lower polarity after aldol reaction and higher polarity by HPLC separation)

$^1$H NMR (CDCl$_3$) δ: 7.24–7.32 (m, 3 H), 7.15–7.18 (m, 2 H), 6.66 (d, J=10.4 Hz, 1 H), 6.35 (d, J=10.9 Hz, 1 H), 5.99 (d, J=11.4 Hz, 1 H), 5.32 (s, 1 H), 4.98 (s, 1 H), 4.43 (br., 1 H), 4.22 (br., 1 H), 2.83 (d, J=1.2 Hz, 2 H), 2.77–2.88 (m, 1 H), 2.50–2.62 (m, 2 H), 2.13–2.34 (m, 4 H), 1.78–2.07 (m, 5 H), 1.14–1.69 (m, 12 H), 0.94 (d, J=6.8 Hz, 3 H), 0.39 (s, 3 H).

MS m/e=517.3 [M+1]$^+$.

[Compound No. 1152b] (lower polarity after aldol reaction and lower polarity by HPLC separation)

$^1$H NMR (CDCl$_3$) δ: 7.20–7.32 (m, 3 H), 7.15–7.18 (m, 2 H), 6.57 (dt, J=2.6, 10.6 Hz, 1 H), 6.37 (d, J=11.2 Hz, 1 H), , 6.00 (d, J=11.1 Hz, 1 H), 5.31 (s, 1 H) 4.98 (s, 1 H), 4.43 (br., 1 H), 4.22 (br., 1 H), 2.82 (d, J=2.1 Hz, 2 H), 2.76–2.86 (m, 1 H), 2.50–2.62 (m, 2 H), 2.12–2.40 (m, 4 H), 1.88–2.06 (m, 4 H), 1.66–1.83 (m, 4 H), 1.11–1.57 (m, 9 H), 1.04 (d, J=6.6 Hz, 3 H), 0.56 (s, 3 H).

MS m/e=517.3 [M+1]$^+$.

[Compound No. 1152c] (higher polarity after aldol reaction and higher polarity by HPLC separation)

$^1$H NMR (CDCl$_3$) δ: 7.21–7.27 (m, 3 H), 7.10–7.13 (m, 2 H), 6.63 (d, J=10.6 Hz, 1 H), 6.37 (d, J=11.2 Hz, 1 H), 6.02 (d, J=11.4 Hz, 1 H), 5.33 (d, J=1.7 Hz, 1 H), 5.00 (s, 1 H), 4.44 (br., 1 H), 4.23 (br., 1 H), 2.84 (s, 2 H), 2.80–2.84 (m, 1 H), 2.50–2.64 (m, 2 H), 2.12–2.35 (m, 4 H), 1.78–2.07 (m, 5 H), 1.20–1.70 (m, 12 H), 0.95 (d, J=6.8 Hz, 3 H), 0.39 (s, 3 H).

MS m/e=517.3 [M+1]⁺.

[Compound No. 1152d] (higher polarity after aldol reaction and lower polarity by HPLC separation)

¹H NMR (CDCl₃) δ: 7.22–7.32 (m, 3 H), 7.10–7.16 (m, 2 H), 6.55 (dt, J=2.3, 10.7 Hz, 1 H), 6.38 (d, J=11.4 Hz, 1 H), 6.02 (d, J=11.2 Hz, 1 H), 5.34 (d, J=1.7 Hz, 1 H), 5.00 (s, 1 H), 4.44 (br., 1 H), 4.24 (br., 1 H), 2.82 (d, J=2.2 Hz, 2 H), 2.77–2.88 (m, 1 H), 2.54–2.65 (m, 2 H), 2.28–2.39 (m, 2 H), 2.13–2.25 (m, 2 H), 1.87–2.08 (m, 4 H), 1.64–1.84 (m, 4 H), 1.13–1.58 (m, 9 H), 1.05 (d, J=6.6 Hz, 3 H), 0.57 (s, 3 H).

MS m/e=517.2 [M+1]⁺.

Example 9
Production of Compound No. 1156

The objective compounds were produced in the same way as in Example 1 using the corresponding ketone. After the aldol reaction, the reaction product was subjected to the deprotection reaction, the crude product was fractionally purified by HPLC (column: ODS, solvent: acetonitrile/water) to obtain a pair of objective products having a lower polarity and a higher polarity. The products are optical isomers originated from the asymmetric carbon of the added ketone.

[Compound No. 1156a] (having lower polarity)

¹H NMR (CDCl₃) δ: 6.43 (m, 1 H), 6.37 (d, J=11 Hz, 1 H), 6.01 (d, J=11 Hz, 1 H), 5.32 (s, 1 H), 4.99 (s, 1 H), 4.43 (m, 1 H), 4.23 (m, 1 H), 3.55–3.64 (m, 2 H), 1.28–2.86 (m, 27 H), 1.06 (m, 3 H), 0.58 (s, 3 H).

[Compound No. 1156b] (having higher polarity)

¹H NMR (CDCl₃) δ: 6.43 (m, 1 H), 6.37 (d, J=11 Hz, 1 H), 6.01 (d, J=11 Hz,1 H), 5.32 (s, 1 H), 4.99 (s, 1 H), 4.43 (m, 1 H), 4.23 (m, 1 H), 3.55–3.64 (m, 2 H), 1.28–2.86 (m, 27 H), 1.09 (m, 3 H), 0.58 (s, 3 H).

Example 10
Production of Compound No. 2101

The objective compound was produced in the same way as in Example 1 using the corresponding ketone.

¹H NMR (CDCl₃) δ: 7.56 (m, 1 H), 6.45 (d, J=11 Hz, 1 H), 6.35–6.40 (m, 2 H), 6.01 (d, J=11 Hz, 1 H), 5.32 (s, 1 H), 4.98 (d, J=10 Hz, 1 H), 4.98 (s, 1 H), 4.42 (m, 1 H), 4.23 (m, 1 H), 3.20 (m, 1 H), 1.13–2.86 (m, 19 H), 1.09 (d, J=6 Hz, 3 H), 0.59 (s, 3 H).

Example 11
Production of compound No. 2104

The objective compounds were produced in the same way as in Example 1 using the corresponding ketone. After the aldol reaction, the reaction product was subjected to the deprotection reaction, the crude product was fractionally purified by HPLC (column: ODS, solvent: acetonitrile/water) to obtain a pair of objective products having a lower polarity and a higher polarity. The products are optical isomers originated from the carbon atom at the 20-position.

[Compound No. 2104a] (having lower polarity)

¹H NMR (CDCl₃) δ: 7.17 (s, 1 H), 6.42 (d, J=11.1 Hz, 1 H), 6.37 (d, J=11.1 Hz, 1 H), 6.00 (d, J=11.1 Hz, 1 H), 5.32 (s, 1 H), 4.98 (s, 1 H), 4.43 (br., 1 H), 4.24 (br., 1 H), 1.85 (s, 3 H), 1.08 (d, J=6.5 Hz, 3 H), 1.00–3.00 (m, 19 H), 0.58 (s, 3 H).

MS m/e=421.1 [M−1]⁺.

[Compound No. 2104b] (having higher polarity)

¹H NMR (CDCl₃) δ: 7.17 (s, 1 H), 6.53 (d, J=11.6 Hz, 1 H), 6.36 (d, J=11.2 Hz, 1 H), 6.00 (d, J=11.2 Hz, 1 H), 5.33 (s, 1 H), 4.99 (s, 1 H), 4.43 (br., 1 H), 4.23 (br., 1 H), 1.85 (s, 3 H), 1.00–3.00 (m, 19 H), 1.00 (d, J=6.6 Hz, 3 H), 0.42 (s, 3 H). MS m/e=444.9[M+23]⁺.

Example 12
Production of Compound No. 1130

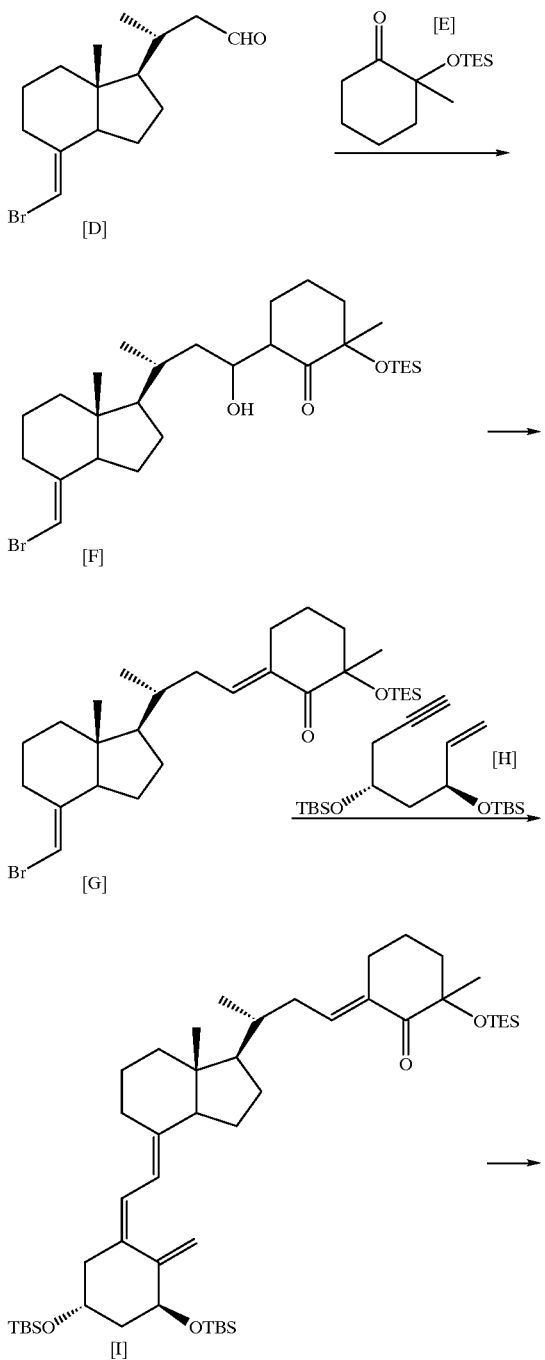

-continued

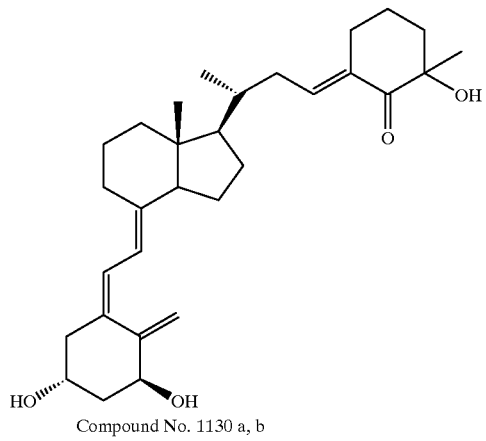

Compound No. 1130 a, b

Under argon atmosphere, 1.15 ml of 1.66 M butyllithium solution in hexane was added to a solution of diisopropylamine (212 mg) in THF, which had been cooled to 0 °C., and the mixture was stirred for 15 min. After the mixture was cooled to −78 °C., a solution of ketone [E] (285 mg) in THF was added, and the resultant mixture was stirred for 20 min. To the reaction mixture was added a solution of the aldehyde [D] (285 mg), which had been produced in Reference Example 2, in THF, and the resultant mixture was stirred for 1 hr. The reaction was stopped by adding 15 ml of a saturated ammonium chloride solution, and then the reaction mixture was extracted with ethyl acetate. The organic layer was washed with brine, dried over magnesium sulfate anhydride and concentrated to obtain crude [F].

The obtained [F] was dissolved in dimethylformamide. To the obtained solution were added dimethylaminopyridine (612 mg) and methanesulfonyl chloride (160 μl) under argon atmosphere at 0° C. The temperature of the mixture was elevated to 50° C., and the mixture was stirred overnight. Then, brine was added to the reaction mixture, and organic matters were extracted with ethyl acetate. The organic layer was washed with brine, dried over magnesium sulfate anhydride and concentrated. The residue was purified by silica gel column chromatography (hexane:ethyl acetate=20:1) to obtain [G] (about 560 mg).

Under argon atmosphere, triphenylphosphine (35.3 mg) and tris(dibenzylideneacetone)palladium(0)-chloroform adduct (22.7 mg) were dissolved in 2 ml of toluene and 2 ml of diisopropylethylamine, and the obtained solution was stirred at room temperature for 20 min. To this solution was added a solution of [G] (90.3 mg) and [H] (165 mg) in a mixed solvent of toluene-diisopropylethylamine, and the resultant mixture was warmed up to 120° C. and stirred for 2 hr. The reaction mixture was allowed to cool down, filtered and concentrated. The residue was purified by silica gel column chromatography (hexane:ethyl acetate=7:1) to obtain [I] (113 mg).

The obtained [I] was dissolved in a mixed solvent of acetonitrile: methylene chloride=3:1, and the resultant solution was cooled to 0° C. Lithium tetrafluoroborate (40 mg) was added, and to the resultant mixture was added dropwise little by little an acetonitrile-diluted sulfuric acid. When the raw material had disappeared, a saturated sodium bicarbonate aqueous solution was added, and the reaction mixture was extracted with methylene chloride. The organic layer was washed with brine and dried over sodium sulfate anhydride. The solution was evaporated, and the residue was purified by silica gel column chromatography (hexane:ethyl acetate=4:1), and subsequently purified by HPLC (column: ODS, solvent:acetonitrile/water) to obtain a pair of the object products having lower polarity and higher polarity. They are isomers originated from an asymmetric carbon of the added ketone [E].

[Compound 1130a] (having lower polarity)
$^1$H NMR (CDCl$_3$) δ: 6.51–6.57 (m, 1 H), 6.38 (d, J=11 Hz, 1 H), 6.02 (d, J=11 Hz, 1 H), 5.33 (d, J=1.3 Hz, 1 H), 5.00 (d, J=1.3 Hz, 1 H), 4.41–4.45 (m, 1 H), 4.20–4.26 (m, 1 H), 3.70 (br., 1 H), 2.77–2.84 (m, 2 H), 2.57–2.63 (m, 1 H), 1.23–2.35 (m, 24 H), 1.31 (s, 3 H), 0.94 (d, J=6.6 Hz, 3 H).
[Compound 1130a] (having higher polarity) $^1$H NMR (CDCl$_3$) δ: 6.51–6.57 (m, 1 H), 6.38 (d, J=11 Hz, 1 H), 6.02 (d, J=11 Hz, 1 H), 5.33 (d, J=1.3 Hz, 1 H), 5.00 (d, J=1.3 Hz, 1 H), 4.41–4.45 (m, 1 H), 4.20–4.26 (m, 1 H), 3.70 (br., 1 H), 2.77–2.84 (m, 2 H), 2.57–2.63 (m, 1 H), 1.23–2.35 (m, 24 H), 1.31 (s, 3 H), 0.94 (d, J=6.6 Hz, 3 H).

Example 13

Production of Compound 1101

The objective compound was produced in the same way as in Example 12 using the corresponding aldehyde and ketone. $^1$H NMR (CDCl$_3$) δ: 6.37 (d, J=10.5 Hz, 2 H), 6.02 (d, J=11.2 Hz, 1 H), 5.32 (s, 1 H), 4.99 (s, 1 H), 4.31–4.43 (m, 1 H), 4.2–4.3 (m, 1 H), 1.2–2.9 (m, 25 H), 1.05 (d, J=6.6 Hz, 3 H), 0.58 (s, 3 H).

Example 14

Production of Compound 1102

The objective compound was produced in the same way as in Example 12 using the corresponding ketone.
$^1$H NMR (CDCl$_3$) δ: 6.56–6.64 (m, 1 H), 6.38 (d, J=11 Hz, 1 H), 6.01 (d, J=11 Hz, 1 H), 5.33 (s, 1 H), 5.00 (s, 1 H), 4.41–4.46 (br., 1 H), 4.21–4.27 (br., 1 H), 2.80–2.85 (m, 1 H), 2.56–2.63 (m, 1 H), 1.20–2.80 (m, 25 H), 0.95 (d, J=6.3 Hz, 3 H), 0.55 (s, 3 H).

Example 15

Production of Compound 1103

The objective compound was produced in the same way as in Example 12 using the corresponding aldehyde and ketone.
$^1$H NMR (CDCl$_3$) δ: 6.53 (t, J=7.6 Hz, 1 H), 6.37 (d, J=11.2 Hz, 1 H), 6.02 (d, J=11.5 Hz, 1 H), 5.33 (s, 1 H), 5.00 (s, 1 H), 4.41–4.46 (m, 1 H), 4.22–4.24 (m, 1 H), 2.70–2.85 (m, 1 H), 1.1–2.7 (m, 28 H), 0.96 (d, J=6.3 Hz, 3 H), 0.54 (s, 3 H).

Example 16

Production of Compound 1107

The objective compound was produced in the same way as in Example 12 using the corresponding aldehyde and ketone.
$^1$H NMR (CDCl$_3$) δ: 6.41 (d, J=10.6 Hz, 1 H), 6.37 (d, J=10.6 Hz, 1 H), 6.01 (d, J=11.2 Hz, 1 H), 5.32 (s, 1 H), 4.98 (s, 1 H), 4.40–4.45 (m, 1 H), 4.19–4.25 (m, 1 H), 2.80–2.86 (m, 1 H), 1.08–2.61 (m, 26 H), 1.02 (d, J=6.6 Hz, 3 H), 0.59 (s, 3 H).

Example 17

Production of Compound 1110

The objective compounds were produced in the same way as in Example 12 using the corresponding aldehyde and ketone. After the deprotection reaction, the crude product was fractionally purified by HPLC (column: ODS, solvent: acetonitrile/water) to obtain a pair of objective products having a lower polarity and a higher polarity. The products are optical isomers originated from the asymmetric carbon of the added ketone.

[Compound No. 1110a] (having lower polarity)

$^1$H NMR (CDCl$_3$) δ: 6.38 (d, J=11 Hz, 2 H), 6.01 (d, J=11 Hz, 1 H), 5.32 (s, 1 H), 4.99 (s, 1 H), 4.43 (br., 1 H), 4.22–4.24 (br., 1 H), 2.80–2.85 (m, 1 H), 2.56–2.69 (m, 1 H), 1.3–2.8 (m, 22 H), 1.13 (d, J=7 Hz, 3 H), 1.06 (d, J=6.6 Hz, 3 H), 0.58 (s, 3 H).

[Compound No. 1110b] (having higher polarity)

$^1$H NMR (CDCl$_3$) δ: 6.39 (d, J=10.3 Hz, 1 H), 6.38 (d, J=11.9 Hz, 1 H), 6.00 (d, J=11.5 Hz, 1 H), 5.32 (s, 1 H), 4.99 (s, 1 H), 4.43 (s, 1 H), 4.24 (s., 1 H), 2.80–2.86 (m, 1 H), 1.3–2.8 (m, 23 H), 1.14 (d, J=6.9 Hz, 3 H), 1.05 (d, J=6.6 Hz, 3 H), 0.57 (s, 3 H).

Example 18

Production of Compound 1112

The objective compounds were produced in the same way as in Example 12 using the corresponding aldehyde and ketone. After the deprotection reaction, the crude product was fractionally purified by HPLC (column: ODS, solvent: acetonitrile/water) to obtain a pair of objective products having a lower polarity and a higher polarity. The products are optical isomers originated from the asymmetric carbon of the added ketone.

[Compound No. 1112a] (having lower polarity)

$^1$H NMR (CDCl$_3$) δ: 6.38 (d, J=11 Hz, 1 H), 6.01 (d, J=11 Hz, 1 H), 5.32 (s, 1 H), 4.99 (s, 1 H), 4.43 (br., 1 H), 4.23 (br., 1 H), 2.81–2.86 (m, 1H), 1.30–2.80 (m, 25 H), 1.04 (d, J=7 Hz, 3 H), 0.96 (t, J=7 Hz, 3 H), 0.57 (s, 3 H).

[Compound No. 1112b] (having higher polarity)

$^1$H NMR (CDCl$_3$) δ: 6.38 (d, J=11 Hz, 1 H), 6.01 (d, J=11 Hz, 1 H), 5.32 (s, 1 H), 4.99 (s, 1 H), 4.43 (br., 1 H), 4.23 (br., 1 H), 2.81–2.86 (m, 1H), 1.30–2.80 (m, 25 H), 1.04 (d, J=7 Hz, 3 H), 0.96 (t, J=7 Hz, 3 H), 0.57 (s, 3 H).

Example 19

Production of Compound 1116

The objective compound was produced in the same way as in Example 12 using the corresponding aldehyde and ketone.

$^1$H NMR (CDCl$_3$) δ: 6.41 (d, J=10.6 Hz, 1 H), 6.37 (d, J=9.6 Hz, 1 H), 6.01 (d, J=11.2 Hz, 1 H), 5.32 (s, 1 H), 4.99 (s, 1 H), 4.43 (s, 1 H), 4.21 (s, 1 H), 1.2–2.9 (m, 23 H), 1.07 (s, 6 H), 1.05 (d, J=5Hz, 3 H), 0.58 (s, 3H).

Example 20

Production of Compound 1127

The objective compounds were produced in the same way as in Example 12 using the corresponding ketone. After the coupling reaction with an ene-yne compound, the crude product was purified by silica gel column chromatography to separate a pair products having a lower polarity and a higher polarity. Each of them were subjected to deprotection reaction to obtain the objective products. They are optical isomers originated from the asymmetric carbon of the added ketone.

[Compound No. 1127a] (obtained from the lower-polarity fraction of silica gel column chromatography)

$^1$H NMR (CDCl$_3$) δ: 6.37 (d, J=11.2 Hz, 1 H), 6.29(d, J=9.6 Hz, 1 H), 6.03 (d, J=11.5 Hz, 1 H), 5.32 (s, 1 H), 4.99 (s, 1 H), 4.42 (m, 1 H), 4.23 (m, 1 H), 3.71 (br., 1 H), 2.81–2.86 (m, 2 H), 1.23–2.57 (m, 20 H), 1.30 (s, 1 H), 1.04 (d, J=6.6 Hz, 3 H), 0.58 (s, 3 H).

[Compound No. 1127b] (obtained from the higher-polarity fraction of silica gel column chromatography)

$^1$H NMR (CDCl$_3$) δ: 6.38 (d, J=10.5 Hz, 1 H), 6.20 (d, J=10.0 Hz, 1 H), 6.02 (d, J=11.6 Hz, 1 H), 5.32 (s, 1 H), 4.99 (s, 1 H), 4.43 (m, 1 H), 4.08–4.24 (m, 1 H), 3.75 (br., 1 H), 2.81–2.88 (m, 2 H), 1.23–2.72 (m, 20 H), 1.25 (s, 3 H), 1.02 (d, J=6.6 Hz, 3 H), 0.59 (s, 3 H).

Example 21

Production of Compound 1128

The objective compounds were produced in the same way as in Example 12 using the corresponding aldehyde and ketone. After the deprotection reaction, the crude product was fractionally purified by HPLC (column: ODS, solvent: acetonitrile/water) to obtain a pair of objective products having a lower polarity and a higher polarity. The products are optical isomers originated from the asymmetric carbon of the added ketone.

[Compound No. 1128a] (having a lower polarity)

$^1$H NMR (CDCl$_3$) δ: 6.72 (t, J=7.6 Hz, 1 H), 6.38 (d, J=11.2 Hz, 1 H), 6.02 (d, J=11.2 Hz, 1 H), 5.33 (s, 1 H), 5.00 (s, 1 H), 4.44 (br., 1 H), 4.23 (br, 1 H), 2.80–2.85 (m, 1 H), 1.15–2.62 (m, 24 H), 1.27 (s, 3 H), 0.96 (d, J=6.3Hz, 3 H), 0.55 (s, 3 H).

[Compound No. 1128b] (having a higher polarity)

$^1$H NMR (CDCl$_3$) δ: 6.72 (t, J=7.6 Hz, 1 H), 6.38 (d, J=11.2 Hz, 1 H), 6.02 (, J=11.2 Hz d, 1 H), 5.33 (s, 1 H), 5.00 (s, 1 H), 4.44 (br., 1 H), 4.23 (br., 1 H), 2.80–2.85 (m, 1 H), 1.15–2.62 (m, 24 H), 1.27 (s, 3 H), 0.96 (d, J=6.3 Hz, 3 H), 0.55 (s, 3 H).

Example 22

Production of Compound 1131

The objective compounds were produced in the same way as in Example 12 using the corresponding aldehyde and ketone. After the deprotection reaction, the crude product was fractionally purified by HPLC (column: ODS, solvent: acetonitrile/water) to obtain a pair of objective products having a lower polarity and a higher polarity. The products are optical isomers originated from the asymmetric carbon of the added ketone.

[Compound No. 1131a] (having lower polarity)

$^1$H NMR (CDCl$_3$) δ: 6.47–6.50 (m, 1 H), 6.38 (d, J=11.2 Hz, 1 H), 6.02 (d, J=11.2 Hz, 1 H), 5.33 (s, 1 H), 5.00 (s, 1 H), 4.43 (m, 1 H), 4.23 (m, 1H), 3.71 (br., 1 H), 2.81 (m, 2 H), 2.58 (m, 1 H), 1.23–2.35 (m, 24 H), 1.30 (s, 3 H), 0.96 (d, J=6.3 Hz, 3 H), 0.55 (s, 3 H).

[Compound No. 1131b] (having higher polarity)

$^1$H NMR (CDCl$_3$) δ: 6.47–6.50 (m, 1 H), 6.38 (d, J=11.2 Hz, 1 H), 6.02 (d, J=11.2 Hz, 1 H), 5.33 (s, 1 H), 5.00 (s, 1 H), 4.43 (m, 1 H), 4.23 (m, 1H), 3.71 (br., 1 H), 2.81 (m, 2 H), 2.58 (m, 1 H), 1.23–2.35 (m, 24 H), 1.30 (s, 3 H), 0.96 (d, J=6.3 Hz, 3 H), 0.54 (s, 3 H).

Example 23

Production of Compound No. 1110c

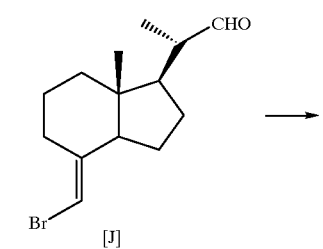

[J]

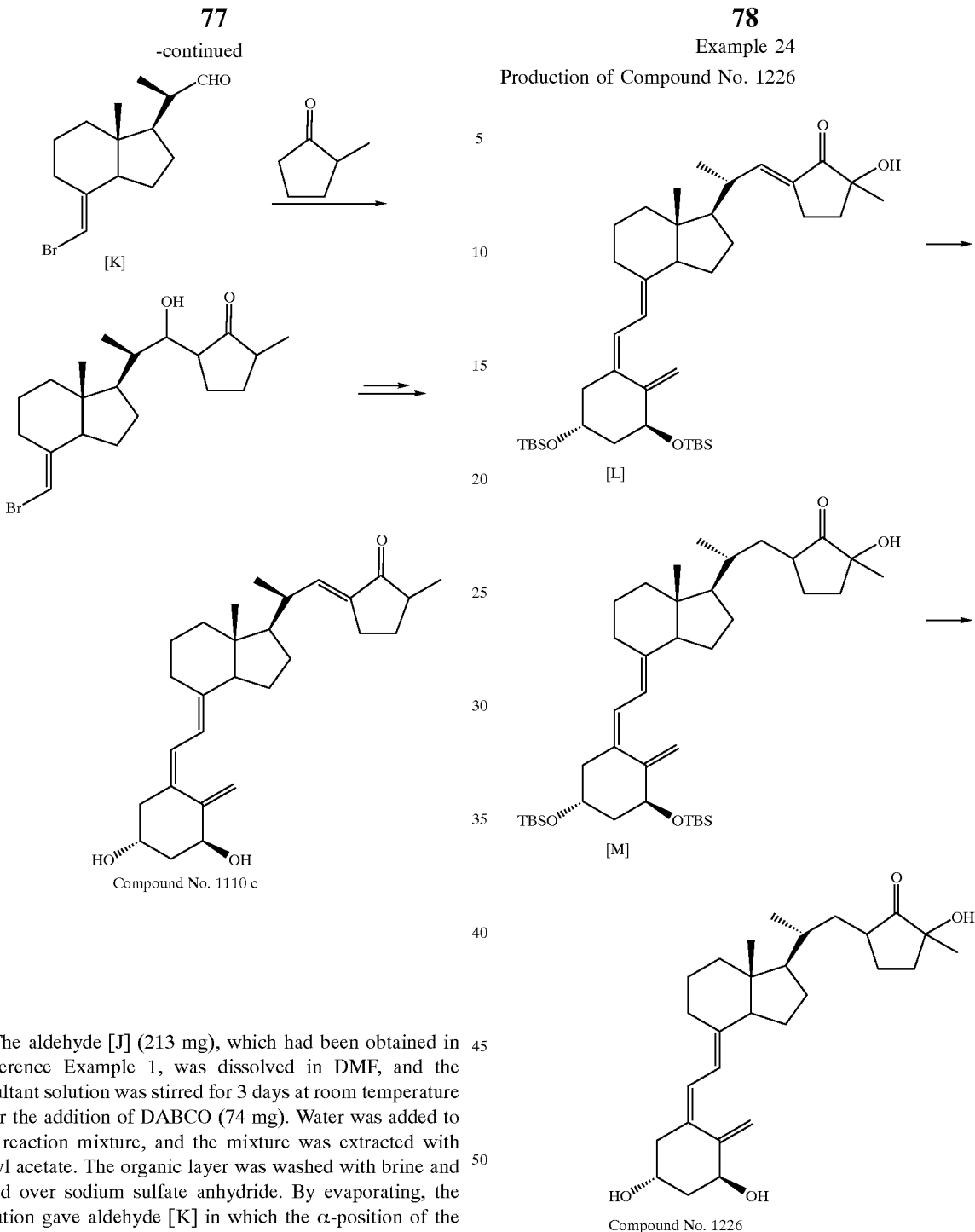

Example 24

Production of Compound No. 1226

The aldehyde [J] (213 mg), which had been obtained in Reference Example 1, was dissolved in DMF, and the resultant solution was stirred for 3 days at room temperature after the addition of DABCO (74 mg). Water was added to the reaction mixture, and the mixture was extracted with ethyl acetate. The organic layer was washed with brine and dried over sodium sulfate anhydride. By evaporating, the solution gave aldehyde [K] in which the α-position of the formyl group of aldehyde [J] had been epimerized. Subsequently, the obtained aldehyde [K] was treated in the same way as in Example 12 by using the corresponding ketone. After the deprotection reaction, the crude product was purified by HPLC (column: ODS, solvent: acetonitrile/water) to obtain the objective product.

$^1$H NMR (CDCl$_3$) δ: 6.46 (d, J=10.2 Hz, 1 H), 6.37 (d, J=10.2 Hz, 1 H), 6.00 (d, J=10.7 Hz, 1 H), 5.32 (s, 1 H), 4.99 (s, 1 H), 4.44 (br., 1 H), 4.23 (br., 1 H), 2.77–2.86 (m, 1 H), 1.2–2.8 (m, 23 H), 1.14 (d, J=6.6 Hz, 3 H), 0.95 (d, J=6.6 Hz, 3 H), 0.42 (s, 3 H).

Sodium borohydride (56.7 mg) was added to 6 ml of pyridine under nitrogen atmosphere, and the mixture was stirred for about 30 min at 70° C. Subsequently, the mixture was cooled to room temperature, and a solution prepared by dissolving [L] (335 mg) in 6 ml of pyridine was added using a syringe to the above-mentioned reductant solution, and the resultant mixture was stirred for about 1 hr at room temperature. The reaction mixture was extracted with ethyl acetate after the addition of 6N hydrochloric acid. The organic layer was washed with a saturated sodium bicarbonate aqueous solution, dried and concentrated. The residue was purified by silica gel column chromatography (hexane:ethyl acetate=3:1) to obtain [M]. This was treated for deprotection reaction according to the method of Example 1, and the crude product was purified by HPLC (column: ODS, solvent: acetonitrile/water) to obtain the objective product.

$^1$H NMR (CDCl$_3$) δ: 6.36 (d, J=11.1 Hz, 1 H), 6.03 (d, J=11.1 Hz, 1 H), 5.34 (s, 1 H), 4.99 (s, 1 H), 1.00–3.00 (m, 24 H), 1.22 (s, 3 H), 0.95 (d, J=5.9 Hz, 3 H), 0.56 (s, 3 H). MS m/e=465.2 [M+23]$^+$.

Example 25
Production of Compound No. 1401

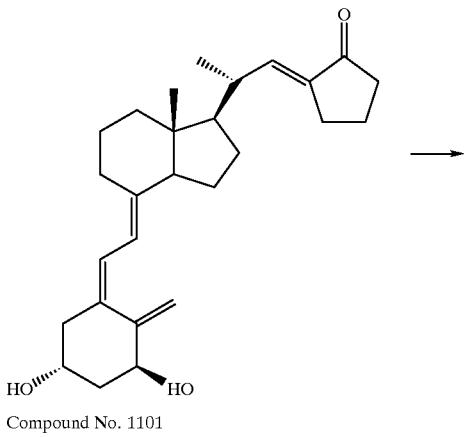

Compound No. 1101

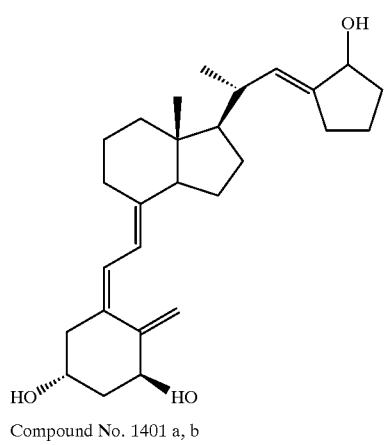

Compound No. 1401 a, b

Under nitrogen atmosphere, 180 μl of 1.01M diisobutylaluminum hydride solution was added dropwise to a methylene chloride solution of the compound No. 1101 (34 mg) which had been cooled to −78° C., and the mixture was stirred for 40 min. After stopping the reaction by slowly adding 0.5 ml of a saturated sodium sulfate aqueous solution, 0.5 ml of methanol and 0.5 ml of 2N hydrochloric acid, and further ethyl acetate and magnesium sulfate were added, and the resultant mixture was stirred for 30 min at room temperature. After filtration, the organic layer was washed with brine and dried. The residue was purified by silica gel column chromatography (hexane:ethyl acetate= 1:1), and further purified by HPLC (column: ODS, solvent: acetonitrile/water) to obtain a pair of the objective products having a lower polarity and a higher polarity. They are optical isomers originated from the asymmetric carbon bound to which the hydroxyl group formed by the reaction is bound.

[Compound No. 1401a] (having a lower polarity)

$^1$H NMR (CDCl$_3$) δ: 6.38 (d, J=11 Hz, 1 H), 6.01 (d, J=11 Hz, 1 H), 5.35 (d, J=10 Hz, 1 H), 5.32 (s, 1 H), 5.00 (s, 1 H), 4.42 (br., 1 H), 4.36 (br., 1 H), 4.21–4.20 (m, 1 H), 2.82 (t-like, 1 H), 2.60 (d-like, 1 H), 2.60 (d-like, 1 H), 1.2–2.4 (m, 23 H), 0.99 (d, J=7.4 Hz, 3 H), 0.57 (s, 3 H).

[Compound No. 1401b] (having a higher polarity)

$^1$H NMR (CDCl$_3$) δ: 6.37 (d, J=11 Hz, 1 H), 6.02 (d, J=11 Hz, 1 H), 5.35 (d, J=10 Hz, 1 H), 5.32 (s, 1 H), 4.99 (s, 1 H), 4.43 (br., 1 H), 4.35 (br., 1 H), 4.11–4.20 (m, 1 H), 2.82 (t-like, 1 H), 2.60 (d-like, 1 H), 2.58 (d-like, 1 H), 1.2–2.4 (m, 23 H), 0.99 (d, J=7.4 Hz, 3 H), 0.57 (s, 3 H).

Example 26

Production of Compound No. 1404

In the same way as in Example 25, the objective compounds were produced using the corresponding ketone. After the reaction, a crude product was fractionally purified by HPLC (column: ODS, solvent: acetonitrile/water) to obtain a pair of the objective products having a lower polarity and a higher polarity. They are optical isomers originated from the asymmetric carbon bound to which the hydroxyl group formed by the reaction is bound.

[Compound No. 1404a] (having a lower polarity)

$^1$H NMR (CDCl$_3$) δ: 6.38 (d, J=11 Hz, 1 H), 6.02 (d, J=11 Hz, 1 H), 5.32 (s, 1 H), 5.13 (d, J=10 Hz, 1 H), 5.00 (s, 1 H), 4.43 (m, 1 H), 4.23 (m, 1 H), 4.08 (m, 1 H), 1.10–2.85 (m, 28 H), 0.97 (d, J=6 Hz, 3 H), 0.59 (s, 3 H).

[Compound No. 1404b] (having a higher polarity)

$^1$H NMR (CDCl$_3$) δ: 6.38 (d, J=11 Hz, 1 H), 6.00 (d, J=11 Hz, 1 H), 5.32 (s, 1 H), 5.13 (d, J=10 Hz, 1 H), 5.00 (s, 1 H), 4.42 (m, 1 H), 4.22 (m, 1 H), 4.06 (m, 1 H), 1.10–2.85 (m, 28 H), 0.98 (d, J=6 Hz, 3 H), 0.58 (s, 3H).

Example 27

Production of Compound No. 1416

In the same way as in Example 25, the objective compounds were produced using the corresponding ketone. After the reaction, a crude product was fractionally purified by HPLC (column: ODS, solvent: acetonitrile/water) to obtain a pair of the objective products having a lower polarity and a higher polarity. They are optical isomers originated from the asymmetric carbon bound to which the hydroxyl group formed by the reaction is bound.

[Compound No. 1416a] (having a lower polarity)

$^1$H NMR (CDCl$_3$) δ: 6.38 (d, J=11 Hz, 1 H), 6.01 (d, J=11 Hz, 1 H), 5.32 (d, J=14 Hz, 1 H), 5.26 (d, J=12 Hz, 1 H), 4.99 (s, 1H), 4.42 (br., 1 H), 4.23 (br., 1 H), 3.83 (s, 1 H), 2.82 (d, J=14 Hz, 1 H), 2.60 (d, J=16 Hz, 1 H), 1.1–2.4 (m, 22 H), 1.01 (s, 3 H), 0.98 (d, J=8 Hz, 3 H), 0.79 (s, 3 H), 0.57 (s, 3 H).

[Compound No. 1416b] (having a higher polarity)

$^1$H NMR (CDCl$_3$) δ: 6.38 (d, J=11 Hz, 1 H), 6.00 (d, J=11 Hz, 1 H), 5.32 (s, 1 H), 5.30 (d, J=12 Hz, 1 H), 5.00 (s, 1 H), 4.43 (br., 1 H), 4.23 (br., 1 H), 3.81 (s, 1 H), 2.83 (d, J=15 Hz, 1 H), 2.61 (d, J=15 Hz, 1 H), 1.1–2.4 (m, 22 H), 0.97 (d, J=7 Hz, 3 H), 0.97 (s, 3 H), 0.84 (s, 3H), 0.57 (s, 3 H).

Example 28
Production of Compounds No. 1426a and No. 1426b

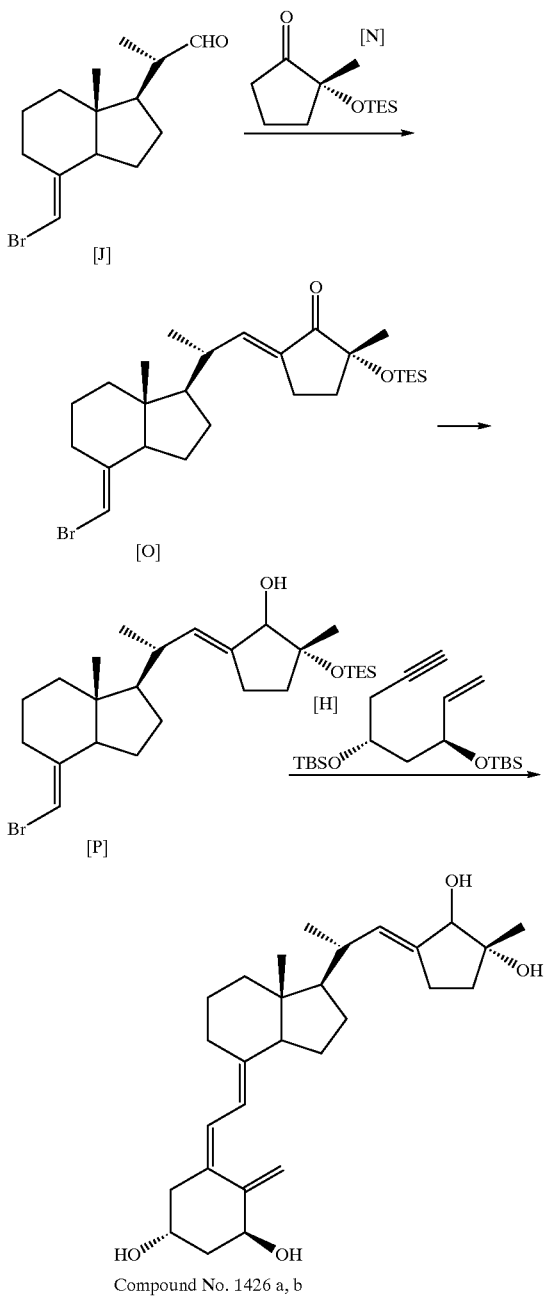

Compound No. 1426 a, b

The aldehyde [J], which had been produced in Reference Example 1, and ketone [N] were converted into an aldol adduct-dehydration product [O] according to the process of Example 12. Under nitrogen atmosphere, [O] (27 mg) was dissolved in 1 ml of ether, and the solution was cooled to −20° C. To the solution was added 0.4 ml of 0.15 M solution of $Zn(BH_4)_2$ in ether (prepared from sodium hydrogen borate and zinc (II) chloride), and the mixture was stirred for 6.5 hr while the temperature was being elevated slowly to room temperature. To the reaction mixture was added a saturated ammonium chloride aqueous solution, and the mixture was extracted with ethyl acetate. The organic layer was washed with brine, dried and concentrated. The residue was purified by silica gel column chromatography (hexane:ethyl acetate=50:1 to 10:1) to obtain a pair of alcohols [P] having a lower polarity and a higher polarity. The alcohols were each allowed to couple with [H] according to a method same as in Example 12, and the reaction products were subjected to deprotection reaction to obtain the objective products. They are optical isomers originated from the asymmetric carbon bound to which the hydroxyl group formed by the reduction reaction of the ketone in this example is bound.

[Compound No. 1426a] (obtained from the fraction of a lower polarity of silica gel column chromatography)

$^1$H NMR (CDCl$_3$) δ: 6.52 (d, J=11 Hz, 1 H), 6.00 (d, J=11 Hz, 1 H), 5.38 (d, J=10 Hz, 1 H), 5.32 (s, 1 H), 4.99 (s, 1 H), 4.34 (br., 1 H), 4.23 (br., 1 H), 3.91 (m, 1 H), 3.91 (br., 1 H), 2.83 (d, J=14 Hz, 1 H), 2.60 (d, J=10 Hz, 1 H), 1.23–2.27 (m, 19 H), 1.27 (s, 3 H), 0.99 (d, J=6.5 Hz, 3 H), 0.56 (s, 3 H).

[Compound No. 1426b] (obtained from the fraction of a higher polarity of silica gel column chromatography)

$^1$H NMR (CDCl$_3$) δ: 6.37 (d, J=11 Hz, 1 H), 6.01 (d, J=11 Hz, 1 H), 5.37 (m, 1 H), 5.32 (s, 1 H), 4.99 (s, 1 H), 4.41–4.45 (m, 1 H), 4.22–4.24 (m, 1 H), 4.06 (br., 1 H), 2.80–2.85 (m, 1 H), 2.58–2.63 (m, 1 H), 1.19 (s, 3 H 0.85–2.35 (m, 19 H), 0.97 (d, J=6.5 Hz, 3 H), 0.57 (s, 3 H).

Example 29

Production of Compounds No. 1426c and No. 1426d

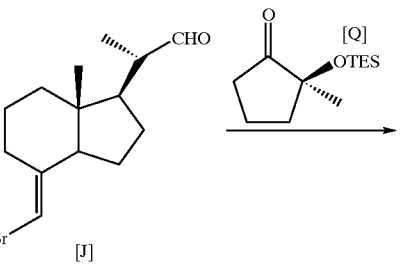

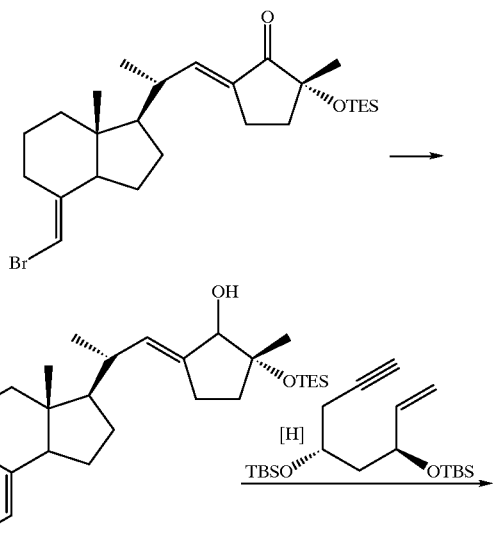

83 -continued

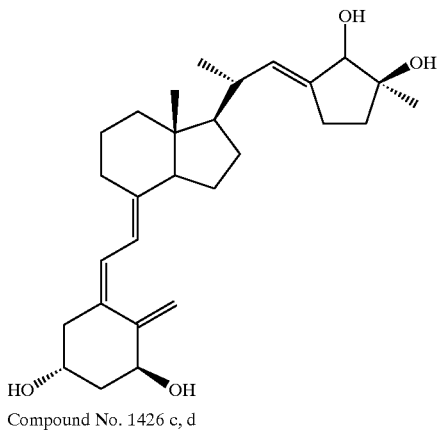

Compound No. 1426 c, d

The objective compounds were produced in the same way as in Example 28 except that ketone [Q] was used in place of the ketone [N]. The compounds are optical isomers originated from the asymmetric carbon bound to which the hydroxyl group formed by the reduction reaction of the ketone in this example is bound.

[Compound No. 1426c] (obtained from the fraction of a lower polarity of silica gel column chromatography)

$^1$H NMR (CDCl$_3$) δ: 6.38 (d, J=7.0 Hz, 1 H), 6.02 (d, J=7.0 Hz, 1 H), 5.39 (d, J=12 Hz, 1 H), 5.32 (s, 1 H), 5.00 (s, 1 H), 4.44 (br., 1 H), 4.23 (br., 1 H), 3.89 (br., 1 H), 3.49 (s, 1 H), 2.83 (m, 1 H), 0.93–3.49 (m, 20 H), 1.26 (s, 3 H), 0.99 (d, J=6.5 Hz, 3 H) , 0.57 (s, 3 H).

[Compound No. 1426d] (obtained from the fraction of a higher polarity of silica gel column chromatography)

$^1$H NMR (CDCl$_3$) δ: 6.37 (d, J=7.0 Hz, 1 H), 6.01 (d, J=7.0 Hz, 1 H), 5.37 (m, 1 H), 5.32 (s, 1 H), 4.99 (s, 1 H), 4.45 (m, 1 H), 4.23 (m, 1 H), 4.08 (br., 1 H), 2.83 (m, 1 H), 2.69 (m, 1 H),1.01–2.33 (m, 19 H), 1.17 (s, 3 H), 1.00 (d, J=6.6 Hz, 3 H), 0.57 (s, 3 H).

Example 30

Production of Compound No. 1716

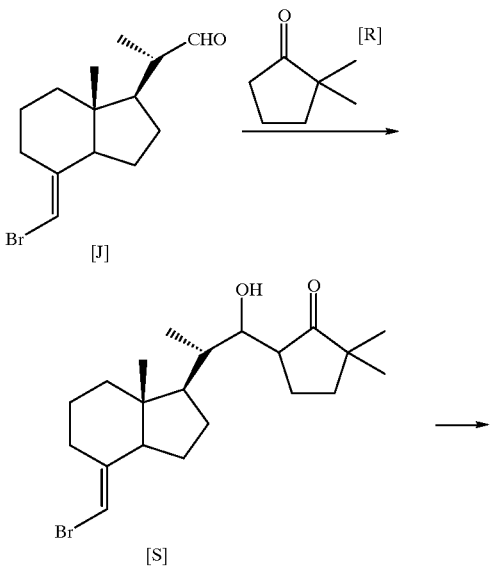

84 -continued

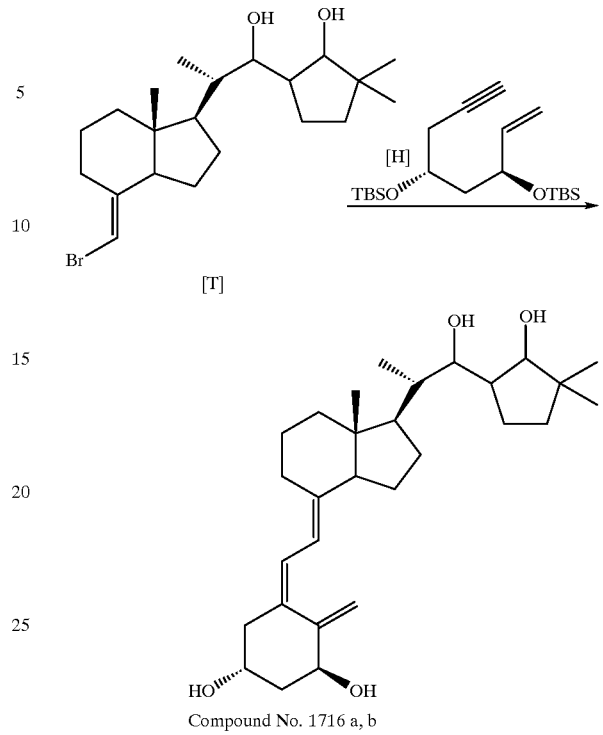

Compound No. 1716 a, b

The aldehyde [J], which had been produced in Reference Example 1, and ketone [R] were converted into an aldol adduct [S] according to a method same as in Example 12. According to the method same as in Example 25, the obtained adduct [S] was reduced to obtain a pair of alcohols [T] having a lower polarity and a higher polarity. The alcohols were allowed to couple with [H] according to the same method as in Example 12, and the reaction products were subjected to deprotection reaction to obtain the objective products. They are optical isomers originated from the asymmetric carbon bound to which the hydroxyl group formed by the reduction reaction of the ketone in this example is bound.

[Compound No. 1716a] (obtained from the fraction of a lower polarity of silica gel column chromatography)

$^1$H NMR (CDCl$_3$) δ: 6.33 (d, J=12 Hz, 1 H), 6.09 (d, J=11 Hz, 1 H), 5.29 (dd, J=1.3, 2.3 Hz, 1 H), 4.90 (d,, J=1 Hz, 1 H), 4.35 (br., 1 H), 4.07 (br., 1 H), 3.56 (d, J=10 Hz, 1 H), 3.29–3.31 (m, 2 H), 1.2–2.9 (m, 25H), 1.00 (s, 3 H), 0.93 (d, J=6 Hz, 3 H), 0.92 (s, 3 H), 0.57 (s, 3 H).

[Compound No. 1716b] (obtained from the fraction of a higher polarity of silica gel column chromatography)

$^1$H NMR (CDCl$_3$) δ: 6.33 (d, J=11 Hz, 1 H), 6.09 (d, J=11 Hz, 1 H), 5.30 (t, J=1.6 Hz, 1 H), 4.91 (d, J=1.6 Hz, 1 H), 4.36 (t, J=6 Hz, 1 H), 4.13 (br., 1 H), 3.82 (d, J=10 Hz, 1 H), 3.64 (d, J=4 Hz, 1 H), 3.31 (t, J=1.7 Hz, 2 H), 1.25–2.90 (m, 24 H), 1.04 (s, 3 H), 0.95 (s, 3 H), 0.93 (d, J=7 Hz, 3 H), 0.57 (s, 3 H).

Example 31
Production of Compound No. 1126e

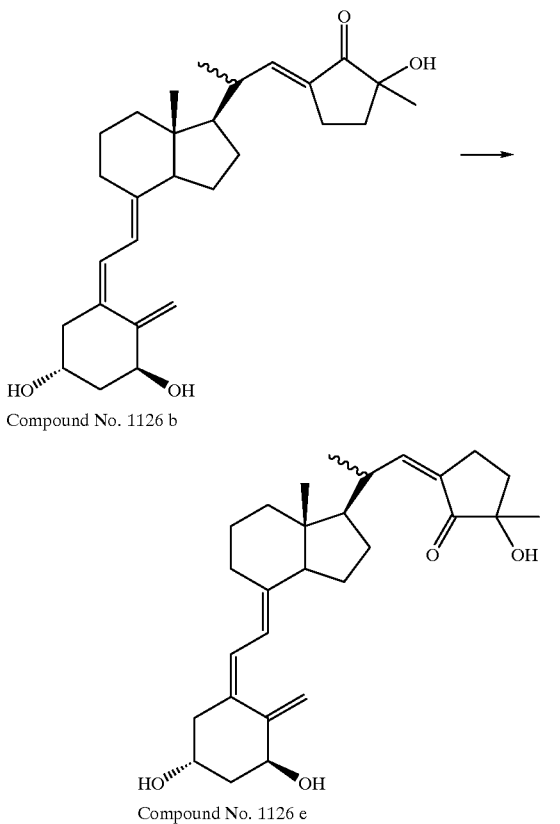

Compound No. 1126 b

Compound No. 1126 e

The compound No. 1126b (41 mg) was dissolved in 5 ml of toluene and 5 ml of ethanol, and the obtained solution was irradiated with ultraviolet rays of 350 nm for 6 hr in nitrogen atmosphere after the addition of anthracene (38.5 mg) and triethylamine (3 ml). The treated solution was concentrated under reduced pressure, the concentrate was purified by silica gel column chromatography and further by HPLC to obtain the objective product.

$^1$H NMR (CDCl$_3$) δ: 6.37 (d, J=11 Hz, 1 H), 6.02 (d, J=11 Hz, 1 H), 5.62 (dt, J=2, 11 Hz, 1 H), 5.32 (m, 1 H), 4.99 (s, 1 H), 4.42 (m, 1 H), 4.22 (m, 1 H), 3.69–3.75 (m, 2 H), 1.24 (m, 3 H), 1.28–2.82 (m, 22 H), 0.99 (d, J=6 Hz, 3 H), 0.63 (s, 3 H).

Example 32
Production of Compound No. 1126f

The objective compound was produced using the compound No. 1126c in the same way as in Example 31.

$^1$H NMR (CDCl$_3$) δ: 6.34 (d, J=10 Hz, 1 H), 5.96–6.02 (m, 2 H), 5.32 (m, 1 H), 4.98 (s, 1 H), 4.43 (m, 1 H), 4.22 (m, 1 H), 3.73 (m, 1 H), 3.58 (m, 1H), 1.22 (m, 3 H), 1.18–2.83 (m, 22 H), 0.96 (d, J=6 Hz, 3 H), 0.36 (s, 3H).

Example 33
Production of Compound No. 1105b

The objective compound was produced in the same way as in Example 31 using the compound No. 1105a.

$^1$H NMR (CDCl$_3$) δ: 6.38 (d, J=11 Hz, 1 H), 6.01 (d, J=10 Hz, 1 H), 5.60 (m, 1 H), 5.32 (s, 1 H), 5.00 (s, 1 H), 4.43 (m, 1 H), 4.23 (m, 1 H), 1.22–2.85 (m, 29 H), 0.91 (d, J=6 Hz, 3 H), 0.55 (s, 3 H).

Example 34

Production of Compound No. 1606a

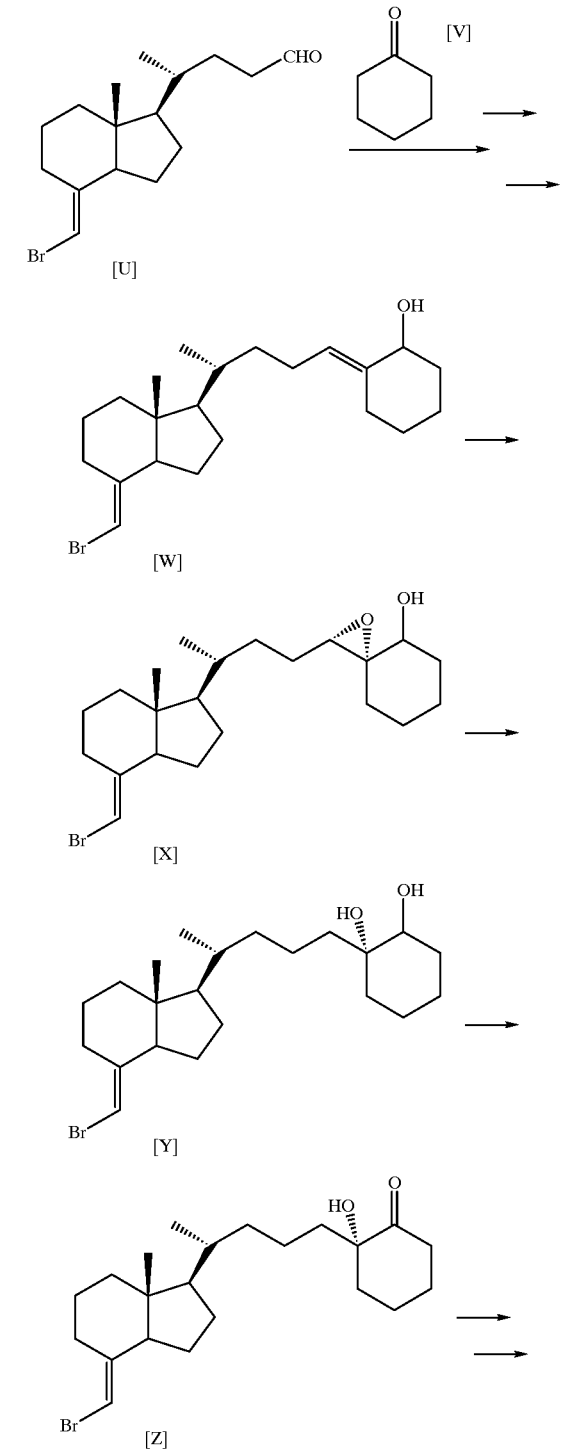

87

-continued

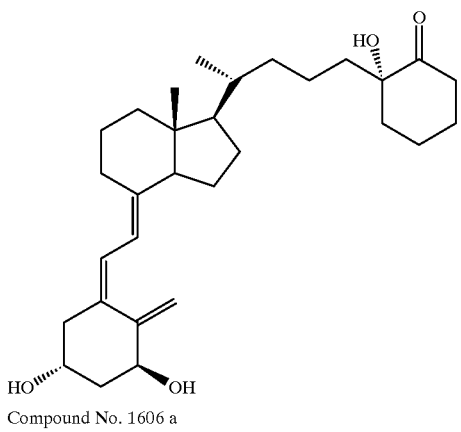

Compound No. 1606 a

According to the method of Example 12, aldehyde [U] and ketone [V] were made to react with each other to obtain alcohol [W].

A solution of titanium tetraisopropoxide (69.1 mg) in 2 ml of methylene chloride was cooled to −23° C. in the presence of molecular sieve 4A (100 mg), and a solution of L-(+)-tartaric acid diisopropyl ester (68.8 mg) in 2 ml of methylene chloride was added to the above solution, and subsequently a solution of the alcohol [W] (106 mg) in 2 ml of methylene chloride was added. Further, 0.044 ml of a 3M solution of t-butylhydroperoxide in 2,2-dimethyl-4-methylpentane was added, and the mixture was stirred for 2 hr. After the addition of methanol, a saturated sodium bicarbonate aqueous solution and a saturated sodium thiosulfate aqueous solution were added, and the mixture was warmed up to room temperature. The reaction mixture was filtered through celite, the filtrate was extracted with ethyl acetate. The combined organic layer was washed with brine, dried over sodium sulfate and concentrated. The residue was purified by silica gel column chromatography to obtain [X].

A solution of the obtained [X] (41.8 mg) in 2 ml of diethyl ether was added to a suspension of lithium aluminum hydride (5.5 mg) in 0.5 ml of diethyl ether, and further lithium aluminum hydride (6.6 mg) was added until [X] was disappeared. A saturated sodium sulfate aqueous solution was added to the reaction mixture to stop the reaction until hydrogen generation ceased, and after diluted with diethyl ether, the reaction mixture was filtered through celite to remove insoluble matters, and the insoluble matters were further washed with ethyl acetate. The combined organic layer was concentrated under reduced pressure, and the residue was purified by silica gel column chromatography to obtain [Y].

To the ice-cold solution of [Y] (13.7 mg) in methylene chloride was added about 3 ml of an oxidant, which had been prepared from sulfur trioxide pyridine complex, dimethyl sulfoxide, triethylamine and methylene chloride at ratios of 50.9 mg : 0.109 ml: 0.152 ml: 1 ml. The mixture was stirred for 8 hr, water was added to stop the reaction, and the reaction mixture was extracted with ethyl acetate. The combined organic layer was washed sequentially with a saturated potassium hydrogen sulfate aqueous solution, water and brine, dried over sodium sulfate, and concentrated. The residue was purified by silica gel column chromatography to obtain [Z].

The obtained [Z] was subjected to a coupling reaction with an ene-yne compound by the same method as in Example 12, and the product was treated for deprotection to obtain the objective product. $^1$H NMR (CDCl$_3$) δ: 6.38(d,

88

J=10.9 Hz, 1 H), 6.01 (d, J=11.2 Hz, 1 H), 5.33 (s, 1 H), 5.00 (s, 1 H), 4.41–4.45 (m, 1 H), 4.23–4.25 (m, 1 H), 3.97 (s, 1 H), 2.80–2.84 (m, 1 H), 0.92–2.62 (m, 30 H), 0.90 (d, J=6.3 Hz, 3 H), 0.53 (s, 3 H).

Example 35

Production of Compound No. 1606b

The objective compound was obtained by using L-(−)-tartaric acid diisopropyl in stead of L-(+)-tartaric acid diisopropyl in the stage of the epoxidation in Example 34. This compound is the optical isomer of the compound No. 1606a originated from the asymmetric carbon to which the hydroxyl group formed by the ring opening reaction of the epoxy ring in the present example is bound.

$^1$H NMR (CDCl$_3$) δ: 6.38 (d, J=11.2 Hz, 1 H), 6.01 (d, J=11.2 Hz, 1 H), 5.33 (s, 1 H), 5.00 (s, 1 H), 4.43 (dd, J=4.6, 7.6 Hz, 1 H), 4.20–4.26 (m, 1 H), 3.98 (s, 1 H), 2.82(dd, J=3.3, 11.9 Hz, 1 H), 2.60 (dd, J=3.5, 13.4 Hz, 1 H), 2.46–2.50 (m, 2 H), 0.76–2.35 (m, 26 H), 0.90 (d, J=5.9 Hz, 3 H), 0.53 (s, 3 H).

Example 36

Production of Compound No. 1132

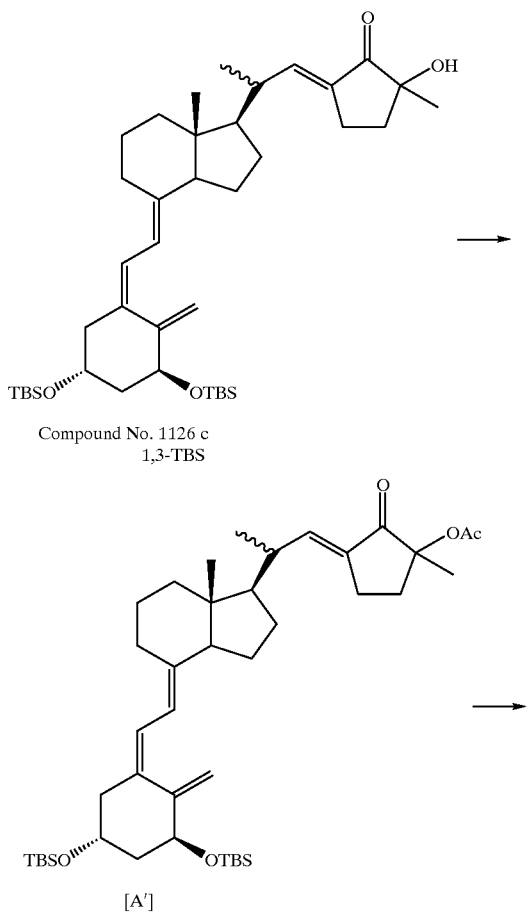

Compound No. 1126 c
1,3-TBS

[A']

-continued

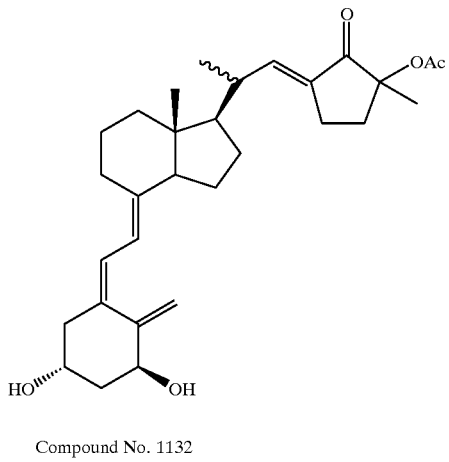

Compound No. 1132

The 1,3-TBS protected compound (67 mg) of the compound No. 1126c obtained in Example 5 was dissolved in 1.5 ml of chloroform. To the resultant solution were added triethylamine (80 mg), acetyl chloride (48 mg) and dimethylaminopyridine (12 mg), and the mixture was stirred at room temperature for 5 hr. The reaction mixture was purified by silica gel column chromatography to obtain [A]. The product was dissolved in 1.5 ml of methanol, PPTS polymer (5 mg) was added, and the mixture was stirred at room temperature overnight. The reaction mixture was filtered, the filtrate was concentrated, and the residue was purified by HPLC to obtain the objective product.

$^1$H NMR (CDCl$_3$) δ: 6.60 (d, J=10.7 Hz, 1 H), 6.37 (d, J=11.1 Hz, 1 H), 6.00 (d, J=10.7 Hz, 1 H), 5.32 (s, 1 H), 4.99 (s, 1 H), 4.45 (br., 1 H), 4.22 (br., 1 H), 2.56–2.81 (m, 3 H), 2.26–2.41 (m, 4 H), 1.87–2.07 (m, 5 H), 2.04 (s, 3 H), 1.19–1.78 (m, 11 H), 1.38 (s, 3 H), 0.97 (d, J=6.4 Hz, 3 H), 0.46 (s, 3 H).

Example 37
Production of Compound No. 1138

According to a method similar to Example 36, the objective compound was produced by using butanoyl chloride in stead of the acetyl chloride.

$^1$H NMR (CDCl$_3$) δ: 6.59 (d, J=10.6 Hz, 1 H), 6.37 (d, J=11.4 Hz, 1 H), 6.00 (d, J=11.2 Hz, 1 H), 5.32 (t, J=1.7 Hz, 1 H), 4.99 (s, 1 H), 4.43 (br., 1 H), 4.22 (br., 1 H), 2.69–2.82 (m, 2 H), 2.40–2.62 (m, 1 H), 2.24–2.39 5 H), 1.68–2.06 (m, 6 H), 1.13–1.65 (m, 16 H), 0.97 (d, J=6.6 Hz, 3 H), 0.93 (t, J=7.3 Hz, 3 H), 0.46 (s, 3 H).

Example 38
Neutrophilic Infiltration Suppressing Effect Assayed by Using Hamster LPS-Induced Airway Inflammatory Model A male golden hamster is placed in an inhalation chamber (volume: 12 liter) and allowed to inhale LPS (nebulizer filled concentration: 2.0 mg/ml) generated by an ultrasonic nebulizer for 30 min to cause airway inflammatory. Just after the inhalation of the LPS, a compound of the present invention is administered through intrarespiratory tract administration or orally at a dosage of 20 μg/kg under halothane anesthesia. After 24 hr, tracheal branches and pulmonary alveoli were washed, and the number of neutrophils in the washing were determined. Using the number of neutrophils obtained in the absence of a compound of the present invention as the control, the decreasing rates of the numbers of neutrophils were expressed in terms of percent suppression based on the control.

The results are shown in Table 3 (intrarespiratory tract administration) and in Table 4 (oral administration).

TABLE 3

Neutrophilic infiltration suppressing effect assayed by using hamster LPS-induced airway inflammatory model (intrarespiratory tract administration)

| % Suppression | Compound No. |
|---|---|
| >40% | 1105b, 1107, 1110b, 1112a, 1112b, 1116*, 1126a, 1126b, 1126c, 1126e, 1126f, 1127a, 1144b, 1144d, 1156a, 1156b, 1226, 1401a, 1606a, 2101, 2104a |
| 20–40% | 1426c*, 1129d*, 1716a, 1128b, 1126d |
| <20% | 1101 |

*assayed at a dosage of 1 μg/kg

TABLE 4

Neutrophilic infiltration suppressing effect assayed by using hamster LPS-induced airway inflammatory model (oral administration)

| % Suppression | Compound No. |
|---|---|
| >40% | 1116, 1126b, 1226, 2104a |
| 20–40% | 1110b |
| <20% | |

This model is widely used as an inflammatory pulmonary disease model (Esbenshade, A. M., et al., J. Appl. Physiol., 53, 967–976 (1982)), and it has been reported that the model exhibits a morbid state of acute aggravation of an inflammatory pulmonary disease (Hurlar, L. M., et al., J. Appl. Physiol., 54, 1463–1468 (1983)).

From the results of Table 3 and Table 4, it has been found that compounds of the present invention have neutrophilic infiltration suppressing effect in the model. These results have demonstrated that compounds of the present invention are effective as treating agents for inflammatory respiratory diseases.

Example 39
Differentiation Induction Effect to Human Leukemia Cell, HL-60 Cell

HL-60 cell line that had been purchased from a cell bank was used. The cell line was stored as a frozen storage stock for preventing the change of cell characteristics attributable to successive cultivations. Prior to the initiation of experiments, the cells were defrosted and successive culturing was stared, and such cells were used. The successive culturing was carried out by centrifugally recovering cells which were in the state of suspension culture, and diluting the collected cell concentrate by a fresh culture medium at a ratio of about 1/100 (1–2×10$^4$cells/ml). As the culture medium, an RPMI-1640 medium containing 10% fetal bovine serum was used. Thus, cells which were in the successive culturing were centrifugally collected, and they were dispersed in a culture medium at the concentration of 2×10$^4$ cells/ml. The dispersion was seeded into a 24-well culture schale at 1 ml/well. An ethanol solution (1×10$^{-5}$M) of a compound of the present invention was added to this system at 1 μl/well (the final concentration of the compound: 1×10$^{-8}$M). For the control, ethanol was added at 1 μl/well. After culturing at 37° C. for 4 days in 5% CO$_2$ atmosphere, the cells were centrifugally collected.

Nitroblue tetrazolium (NBT) reduction activity was determined as follows. That is, the centrifugally collected cells were suspended in a fresh culture medium, and NBT and 12-O-tetradecanoylphorbol-13-acetate (TPA) were added to the resultant suspension so that their concentrations became 0.1% and 100 nM, respectively. After the mixed suspension was incubated at 37° C. for 25 min, a cytospin sample was prepared. After air drying, it was stained with Kernechtrot, and the ratio of the positive cells of NBT reduction activity was determined under an optical microscope. The results are shown in Table 5.

TABLE 5

Differentiation induction effect to human leukemia cell, HL-60 cell

| Ratio of cells positive in NTB reduction activity | Compound No |
|---|---|
| >50% | 1126b, 1129d, 1131a, 1131b |
| 10–50% | 1127a, 1128a, 1128b, 1129b, 1130a |
| <10% | 1126d, 1127b, 1130b |

Thus, it has been found that compounds of the present invention have differentiation induction effect to tumor cell.

Example 40

Growth Suppression Effect to Human Colon Cancer Cell, HT-29 Cell

HT-29 cell Line that had been purchased from a cell bank was used. The cell line was stored as a frozen storage stock for preventing the change of cell characteristics attributable to successive cultivations. Prior to the initiation of experiments, the cells were defrosted and successive culturing was stared, and such cells were used. The successive culturing was carried out by centrifugally recovering cells which were in the state of suspension culture, and diluting the collected cell concentrate by a fresh culture medium at a ratio of about 1/100 ($1-2 \times 10^4$ cells/ml). As the culture medium, an RPMI-1640 medium containing 10% fetal bovine serum was used. Thus, cells which were in the successive culturing were centrifugally collected, and they were dispersed in a culture medium at the concentration of $2.5 \times 10^3$ cells/ml. The dispersion was seeded into a schale of 35 mm in diameter at an amount of 2 ml/shale. A $1 \times 10^{-4}$ to $1 \times 10^{-3}$ M ethanol solution of the compound No. 1126b, as a compound of the present invention, was added to this system in an amount of 2 µl to every schale (the final concentration of the compound: $1 \times 10^{-7}$ to $1 \times 10^{-6}$ M). For the control, ethanol was added at a ratio of 2 µl per schale. After culturing at 37° C. for 10 days in 5% $CO_2$ atmosphere, the culture medium was removed, and the cells were washed with PBS and fixed on the schale with a 10% formalin buffer solution. The cells were washed with water, air-dried and stained with a crystal violet solution. After dyeing, the cells were washed with water and air-dried. The relative absorbance (vs. 100 of the absorbance of the schale of the control) of the schale of the compound was measured to determine the relative cell growth rate. The results are shown in Table 6.

TABLE 6

Growth suppression effect to human colon cancer cell, HT-29 cell

| Compound | Concentration (M) | Relative degree of cell growth (%) mean ± SD (n = 4) |
|---|---|---|
| Control | — | 100 |
| No. 1126b | $10^{-7}$ | 85.5 ± 1.9 |
| | $5 \times 10^{-7}$ | 63.0 ± 1.6 |
| | $10^{-6}$ | 59.0 ± 0.0 |

The above results show that a compound of the present invention can dose-relatedly suppress the growth of cancer cells.

Example 41

Effect on the Increase of Blood Calcium Concentration in Repeated Oral Administration to Rats Male SD rats (6 weeks of age, Japan SLC, inc.) were used. Feed for animal raising (MF, Oriental Yeast Industry Co. Ltd.) and water (well water treated with 0.4±0.2 ppm of hypochlorite) were given ad libitum trough out the experiment. The animals were housed individually in suspension-type rat cages and raised at 24±2° C. at a relative humidity of 55±5%. A control group was orally administered pure vehicle (0.1% Triton X-100) for 2 weeks. Active groups were orally administered 1 α, $25(OH)_2D_3$ in an amount of 0.1–0.5 µg/kg/day or the compound No. 1126b of the present invention in an amount of 2–10 µg/kg/day, as test agents for 2 weeks. After about 24 hr of the final administration, blood was collected from an eyeground under ether anesthesia using a heparinized glass micro capillary, and the calcium concentration in the separated plasma was determined by an autoanalyzer (model AU-600, Olympus). The results are shown in Table 7.

TABLE 7

Effect on the increase of blood calcium concentration in repeated oral administration to rats

| Compound | Dose (µg/kg/day) | Blood Ca conc. (mg/dl) mean ± SD |
|---|---|---|
| Control | — | 10.7 ± 0.4 (n = 5) |
| 1α,25(OH)$_2$D$_3$ | 0.1 | 10.7 ± 0.1 (n = 5) |
| | 0.5 | 11.6 ± 0.1 (n = 3)** |
| No. 1126b | 2 | 10.6 ± 0.4 (n = 5) |
| | 10 | 11.1 ± 0.3 (n = 5) |

**Statistically significant difference to the control group is observed (Dunnett's test, 1% in significance level)

While the calcium concentration in the control group was about 10.7 mg/dl, the calcium concentration was clearly increased to about 11.6 mg/dl in the 1 α, $25(OH)_2D_3$ administration group at a dose of 0.5 µg/kg/day. On the other hand, in the compound No. 1126b administration group, the increase of the calcium concentration was not observed at all at a dose of 2 µg/kg/day, and the slight increase of the calcium concentration was observed at a dose of 10 µg/kg/day, the difference being not statistically significant.

From the result, it has been found that the effect on the increase of blood calcium concentration in repeated oral administration of a compound of the present invention is extremely reduced compared with 1 α, $25(OH)_2D_3$.

Example 42

Anti-Malignant Tumor Effect and Blood Calcium Concentration Increase Effect using Mouse which has been Transplanted Tumor Cells under the Renal Capsule Male ICR mice (6 weeks of age, Carles River Japan Ltd.) were used. Feed for animal raising (MF, Oriental Yeast Industry Co. Ltd.) and water (well water treated with 0.4±0.2 ppm of hypochlorite) were given ad libitum trough out the experiment. The animals were housed in polycarbonate-made raising cages and raised at 23±1° C. at a relative humidity of 55±10%. As the human malignant tumor cells to be transplanted under the renal capsule, HL-60 cell line used in Example 39 and HT-29 cell line used in Example 40 were used. The transplantation under the renal capsule and the evaluation of the growth suppressing effect of transplanted malignant tumor cell conglomerates were carried out according to the methods of Fingert, et al. (Cancer Res., 47, 3824–3829 (1987)) and Tanaka, et al. (Cancer Res., 54, 5148–5153 (1994)). The day before the operation, cyclophosphamide (150 mg/kg) was intraperitoneally administered to the mice. The HL-60 cells and HT-29 cells to be transplanted were treated according to the following method to form fibrin coagulates. That is, cells were centrifugally collected, washed with a phosphate buffer solution, then suspended in a serum free RPMI-1649 medium and incubated at 37° C. for 10 min after the addition of fibrinogen (20 mg/ml) and thrombin (20 U/ml). Solidified cell aggregates were finely cut into cubes of about 1.5 mm under a stereoscopic microscope equipped with an ocular micrometer. The finely cut cell aggregates were preserved in an ice-cooled RPMI- 1640 medium before the transplantation. The transplantation was performed by cutting the left rear back side of a mouse under nembutal anesthesia about 1 cm wide, pulling out the left kidney, forming a small cut line on it, and inserting a cell aggregate under renal capsule from the cut line by using a transplantation needle (Natsume Ltd.). From the next day of the operation, cyclosporin A (100 mg/kg) was intraperitoneally administered to all the animals. A control group was orally administered pure vehicle (0.1% Triton X-100) for 2 weeks. Active groups were orally administered 1 α, 25(OH)$_2$D$_3$ in an amount of 1 μg/kg/day or the compound No. 1126b of the present invention in an amount of 10 or 20 μg/kg/day, as test agents, for 2 weeks. After about 24 hr of the final administration, blood was collected from the heart under nembutal anesthesia, and the calcium concentration in the separated serum was determined by an autoanalyzer (model 7070, Hitachi, Ltd.). Further, after the blood collection from the heart, the left kidney was taken out and fixed with a 10% neutral buffer formalin solution, and the size of the implanted malignant tumor cell aggregate was determined under a stereoscopic microscope using a micrometer. As an indicator of the size of the transplanted cell aggregate, a tumor area (the scale of the micrometer of the aggregate in the renal major axis direction × the scale of the micrometer of the aggregate in the renal minor axis direction) was used.

Figure 1:
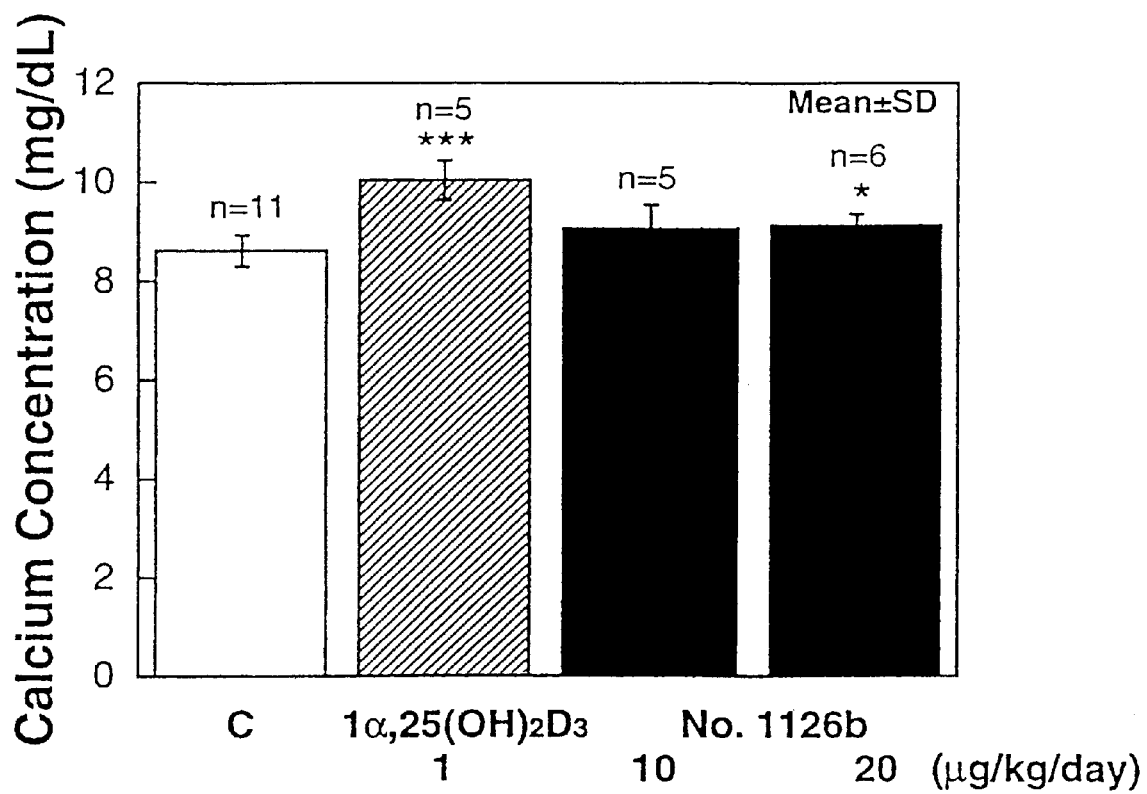
FIG. 1 is a drawing showing calcium concentrations in blood measured after the oral repeated administrations of an active vitamin $D_3$ (1 α, 25(OH)$_2$D$_3$) or a compound (No. 1126b) of the present invention for two weeks to mice in which human malignant tumor cells have been transplanted under the renal capsule.

The results of the blood calcium concentrations determined are shown in FIG. 1, and the results of the studies of the growth suppressing effect of the transplanted malignant tumor cells are shown in FIG. 2 (transplantation of HL-60) and in FIG. 3 (transplantation of HT-29).

In the 1 α, 25(OH)$_2$D$_3$ administration group, growth suppressing effects are observed both in cases of HL-60 cell and HT-29 cell as shown in FIG. 2 and FIG. 3, and the blood calcium level has been extremely increased compared with the control as shown in FIG. 1.

On the other hand, in the compound No. 1126b administration group, growth suppressing effects are observed both in cases of HL-60 cell and HT-29 cell, and the blood calcium increasing effect at these concentrations are observed at only slight degree.

Thus, the results of Examples 39–42 show that compounds of the present invention have differentiation inducing effects and growth suppressing effects on malignant tumor cells in vitro, and have elevation effects on blood calcium levels which are extremely reduced compared with that of 1 α, 25(OH)$_2$D$_3$ in vivo, and further they have growth suppressing effects on transplanted malignant tumor cells at doses which scarcely show elevation effects on blood calcium concentration. By these findings, it has been demonstrated that compounds of the present invention are effective as treating agents for malignant tumors.

Example 43

Production of Tablets

Tablets, each compound of the following components, were produced.

| | |
|---|---|
| The compound No. 1144b | 50 mg |
| Lactose | 230 mg |
| Potato starch | 80 mg |
| Polyvinylpyrrolidone | 11 mg |
| Magnesium stearate | 5 mg |

A compound (compound No. 1144b) of the present invention, lactose and potato starch were mixed. The mixture was homogeneously wetted with 20% solution of polyvinylpyrrolidone in ethanol, passed through a 20-mesh sieve, dried at 45° C. and passed again through a 15-mesh sieve. To thus obtained granules was added magnesium stearate, and the mixture was compressed to tablets.

Industrial Field of Application

Medicines containing vitamin D$_3$ derivatives expressed by the above formula [1] of the present invention as active ingredients can be used for treating inflammatory respiratory diseases.

Further, medicines containing vitamin D$_3$ derivatives expressed by the above formula [1] of the present invention as active ingredients can be used for treating malignant tumors.

On the other hand, the blood calcium level increasing effects of vitamin D$_3$ derivatives of the present invention have been extremely reduced compared with that of 1 α, 25-dihydroxyvitamin D$_3$.

Furthermore, vitamin D$_3$ derivatives expressed by the above formula [1] of the present invention have immunosuppressive effects such as the stimulation of maturation and differentiation of a cell, and the inhibition of interleukin-2 production, and the derivatives further have effects to stimulate the production of microbicidal oxygen metabolite and the chemotactic reaction of a leukocyte as immunological synergistic effect. Medicines containing vitamin D$_3$ derivatives of the present invention as active ingredients can therefore be agents for treating psoriasis, rheumatoid arthritis, inflammatory diseases such as dermatitis and autoimmune diseases, supplementary agents in chemotherapy for infections, and treating agents in therapeutic phases to which mononuclear phagocytes are associated.

Besides these diseases, medicines containing vitamin D$_3$ derivatives of the present invention as active ingredients can be used also for treating hypertension, diabetes mellitus, acne or osteoporosis, or stimulating hair growth.

We claim:

1. A vitamin $D_3$ derivative expressed by the following general formula (1)

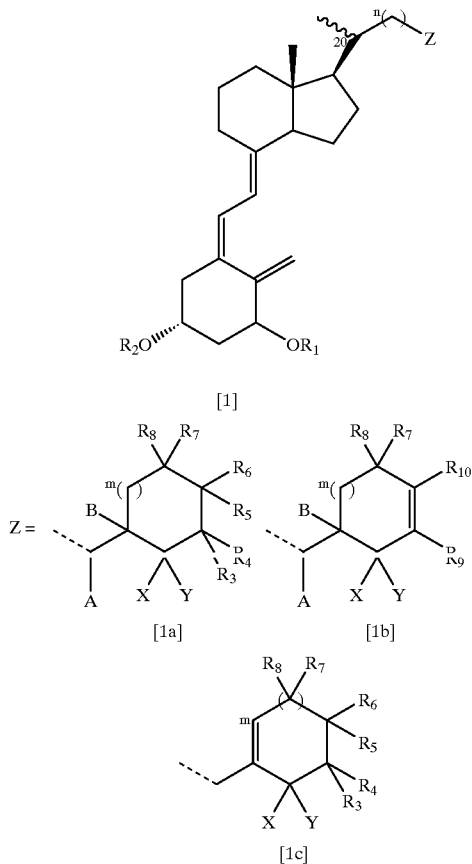

wherein, Z is 1a, 1b or 1c; $R_1$ and $R_2$ are identical to or different from each other, and are each a hydrogen atom, a tri($C_1$–$C_7$ alkyl)silyl group, an acetyl group, a methoxymethyl group, or a tetrahydropyranyl group; $R_3$ and $R_4$ are identical to or different from each other, and are each a hydrogen atom, a hydroxyl group, a $C_2$–$C_8$ acyloxy group, a $C_1$–$C_7$ alkyloxy group, a $C_1$–$C_6$ alkylthio group or a $C_1$–$C_7$ alkyl group which is optionally substituted with a hydroxyl group, a $C_2$–$C_8$ acyloxy group or a $C_1$–$C_7$ alkyloxy group; $R_5$, $R_6$, $R_7$ and $R_8$ are identical to or different from each other, and are each a hydrogen atom, a hydroxyl group, a $C_1$–$C_7$ alkyl group or a $C_2$–$C_8$ acyloxy group; $R_9$ is a hydrogen atom, a hydroxyl group, a $C_1$–$C_7$ alkyl group or a $C_1$–$C_6$ alkylthio group; $R_{10}$ is a hydrogen atom, a $C_1$–$C_7$ alkyl group or a $C_1$–$C_7$ alkyloxy group; A and B are identical to or different from each other, and are each a hydrogen atom, a hydroxyl group, or together express a single bond and express a double bond in cooperation with the single bond already shown in the formula; X and Y together express (i) a carbonyl group in cooperation with the carbon atom to which they are bonded, (ii) one of them is a hydrogen atom and the other is a hydroxyl group, or (iii) one of them is a hydrogen atom and the other is a $C_2$–$C_8$ acyloxy group; n is an integer of 0 to 2; m is an integer of 0 to 2; or a pharmaceutically permissible solvate thereof.

2. A vitamin $D_3$ derivative or a pharmaceutically permissible solvate thereof as claimed in claim 1, wherein both of $R_1$ and $R_2$ in the above formula (1) are hydrogen atoms.

3. A vitamin $D_3$ derivative or a pharmaceutically permissible solvate thereof as claimed in claim 1 or claim 2, wherein Z in the above formula (1) is (1a) or (1b).

4. A vitamin $D_3$ derivative or a pharmaceutically permissible solvate thereof as claimed in claim 1 or claim 2, wherein Z in the above formula (1) is (1a).

5. A vitamin $D_3$ derivative or a pharmaceutically permissible solvate thereof as claimed in claim 1 or claim 2, wherein Z in the above formula (1) is (1b).

6. A vitamin $D_3$ derivative or a pharmaceutically permissible solvate thereof as claimed in claim 1 or claim 2, wherein Z in the above formula (1) is (1c).

7. A vitamin $D_3$ derivative or a pharmaceutically permissible solvate thereof as claimed in claim 1, wherein both of $R_7$ and $R_8$ in the above formula (1) are each a hydrogen atom or a $C_1$–C7 alkyl group.

8. A vitamin $D_3$ derivative or a pharmaceutically permissible solvate thereof as claimed in claim 1, wherein both of $R_5$ and R6 in the above formula (1) are each a hydrogen atom or a $C_1$–$C_7$ alkyl group.

9. A vitamin $D_3$ derivative or a pharmaceutically permissible solvate thereof as claimed in claim 1, wherein both of A and B in the above formula (1) are each a hydrogen atom or together express a single bond and express a double bond in cooperation with the single bond already shown in the formula.

10. A vitamin $D_3$ derivative or a pharmaceutically permissible solvate thereof as claimed in claim 1, wherein m in the above formula (1) is 0 or 1.

11. A vitamin $D_3$ derivative or a pharmaceutically permissible solvate thereof as claimed in claim 1, wherein n in the above formula (1) is 0 or 1.

12. A vitamin $D_3$ derivative or a pharmaceutically permissible solvate thereof as claimed in claim 1, wherein, in the above formula (1), (a) either of $R_3$ and $R_4$ is a hydroxyl group, and the other is a $C_1$–$C_7$ alkyl group optionally substituted with a hydroxyl group, a $C_2$–$C_8$ acyloxy group or a $C_1$–$C_7$ alkyloxy group;

(b) either of $R_3$ and $R_4$ is a hydrogen atom, and the other is a $C_1$–$C_7$ alkyl group optionally substituted with a hydroxyl group, a $C_2$–$C_8$ acyloxy group or a $C_1$-$_7$ alkyloxy group;

(c) both of $R_3$ and $R_4$ are each a hydrogen atom, or (d) both of $R_3$ and $R_1$ are each a $C_1$–$C_7$ alkyl group optionally substituted with a same or different group selected from the group consisting of a hydroxyl group, a $C_2$–$C_8$ acyloxy group and a $C_1$–C7 alkyloxy group.

13. A treating agent for an inflammatory respiratory disease containing a therapeutically effective amount of a vitamin $D_3$ derivative or a pharmaceutically permissible solvate thereof as claimed in claim 1.

14. A treating agent for an inflammatory respiratory disease as claimed in claim 13, wherein the inflammatory respiratory disease is one or not less than two inflammatory respiratory diseases selected from a group consisting of acute upper airway infection, chronic sinusitis, allergic rhinitis, chronic lower airway infection, pulmonary emphysema, pneumonia, asthma, pulmonary tuberculosis sequela, acute respiratory distress syndrome and pulmonary fibrosis.

15. A treating agent for inflammatory respiratory disease as claimed in claim 14, wherein the acute upper airway infection is one or not less than two kinds of diseases selected from a group consisting of common cold, acute pharyngitis, acute rhinitis, acute sinusitis, acute tonsillitis, acute laryngitis, acute epiglottitis and acute bronchitis.

16. A treating agent for inflammatory respiratory disease as claimed in claim 14, wherein the chronic lower airway infection is one or not less than two kinds of diseases selected from a group consisting of chronic bronchitis, diffuse panbronchiolitis and bronchiectasis.

17. A treating agent for one or not less than two kinds of acute upper airway infections selected from the group consisting of common cold, acute pharyngitis, acute rhinitis, acute sinusitis, acute tonsillitis, acute laryngitis, acute epiglottitis and acute bronchitis containing a therapeutically effective amount of a vitamin $D_3$ derivative or a pharmaceutically permissible solvate thereof as claimed in claim 1.

18. A treating agent for one or not less than two kinds of chronic lower airway infections selected from the group consisting of chronic bronchitis, diffuse panbronchiolitis and bronchiectasis containing a therapeutically effective amount of a vitamin $D_3$ derivative or a pharmaceutically permissible solvate thereof as claimed in claim 1.

19. A treating agent for a malignant tumor containing a therapeutically effective amount of a vitamin $D_3$ derivative or a pharmaceutically permissible solvate thereof as claimed in claim 1.

20. A treating agent for a disease selected from a group consisting of rheumatoid arthritis, osteoporosis, growth diabetes mellitus, hypertension, alopecia, acne, psoriasis and dermatitis containing a therapeutically effective amount of a vitamin $D_3$ derivative or a pharmaceutically permissible solvate thereof as claimed in claim 1.

21. A pharmaceutical composition composed of a vitamin $D_3$ derivative or a pharmaceutically permissible solvate thereof as claimed in claim 1 and a pharmaceutically permissible carrier.

22. A method for producing an active vitamin $D_3$ derivative or a pharmaceutically permissible solvate thereof as claimed in claim 1 consisting of treating a vitamin $D_3$ with hydroxyl groups at the first- and the third-positions protected with tri($C_1$–$C_7$ alkyl)silyl groups with a reagent comprising a combination of a tetrafluoroborate alkali metal salt and then a mineral acid for deprotection.

23. A method for producing an active vitamin $D_3$ derivative as claimed in claim 1, wherein $R_1$ and $R_2$ are each a tri($C_1$–$C_7$ alkyl)silyl group.

* * * * *